United States Patent
Harata et al.

(10) Patent No.: US 8,433,033 B2
(45) Date of Patent: Apr. 30, 2013

(54) PANORAMIC IMAGING APPARATUS

(75) Inventors: Yasuo Harata, Tokyo (JP); Kazuyuki Araki, Tokyo (JP); Koichi Ogawa, Tokyo (JP); Tsutomu Yamakawa, Tochigi (JP); Takashi Sue, Tokyo (JP)

(73) Assignee: Axion Japan Co., Ltd., Saitama (JP)

( * ) Notice: Subject to any disclaimer, the term of this patent is extended or adjusted under 35 U.S.C. 154(b) by 845 days.

(21) Appl. No.: 12/083,777

(22) PCT Filed: Oct. 19, 2006

(86) PCT No.: PCT/JP2006/320817
§ 371 (c)(1),
(2), (4) Date: Sep. 4, 2009

(87) PCT Pub. No.: WO2007/046458
PCT Pub. Date: Apr. 26, 2007

(65) Prior Publication Data
US 2009/0310845 A1    Dec. 17, 2009

(30) Foreign Application Priority Data

Oct. 21, 2005 (JP) .................................. 2005-306954

(51) Int. Cl.
*A61B 6/14* (2006.01)
*G06K 9/00* (2006.01)
(52) U.S. Cl.
USPC .............................. 378/38; 382/131; 382/132
(58) Field of Classification Search .................. 382/131, 382/132; 378/4, 38
See application file for complete search history.

(56) References Cited

U.S. PATENT DOCUMENTS 4,239,971 A    12/1980   Cushman
5,195,114 A *  3/1993   Sairenji et al. ................... 378/40
(Continued)

FOREIGN PATENT DOCUMENTS

EP    0 756 247    1/1997
JP    57-25837     2/1982
(Continued)

*Primary Examiner* — Alexander H Taningco
(74) *Attorney, Agent, or Firm* — Clark & Brody

(57) ABSTRACT

A panoramic imaging apparatus is provided, which is able to freely display a focus-optimized internal structural image of the tooth row depending on a position using image data acquired by only one-time X-ray panoramic imaging from an arbitrary section along a patient's tooth row.

The panoramic imaging apparatus comprise an X-ray source (31) and a detector (32) outputting a digital electrical signal depending on an incident X-ray at a constant frame rate. This apparatus further comprises means (24) for moving a pair of the X-ray source and the detector around an object in a state where the X-ray source and the detector are opposed to each other with the object located therebetween, means (54) for sequentially storing, as frame data, the electrical signal outputted by the detector, means (56) for producing a panoramic image of a desired section of the object based on the frame data, and means (56, 57, 58) for producing a partial sectional image using the frame data, the partial sectional image being an image of a partial region specified on the panoramic image and being focused depending on a desired position in an imaging space.

11 Claims, 33 Drawing Sheets

U.S. PATENT DOCUMENTS

| | | |
|---|---|---|
| 5,214,686 A | 5/1993 | Webber |
| 5,467,404 A | 11/1995 | Vuylsteke et al. |
| 5,740,224 A * | 4/1998 | Muller et al. .................... 378/11 |
| 5,784,429 A * | 7/1998 | Arai ................................ 378/38 |
| 5,828,721 A * | 10/1998 | Schulze-Ganzlin et al. .... 378/38 |
| 6,049,584 A | 4/2000 | Pfeiffer |
| 6,289,074 B1 * | 9/2001 | Arai et al. ........................ 378/4 |
| 2002/0122537 A1* | 9/2002 | Yoshimura .................... 378/208 |
| 2004/0264648 A1 | 12/2004 | Claus et al. |
| 2005/0117696 A1* | 6/2005 | Suzuki et al. .................... 378/19 |
| 2006/0203959 A1* | 9/2006 | Spartiotis et al. ............... 378/38 |
| 2009/0079738 A1* | 3/2009 | Liao ............................. 345/427 |
| 2009/0168954 A1* | 7/2009 | Kia et al. ........................ 378/38 |
| 2009/0323891 A1* | 12/2009 | Borghese et al. ............... 378/20 |

FOREIGN PATENT DOCUMENTS

| | | |
|---|---|---|
| JP | 57-203430 | 12/1982 |
| JP | 63-140906 | 6/1988 |
| JP | 02-084942 | 3/1990 |
| JP | 02128758 A * | 5/1990 |
| JP | 04-144548 | 5/1992 |
| JP | 04-144549 | 5/1992 |
| JP | 06-088790 | 3/1994 |
| JP | 06-169690 | 6/1994 |
| JP | 10-295680 | 11/1998 |
| JP | 3023633 | 3/2000 |

* cited by examiner (A)

ROI1

(B)

ROI2

PANORAMIC IMAGING APPARATUS

TECHNICAL FIELD

The present invention relates to a panoramic imaging apparatus for imaging panoramic images of a specified part of an object being imaged, such as a row of teeth, and a method of processing images for panoramic imaging, and in particular, to a panoramic imaging apparatus provided with a pair of an X-ray source and a digital type X-ray detector, which are arranged to be opposed to each other and to have an object located between the X-ray source and the X-ray detector, and with this arrangement, the paired X-ray source and the X-ray detector are moved along a predetermined orbit around the object, during which time X-rays radiated from the X-ray source and transmitted through the object are detected by the X-ray detector at intervals, so that digital X-ray transmission data detected by the X-ray detector are used to produce panoramic images of the object, and a method of processing images for the imaging processing.

BACKGROUND ART

Due to, in part, recent changes in food culture and lifestyle, the number of people who needs dental treatment is on the increase, so that dental specialists frequently recommend for routine examination and early treatment of teeth. In most cases, treating the teeth involves X-ray imaging that examines the states of the tooth (the row of teeth) and the gum-ridge. In many conventional cases, the X-ray imaging is used to provide images of regional gum-ridges projected onto X-ray films. As alternative imaging techniques or techniques for parallel use with the projected images, apparatuses such as an X-ray CT scanner, a dental panoramic imaging apparatus are also used.

The X-ray CT scanner is used to apply the general CT imaging to the jaw portion. Hence the resolution of panoramic images reconstructed along the tooth row from acquired images by the scanner is not so high, which has limited its application to observing the entire tooth row.

On the other hand, the dental panoramic imaging apparatus comprises an X-ray source and an X-ray detector which are paired and arranged with the head of an object located therebetween. The paired members are moved around the head to acquire X-ray transmission date, and the data are used to produce panoramic images along a predetermined section along the tooth row. An example of this dental panoramic imaging apparatus is provided by a patent reference 1 listed below.

In the patent reference 1, exemplified is a digital type of panoramic imaging apparatus (the title of the invention is "digital panoramic X-ray imaging apparatus"). This panoramic imaging apparatus is provided with an X-ray source and an X-ray image detecting member arranged to be opposed each other with an object being examined located therebetween and rotation deriving means for rotating the X-ray source and the X-ray image detecting member as one unit. The X-ray source is provided with an X-ray tube and a collimator collimating X-rays radiated from the X-ray tube into slit-shaped beam X-rays. The X-ray image detecting member is provided with an X-ray detector, which is for example an X-ray CCD sensor, outputting digital electrical signals depending on incident X-ray intensity. Further, this panoramic imaging apparatus is provided with storage means for sequentially storing, as frame images, image information acquired by the X-ray detector and image processing means for panoramic images. The image processing means reads out the image information from the storage means at intervals in sequence, and, in relation to a direction along which images spatially are related among the sequential image information, the read-out image information is added on one another with a predetermined amount of shift. Thus the image processing means produces panoramic images of an arbitrary section in accordance with both the read-out intervals and the shift amounts. Accordingly, it is possible to provide, as diagnostic images, on the monitor of a personal computer or other devices, panoramic images of sections along patients' tooth rows.

[Patent reference 1] Japanese Patent Laid-open Publication No. 4-144548.

DISCLOSURE OF THE INVENTION

Problems to be Solved by the Invention

However, even if the panoramic imaging on the by the foregoing dental panoramic imaging apparatus is used, panoramic images which are sufficiently met with a quality demand by dentists are not always provided.

For example, for obtaining panoramic images optimum for diagnosis, it is necessary to set the imaging position to an optimum appropriate section along a patient's tooth row, However, this is considerably difficult, because it is not easy to set a section passing a diagnostic portion which should be focused. For setting such an optimally focused section, it cannot help relying on operator's capability for imaging in most occasions. When the images for diagnosis are defocused, i.e., have blur, diagnostic work of dentists becomes heavier.

In addition, in the conventional dental panoramic imaging apparatus, it is impossible to obtain, from the acquired panoramic images, internal structural information of each tooth or the gum-ridge, together with information showing a position where the internal structure information is acquired or in response to specifying the position, in the depth direction of the tooth row (gum-ridge) (i.e., the cross direction to the tooth row or the thickness direction of each tooth). Namely, it is impossible to freely specify such a position and obtain the internal structural information at the specified position in the tooth or gum-ridge. Additionally, it is also impossible to specify a three-dimensional position to obtain information about the internal structure of a tooth row and gum-ridge at the specified three-dimensional potion. That is, information about structures other than a tooth-row section in the panoramic images is hardly provided. The shapes and angles of the teeth differ from each other even among the tooth row of each individual and differ from each other among individuals. Thus, even when a dentist, who interprets images, desires to observe a more rearward portion or a more frontward portion, an oblique section along a tooth, or a section along the thickness direction of a tooth, it is difficult for the dentist to freely observe another portion. Thus information is thus likely to be short on whether a cavity and/or alveolar pyorrhea exists in which portion of a tooth and on the positional relationship of blood vessels and nerves in the gum-ridge.

To compensate such an information shortage, another imaging process for complementing panoramic images is required. The complementary techniques include intraoral imaging for only a region of interest and X-ray tomographic imaging carried out a panoramic imaging apparatus or another apparatus. In this way, the panoramic images are not sufficient for diagnosis, requiring information complementing the acquired panoramic images. This means that, for diagnosis, the time taken is longer and work becomes heavier, lowering patients throughput, being subjected to undesirable patients' X-ray exposure due to re-imaging.

The present invention has been made in consideration of the foregoing difficulties the conventional digital panoramic imaging faces, and a main object of the present invention is to provides a panoramic imaging apparatus which is able to provide any high-resolution panoramic images of focused sections in the depth direction of a tooth row and the gum-ridge, together with their distance information, using image data acquired by X-ray panoramic imaging to be carried out only one time from a specified section along a patient's tooth row, thus being easier in use for interpreting the panoramic images.

Means for Solving the Problem

In order to achieve the object, one aspect of the present invention provides a panoramic imaging apparatus characterized in that the apparatus comprises: an X-ray source radiating an X-ray; a detector outputting a digital electrical signal depending on an incident X-ray at a constant frame rate; movement drive means for moving a pair of the X-ray source and the detector around an object in a state where the X-ray source and the detector are opposed to each other with the object located therebetween; storage means for storing, as frame data, the electrical signal outputted by the detector at the constant frame rate while the movement drive means moves the X-ray source and the detector around the object; panoramic image producing means for producing a panoramic image of a desired section of the object based on the frame data stored in the storage means, the desired section being specified previously; and partial sectional image producing means for producing a partial sectional image using the frame data, the partial sectional image being an image of a partial region specified on the panoramic image and being focused depending on a desired position in a space in which the X-ray source and the detector are moved by the movement drive means.

Another aspect of the present invention provides a method of processing images in panoramic imaging, comprising steps of: sequentially storing, as frame data, a digital electrical signal outputted at a constant frame rate from a detector, wherein a pair of an X-ray source and the detector is moved around an object in a state where the X-ray source and the detector are opposed to each other with the object located therebetween; producing a panoramic is image of a section previously specified, using the stored frame data; and producing, using the frame data, a partial sectional image of a partial region specified on the panoramic image so that the partial sectional image is focused at a desired position in a space in which the X-ray source and the detector are moved.

Advantageous Effects of the Invention

According to the present invention provides a panoramic imaging apparatus which is able to provide any high-resolution panoramic images of focused sections in the depth direction of a tooth row and the gum-ridge, together with their distance information, using image data acquired by X-ray panoramic imaging to be carried out only one time from a specified section along a patient's tooth row, thus being easier in use for interpreting the panoramic images.

BEST MODE FOR CARRYING OUT THE INVENTION

Referring to the accompanying drawings, best modes (embodiments) for carrying out the present invention will now be described First Embodiment Referring to FIGS. 1-31, a first embodiment of the panoramic imaging apparatus according to the present invention will now be described.

FIG. 1 shows the appearance of a panoramic imaging apparatus 1 according to the present embodiment. As shown, this panoramic imaging apparatus 1 comprises a chassis 11 and a control/calculation unit 12 composed of a computer system, where the chassis 11 allows an object (patient) P being examined to stand up to acquire black-and-white original image data for producing panoramic images, and the control/calculation unit 12 controls data acquisition carried out by the chassis 11, takes in the acquired data to produce panoramic images, and post-processes the produced panoramic images interactively with an operator (doctor or engineer).

The chassis 11 is provided with a stand unit 13 and an imaging unit 14 which can be moved up and down in relation to the stand unit 13. The stand unit 13 is provided with a base 21 fixed on the floor and a pillar 22 standing up on the base 21. In the present embodiment, the pillar 22 is formed into a rectangular column, whose one side accepts the imaging unit 14 so that the unit 14 can be moved up and down therealong in a predetermined longitudinal range.

For the sake of making the explanation easier, the XYZ orthogonal coordinate system is employed, in which the Z-axis is assigned to the longitudinal direction of the pillar 22, that is, the up-and-down direction. Incidentally, in two-dimensional panoramic images later described, the lateral direction of the images is denoted as an x-axis and the longitudinal direction thereof is denoted as a y-axis.

The imaging unit 14 is provided with a up-and-down unit 23, which is approximately U-shaped when viewed from a side thereof, and a rotation unit 24 rotatably supported by the up-and-down unit 23. The up-and-down unit 23 is movable within a predetermined longitudinal range in the Z-axis direction (i.e., the longitudinal direction) using a drive mechanism 31 (for example, composed of a motor and rack-and-pinion parts). For this movement, a command is issued from the control/calculation unit 12 to the drive mechanism 31.

The up-and-down unit 23 forms an approximately U-shaped side view, as described, and is provided a unitary member having an upper arm 23A and a lower arm 23B, which are located on upper and lower sides, and a longitudinal arm 23C connects both upper and lower arms 23A and 23B. The longitudinal arm 23C is supported by the pillar 22 in an up-and-down movable manner. Of the arms 23A-23C, the upper arm 23A and the longitudinal arm 23C cooperate with each other to provide an inner space for imaging. Inside the upper arm 23A, there is provided a rotation drive mechanism 30 (for example, composed of members such as an electronic motor and a speed reduction gear), This rotation drive mechanism 30 receives a command for driving the rotation from the control/calculation unit 12. This mechanism 30 has an output shaft, that is, the rotation shaft of the electronic motor, is arranged to protrude downward (in the Z-axis direction) from the upper arm 23A and the rotation shaft is coupled with the rotation unit 24. That is, the rotation unit 24 is hung from the up-and-down unit 23 and rotatable in response to the drive of the rotation drive mechanism 30.

The lower arm 23B, which has a predetermined length, extends in the same direction as the upper arm 23A and provides a tip end on which a chinrest 25 is provided. The chinrest 25 accepts a mouthpiece 26 detachable thereto. The mouthpiece 26 is bitten by a patient P being examined. Thus the chinrest 25 and the mouthpiece 26 positionally fix the mouth cavity portion of the patient P.

The rotation unit 24 has an approximately U-shaped side view, as its appearance in the used state, and has an open end directed downward and rotatably secured to the motor output shaft from the upper arm 23A. Specifically, the rotation unit 24 is a unitary member having a lateral arm 24A which laterally rotates, that is, rotates in a plane which is approximately in parallel with the XY plane and right and left longitudinal arms (i.e., a first longitudinal arm and a second longitudinal arm) 24B and 24C which extend downward (in the Z-axis direction) from both ends of the lateral arm 24A. The lateral arm 24A as well as the right-and-left first and second arms 24B and 24C have a significant role for the data acquisition. Thus mechanisms and parts necessary for the data acquisition are provided in the inner space of the arms 24A to 24C so as to be driven and operated under the control of the control/calculation unit 12.

Practically, an X-ray tube 31, serving as a radiation source, is provided at a lower end part inside the first longitudinal arm 24B and has an emission window through which radiated X-rays pass toward the second longitudinal arm 24C. On the other hand, at a lower end part inside the second longitudinal arm 24C, a digital type X-ray detector 32 serving as radiation-ray detecting means is provided, in which X-ray detecting elements are arranged in a two-dimensional, but slit shape (for example, 64×1500 matrix shape). The X-ray detector 32 has an incident window through which the X-rays come in. An example of this detector 32 is a CdTe line detector (for example, 6.4 mm in width×150 mm in longitudinal). This detector 32 is arranged in the longitudinal attitude that the longitudinal direction thereof agrees with the Z-axis direction. The detector 32 has an incident area 32A with an incident window IW, which is loaded with a slit-like collimator 33 (which is opposed to the incident area 32A). The collimator 33 cuts off X-rays scattering to the detector 32 so that the incident X-rays are collimated in accordance with an actual collecting window of the detector (for a window having a width of 3.5 mm, so that an effective width in the lateral direction of the detector 32 is approximately 3.5 mm). The detector 32 is able to acquire the incident X-rays at a frame rate of 300 fps, for example, (one frame is composed of 64×1500 pixels, for example) in the form of digital-amount electrical image data depending on the X-ray amounts. Hereinafter the acquired data is called "frame data" (or original frame data).

For imaging, the X-ray tube 31 and the detector 32, which are paired, are located to be opposed to each other, with the mouth cavity portion of the patient P located therebetween and driven to rotate around the mouth cavity portion as one rotation member. In this rotation, the paired X-ray tube 31 and detector 32 are driven to focus on a desired section along the tooth row of the mouth cavity portion (precisely, a later-described standard section (standard tomographic section)) and trace the standard section. This standard section is an approximately horseshoe shape when viewed in the Z-axis direction. In tracing the standard section, the X-ray tube 31 and the detector 32 are not always rotated at the same angular speed, but as a broader concept, the rotation should be "a movement along a circular arc." In addition, the standard section is a plane which is in parallel with the incident area 32A of the detector 32 (refer to FIG. 2). In the present embodiment, the incident area 32A is located so as to agree with the Z-axis direction.

FIG. 2 shows an electrical block of the panoramic imaging apparatus for control and processes therefor. As shown, the X-ray tube 31 is connected to the control/calculation unit 12 via a high-voltage generator 41 and a communication line 42, while the detector 32 is connected to the control/calculation unit 12 via a communication line 43. The high-voltage generator 41 is provided in the pillar 22, the up-and-down unit 23, or the rotation unit 24 and responds to a control signal coming from the control/calculation unit 12 so as to be controlled based on X-ray radiation conditions such as tube current and tube voltage to the X-ray tube 31 and a radiation timing sequence.

The control/calculation unit 12 is composed of, for example, a personal computer which is able to process and store a large amount of image data. This control/calculation unit 12 is provided with, as its essential components, interfaces 51, 52 and 62 communicated mutually communicably via an internal bus 50, a buffer memory 53, an image memory 54, a frame memory 55, an image processor 56, a controller (CPU) 57, and a D/A converter 59. The controller 57 is communicably connected to an operation device 58 and the D/A converter 59 is also connected to a monitor 60.

Of these components, the interfaces 51 and 52 are connected to the high-voltage generator 41 and the detector 32, respectively, so as to relaying control information and acquired data communicated between the controller 57, and the high-voltage generator 41 and the detector 32. The other interface 62 connects the internal bus 50 and the communication line such that the controller 57 is communicable with external devices. Thus the controller 57 is allowed to take in intraoral images acquired by an external intraoral X-ray imager and to transmit to external servers both panoramic images acquired the present panoramic imaging apparatus and focus-optimized images (described later) from the panoramic images on the regulation of for example DICOM (Digital Imaging and Communications in Medicine).

The buffer memory 53 temporarily stores digital frame data coming from the detector 32, which data is received via the interface 52.

The image processor 56, which is placed under the control of the controller 57, executes, interactively with an operator, production of a panoramic image of a standard section along a patient's tooth row and processes for using the panoramic images after imaging. Programs for these functions are previously stored in the ROM 61. In the present invention, the standard section is a tomographic image selected from a plurality of tomographic images prepared previously. That is, the position of the standard section is changeable in given range in the depth direction of the tooth row. The production of the panoramic images and the post-processing for interpretation are essential features of the present panoramic imaging apparatus, which will thus be detailed later.

Frame data and image data being processed by or produced during a process in the image processor 56 are stored in the image memory 54 in a readable and writable manner. As the image memory 54, large-capacity recording mediums (non-volatile and readable/writable mediums) such as hard disks are adopted. The frame memory 55 is used to display panoramic image data that has been produced and/or post-processed. The image data stored in the frame memory 55 are read out by the D/A converter 59 at intervals to be converted into analog signals, and displayed on the screen of the monitor 60.

The controller 57 controls the operations of the components of the apparatus based on programs previously stored in the ROM 61 for the overall control and processing. Those programs are set such that the apparatus allows an operator to interactively receive operative information. Thus as described later, the controller 57 engages in interactive control for producing a panoramic image of a standard section, setting parameters (i.e., gain described later) necessary for reconstruction which is responsible for focus-optimizing the panoramic image, and acquiring (scanning) frame data, based on operative information from the operator, which is provided from the operation device 58.

As shown in FIG. 1, a patient stands or sits to locate his or her head at the chinrest 25, and bites the mouthpiece 26 to push his or hear forehead to the headrest 28. This allows the patient head portion (jaw portion) to be fixedly located at an approximate central part of the rotation space in which the rotation unit 24 rotates. In this located state, under the control of the controller 57, the rotation unit 24 is made to rotate around the patient's head along the XY plane and/or a plane oblique to the XY plane (refer to arrows in FIG. 1).

During the rotation, under the control of the controller 57, the high-voltage generator 41 drives the X-ray tube 31 in a pulse mode such that the generator supplies radiating high voltage (specified tube voltage and tube current) to the X-ray tube 31 in the pulse mode in which pulsed voltages are applied at intervals. This permits the X-ray tube 31 to radiate pulsed X-rays at intervals. The X-rays passes through the jaw portion (i.e., the tooth row portion) of the patient located at the imaging position and makes incidence into the line sensor type of detector 32. As stated, the detector 32 detects the incident X-rays at very high frame rates (for example, 300 fps), and outputs corresponding two-dimensional electrical digital data (for example, 64×1500 pixels) in sequence. This digital data is treated as the foregoing frame data, so that the data are stored temporarily in the buffer memory 53 via the communication line 43 and via the interface 52 of the control/calculation unit 12. This temporarily stored frame data are then transferred to the image memory 53 for storage therein.

The image processor 56 is thus able to use the frame data stored in the image memory 53 to produce, that is, reconstruct a panoramic image of the standard section employed along the tooth row. Further, this image processor 56 uses frame data composing a region of interest (ROI) specified on the panoramic image so as to produce, that is, reconstruct a focus-optimized image. An additional remark is that the panoramic image itself is a sectional image of the entire standard section, which is produced with an intention of optimizing the focus. However, in effect, since the individuals have different shape tooth rows, only the reconstructed images of the standard sections are difficult to provide least focus blur in each region of each image (i.e., best focused or optimized focus). The present embodiment considers this fact, so that, using the panoramic image (at least a sectional image which covers the whole tooth row) of the standard section, reconstruction is further made to produce additional sectional images which provide clear internal structures (with less blur and focused). Normally this additional reconstruction is directed to a partial region of the panoramic image which serves as a base image. Accordingly, in the present embodiment, the sectional image of this partial region is referred to as a focus-optimized image.

In this way, producing both the panoramic image and the focus-optimized image involves a process called reconstruction. Though being detailed later, this reconstruction is a process to synthesize (superpose, overlap, or combine) frame data on one another and add their pixel values to each other. The region of interest which is set on the panoramic image serving as the base image is usually is specified as a local region composing part of the panoramic image. However, the region of interest can be set as the whole region of the panoramic image. Of course, the focus-optimized image can be produced when a doctor desires such an image.

The data of the panoramic image and/or the focus-optimized image are stored in the image memory 54 and those images are displayed on the monitor 60 in a proper mode. In the foregoing steps, operator's desire can be reflected in at least selecting the standard section, setting the region of interest, changing sectional positions, selecting the display mode, and others.

Imaging and interpreting the panoramic image using the panoramic imaging apparatus 1 can be outlined as above However, producing the panoramic image of the standard section and the focus-optimized image of a specified region needs a concept of "gain." In the present embodiment, this "gain" is set in advance through a calibration step. The data of the gain is previously stored in a predetermined area of the image memory 54 as a look-up table LUT.

All items necessary for producing the panoramic image of a whole tooth row and the focus-optimized image of a specified region, which are executed in this panoramic imaging apparatus 1, will now be detailed item by item, including the concept of the "gain" and "setting the gain using a phantom."

(Concept of Gain)

In the present panoramic imaging apparatus 1, a panoramic image of the standard section (a kind of desired section) taken along a tooth row specified (or selected as stated later) is produced by synthesizing frame data, which are acquired at high speed (for example, 300 fps), on one another with their positions shifted gradually and adding their pixel values to each other. Each of the frame data is a set of X-ray transmissive data mapped as a long two-dimensional slit form, which can be regarded as a line shape. This synthesizing addition is an essential part of the "reconstruction." The synthesizing addition enhances differences in levels of the pixel values, which allows structural parts (teeth, gum-ridge, others) to be depicted at higher densities, compared to the remaining parts. This theory is utilized in this panoramic imaging. In the present embodiment, the gain is defined as an amount indicating "a degree of synthesis" that a plurality of sets of frame data should be mutually synthesized, that is, how far each of the frame data sets is shifted from the others for synthesis and addition, when the plurality of sets of frame data are subjected to the synthesizing addition.

When the gain is smaller, the degree of the synthesis becomes denser, while when the gain is larger, the degree of the synthesis becomes coarser. How frame data are synthesized is shown in (A) and (B) in FIG. 12, where the figure (A) shows a state where the gain is small and the figure (B) shows a state where the gain is large, respectively. In this way, the concept of degree (i.e., coarse/dense) of the synthesis, which depends on the largeness of the gain, is the opposite to that directed the normal electric circuitry. This is owing to the fact that, as will be detailed later, "the gain corresponds to the gradient" of a speed (called a speed curve) in the coordinate of which abscissa axis depicts frame data and of which longitudinal axis depicts positions where frame data are mutually added in the memory space. Such positions correspond to mapping positions, which show pixel positions of a reconstructed panoramic image. The speed curve will be detained further.

Further, as stated above, changing the gain, i.e., the amount of synthesis of frame data results in changes in image gray levels, image by image, to be produced. In other words, by changing sections to be reconstructed, the gray levels are changed image by image, making the interpretation difficult. Thus it is required to multiply respective pixel values of a reconstructed image by coefficients proportional or directly proportional to used gains so that the contrasting densities become equal among images.

One example of the gain is used based on a simplified model shown in FIG. 3. As shown therein, when the X-ray tube 31 and the detector 32 are moved such that a ratio between distances D1 and D2 relative to an object OB (the tooth row of a patient's jaw) is kept constant and a relative speed between those members is kept at a given value, amounts of synthesizing frame data (i.e., gains) which provide no blur to the object OB (that is, focused) are decided. The distances D1 and D2 show distances in each direction (i.e., the depth direction) along each of lines each connecting the X-ray tube and the detector at each of points in a tooth row during scanning is made.

In other words, when the scan is made as above, the relative operation speed and the gain define a focused plane (a focused continuous section). Since this focused plane corresponds to the ratio between the distances D1 and D2, the focused plane is located at a plane moved in parallel from the detector 32 in each depth direction.

In general, when the gain becomes smaller, the focused position gets closer to the X-ray tube 31 in each depth direction Ddp, while when the gain becomes larger, the focused position gets further from the X-ray tube 31 in each depth direction Ddp. Thus, a phantom (later described) is used to know quantitatively the distance between the X-ray tube 31 and the detector 32 in the respective depth directions. And quantitative measurement (setting), which provides information as to what amount of gain is required for the focusing, is previously made at each position on the linear line along each depth direction. Namely the relationship between the respective positions (i.e., the respective distances from the standard section) and the gains is measured in advance, and information indicative of the relationship is stored in the look-up table LUT as described.

The scan for this preliminary measurement is performed in the state where a phantom is placed at the chinrest 25 and the pair of the X-ray tube 31 and the detector 32 is rotated. The trajectory and speed of this rotation are the same as those for actual imaging (scan).

In addition, in terms of the characteristic of the gain, the gain in the direction (Z-axis direction), that is, the longitudinal direction, which is in parallel with the incident area 32A of the detector 32 (i.e., a plane into which the X-rays enter; refer to FIG. 2) is constant at each of the positions residing in the XY plane. Thus, when the detector 32 is located at a position, the gains at the respective positions (in the XY plane) along the depth direction passing through the detector 32 differ from each other, but all the gains along the Z-axis directional plane passing each position, which is in parallel with the incident area 32A, are the same.

Of course, besides the technique that employs the foregoing table reference, the relationship with the gains may be possessed in the form of an arithmetic expression, so that the gain is calculated at each position in each depth direction. A further modification is that, instead of calculating the gain at each position in each depth direction, the calculated gain is to finally convert the gains over the scanning space including the gain calculated positions (including the tooth row) to values expressed with the polar or orthogonal coordinate representation so that the converted gains are used for reconstructing images.

Hence, reference to the look-up table LUT gives the gains at respective mapping positions along a section to be focused differently from the standard section subjected to the first image reconstruction. These gains are used to mutually synthesize frame data, which gives pixel values to the respective mapping positions in sections including the standard section, producing panoramic images. These sections are basically perpendicular to the XY plane, but may be oblique to the XY plane (and YZ plane and/or XZ plane).

(Phantom Used in Preliminary Measurement)

As stated above, in the present embodiment, a phantom is used for preliminarily measuring the relationship between the distances in the depth directions and the gains in a quantitative manner.

In general, an alignment of teeth, i.e., a tooth row, is horseshoe-shaped, so that the alignment is divided into a plurality of scan regions depending on their curvatures (front tooth region and back tooth regions). In the respective scan regions, a scan is made to trace the standard section which is set along the horseshoe shape, during which time the foregoing distances D1 and D2 are changed. In this way, the phantom is used to qualitatively measure the relationship between the distances in each depth direction and the gains, where the measurement is performed at given intervals in the direction along the tooth row (for example, in FIG. 4, the distance between the i-th depth direction and the i+1-th depth direction is 10 mm).

Examples of the phantom for the preliminary measurement are shown in FIGS. 5-7. FIGS. 5 and 6 exemplify a first phantom FT1. Preferably, this phantom FT1 comprises a base 71 (refer to FIG. 6), a plurality of measurement plates 72 (refer to FIG. 5), a chinrest fixing member 73, and a plurality of phantom members 74. Specifically, the base 71 is made of for example a lead plate, which is less in X-ray absorption, but stiff and horseshoe-shaped. The measurement plates 72, which are made of for example acrylic plates, are built on the base 71 so as to extend oblique-upward from one end of the base 71 at a given angle θ (for instance, 45 degrees). The chinrest fixing member 73 extends from another end of the base 71. The phantom members 74 are made of a plurality of for example lead balls arranged on one face of each measurement plate 72 over a predetermined range in its longitudinal direction at intervals therealong. The predetermined range covers a predetermined distance range R1 (for instance, 20 mm) in the horizontal plane (i.e., XY plane) and the predetermined interval corresponds to a small distance of R2 (for instance, 5 mm) in the horizontal plane (i.e., XY plane).

Each measurement plate 72 makes an angle θ with the base 71, so that this angle θ gives the measurement plates 72 a tilt to the X-ray projecting direction by an angle θ. The plural measurement plates 72 are arranged on the base such that the plates virtually cross a tooth row (refer to a dotted line L1 in FIG. 6) and have a predetermined pitch P1 (for example, 10 mm) between plates in around back tooth regions (refer to FIG. 6). Each of the phantom members 74 has a diameter (for example, 1 mm) which is smaller than the smaller distance R2 and which enables sufficient visual observation of blurs. Thus the small distance R2 corresponds to a distance between the central positions of mutually adjacent two phantom members. In addition, the predetermined distance range R1 is set to have a spatial range to enable the observation of a horseshoe-shaped section in a tooth row.

It is preferred that the attachment position of each measurement plate 72 to the base 71 is adjustable using an adjustable mechanism AD in the depth direction This adjustment is realized by for example by shifting a screw clamp position.

FIG. 7 exemplifies another phantom FT2. This phantom FT2 is employed instead of the phantom members 74 mapped on each measurement plate 72 of the foregoing phantom FT1 and uses a strip-shaped thin-film phantom member 74A made of hard lead. This phantom member 74A has dimensions of, for example, a width of 5 mm, a length of 21.2 mm (the predetermined distance range R1), and a thickness of approximately 0.5 mm, with no burr, with sizes processed accurately. The respective longitudinal positions of this phantom member 74A can be decided using the linearity thereof, as long as a distance between one end of the phantom member 74A and one end of each measurement plate 72 is known. The other structures are similar to those shown in FIGS. 5 and 6.

Even when using any of the above phantoms FT1 and FT2, it is possible to measure focus blurs and their distances, Specifically, for using the first phantom FT1, from a panoramic image acquired by a scan by which the preliminary measurement is performed, it is possible to visually observe images in which the lead balls composing the plurality of phantom members 74 on each measurement plate 72 are depicted, as to what degree those lead balls blur. On the other hand, in the case of the second phantom member FT2, the similar image is used to visually observe blurred degrees of both the ends of the strip-shaped lead plate, which composes the phantom member 74A on each measurement plate 72, and the ends of each measurement plate 72 itself. On the basis of this observation, when blurs are visually observed in the phantom members 74 on each measurement plate 72 or in the longitudinal directions of the phantom member 74A on each measurement plate 72, the gain is adjusted in a trial and error manner to observe another image. Through this adjustment and observation, a gain that provides the least blur(s) at the current position can be decided as a focus-optimizing gain at that position in the current depth direction. That is, this gain shows an amount of synthesis of frame data which provide that image having the least blur(s). The image processor 56 recognizes the synthesis amount at the position of each phantom member, and transmits the synthesis amount, as the gain, to the controller 57.

The phantom FT may be modified such that X-ray non-transmissive plate-shaped objects are arranged along a tooth row at intervals. In this structure, a distance landmark in the depth direction is formed with an X-ray transmissive material. In this case, gains are searched which sharpens, with less blur, the boundary between the non-transmissive portion and the transmissive portion.

(Look-Up Table)

As described above, in the present embodiment, the focus-optimizing gains at respective positions (distances) in each of the depth directions intersecting a tooth row at each position thereof are stored in a predetermined area of the image memory 54 in the form of a look-up table LUT. When the look-up table LUT is available in this way, an arbitrary section along a tooth row can be subjected to image reconstruction under the degree of freedom given by the look-up table LUT.

By the way, the positions subjected to the foregoing preliminary gain measurement are defined as distances from the standard section along each of the linear lines connecting the X-ray tube and the detector during a scan, that is, along each of the depth directions during the scan. Hence, in order to produce the look-up table LUT adapted to a three-dimensional voxel space, it is sufficient to interpolate the gains at sampling points residing in the voxel space by using the known gains residing surround each sampling point (i.e., calibration). As a result, as shown in FIG. 8, in the horseshoe-shaped three-dimensional voxel based on the predetermined distance range R1 extending along the horseshoe-shaped tooth row, the gains are set, for example, at equal intervals in the same horseshoe-shaped section along the XY plane.

Though being described, the amounts of the gains are the same in the Z-axis direction (longitudinal direction) at each of the sampling positions (for example, a position of (N−1, S−D)), whereby it is possible to omit the calculation for obtaining the gains in the longitudinal direction. Thus, the look-up table LUT has information showing correspondence relations between the positions shown in FIG. 8 (i.e., positions defined by distances from the standard section) and gains at the respective positions.

Additionally, as to the look-up table LUT, it is significant, from a viewpoint of compatibility between image quality and calculation time, to decide the gains at optimum-number and detailed (fine-pitch) sampling points in what way. In principle, it is preferred to have the gains at sampling points set as finely as possible and to use the gains to perform sectional image reconstruction in two steps. In the first step, relatively roughly set gains are used to reconstruct a panoramic image along the standard section, so that the whole tooth row can be observed. Then, in the second step, a region of interest is for example manually set in this whole panoramic image and a panoramic image of the region of interest reconstructed using previously-set and finer gains. Thus the gains can be set based on more accurate interpolation calculation, and, after the overall observation, the local region can be observed on the high-accuracy gains.

Incidentally, even if the two-step reconstruction technique is employed, it is significant in the first step to obtain a panoramic image (a tooth-row overall image) at a more appropriate sectional position. The reason is that portions such as a lesion should be grasped from the beginning to prevent an oversight in the observation. For this reason, it is essential to specify a tooth-row section (the standard section in the present embodiment) which agrees with the shape and size of each patient's tooth row as much as possible.

(Speed Curve)

How to reconstruct a sectional image along a horseshoe-shaped tooth row using the foregoing gains will now be detailed. The basic concept for that is expressed by a speed curve shown in FIG. 9.

In FIG. 9, the abscissa axis denotes the frame numbers of frame data (for example, 1-4096), while the ordinate axis denotes positions where frame data are added in a memory space. A curve CA shows a speed curve produced in the memory image by dotting mapping positions of a reconstructed panoramic image versus the numbers of the frame data outputted from the detector 32 and used to reconstruct the image of a section specified as the standard section. This speed curve is thus designated as a standard pattern curve.

As understood from this graph CA, the graph in the standard section gives different gradients (that is, gains) to the side parts and front part of a tooth row, where the gradient for each side part is approximately −1.5 and that for the front part is approximately −0.657.

This standard pattern curve is preset, but may not provide best focus to acquisition positions desired in patients' tooth rows, because of individual differences in the tooth form and irregularities in the desired acquisition positions. For example, for obtaining a best-focused image of a patient's tooth row, it is best to acquire frame data as the speed is precisely changed depending on positions to be scanned, as shown by a curve CB in FIG. 9. However such scanning control is extremely complicated. In the present embodiment, in place of such a complicated scanning control, the amount of synthesizing acquired frame data (that is, the gain) is adjusted. This adjustment is performed on the foregoing speed curve. The synthesis amount for frame data is adjusted as a post process so as to be identical to panoramic image reconstruction where the actual acquisition speed is changed along a specified section specified by a desired curve as shown by the curve CB.

(Basic Concept of Focus Optimization)

As shown in FIG. 10, a panoramic image (base image) taken along a standard section along a tooth row, which will be prepared as a default by the apparatus in response to an interpreter's specification or selection, is basically used. That is, the interpreter uses this panoramic image to understand the overall tooth row. While observing this panoramic image, the interpreter locally specifies on the image a region of interest ROI (hereinafter this region is called "ROI") to which the interpreter desires more focusing (i.e., focus optimization). FIG. 10 shows two ROIs (ROI1 and ROI2) to be specified in such a way.

ROI1 specifies a small region which covers only a part limited in the x- and y-axes but desired to be observed actually. This ROI1 can also be set to a size which is nearly equal to that of an X-ray film used by the conventional intraoral X-ray imaging. In this intraoral imaging, side teeth are imaged using an X-ray film which appropriately covers the teeth. The present embodiment also considers this fact. Thus it is preferable that the ROI1, which is set to cover the side teeth well, is made to rotate (or tilt) the section sectioned by the ROI1 from the plane of the panoramic image which is in parallel with the x- and y-axes. Images of various sections viewed in various directions and angles, but having the size of this small region, are subjected to the process for the focus optimization as will be detailed. Such various sections include a parallel moved section, a tilted (rotated) section, a section produced by the parallel movement and the tilt (rotation) in an appropriately combined manner, and a curved section of which curvature agrees with the curved shape of each tooth.

In contrast, the ROI2 is an example specified when it is desired to focus-optimize the whole tooth row, so this ROI2 is larger in its size. In any case, specifying the ROI in this way results in a limitation of a region to be processed. Hence it is possible to reduce the amount of calculation necessary for a focus optimization process, thereby shortening the processing time.

When specifying the ROI(s) (ROI1, ROI2) on the base image, it is preferable to limit the y-axial (longitudinal) range of the ROI. The reason is that it is possible to exclude from the focus-optimizing calculation data which reside in the longitudinal region as data which does not need the optimization. This also reduces the calculation amount and raises the calculation speed.

After specifying the ROI, various sections having the size defined by the ROI are specified in an interactive manner. The apparatus performs the focus optimization with respect to only the specified sections. This optimization process is carried out automatically in response to an operator's command to indicate what section should be specified. Hence, a focus-optimized local sectional image that corresponds to the ROI can be rendered by the monitor 60, which image is thus for more detailed observation.

It is still preferred that the focus-optimized ROI image, that is, the local sectional image, is displayed by the monitor 60 in such a manner that uncomfortable feeling against habituation which has been taught by the conventional intraoral imaging using the X-ray film is alleviated. To be practical, it is convenient to display such a local sectional so as to make its lateral and longitudinal sizes agree with the actual distances.

(Outline of Focus Optimization)

The process for this focus optimization is executed by the image processor 56 as shown in FIG. 11.

In response to reception of a command for the focus optimization, the image processor 56 reads the speed curve CA for the standard section, and makes reference to the read-out speed curve CA and a specified ROI to designate a frame data FDc located at the center in the lateral direction of the ROI (the time sequential direction along which the frame data align) as shown in FIG. 12 (step A1). Then the image processor 56 designates, as pictorially shown in FIG. 12, a plurality of frame data FDb'-FDe' covering all the area of the ROI from the speed curve CA (step A2). In this step, because the detector 32 has an effective width which can be used, it is preferred to add, to both sides of a set of frame data FDb'-FDe', frame data FDb and FDe corresponding to the effective width.

Then, the image processor 56 adds (reconstructs) the frame data FDb-FDe designated according to the speed curve CA for the standard section (step A3) in a synthesis manner. Specifically, these frame data FDb-FDe are mapped to the respective mapping positions in the ROI (the longitudinal positions in FIG. 12) based on the speed curve CA (refer to directions P1 and P2 showing the mapping process). In this mapping step, the pixel value at the center of each frame data is set to zero, so that an offset is excluded from the synthesizing addition. Incidentally, the mapping positions are actually two-dimensional, but, to make it easier to understand, the one-dimensional positions are adopted in the present description.

The mapping process allows a plurality of frame data to be superposed at each of the mapping positions (i.e., pixel positions), so that those pixel values are added on one another. Thus the pixel values can be calculated at the respective mapping positions, providing a partial sectional image (that is, an image showing part of the panoramic image taken along the standard section). As a result, the individual pixels, which compose the ROI, provide contrasting densities which depend on the gradients of the speed curve CA, that is, the gains, providing in a panoramic image depicting the structure of a tooth row.

Then the image processor 56 determines in an interactive manner whether or not information indicative of the position subjected to the optimizing reconstruction is changed (step A4). In this case, the information includes positional and angular information of the area sectioned by the specified ROI in the depth direction. If the positional changes are desired, gains depending on the changed positional information are read out of the look-up table LUT (step A5). The read-out gains are integrated toward the central pixel of the frame data to figure out a corrected speed curve CB (step A6).

Since the size of the ROI is fixed, the number of frames of frame data necessary for the reconstruction at the new position differs from the previous one. Hence, in order to enable the central frame data FDc designated at step A1 to be located again at the center of a region defined by a changed position, frame data necessary for reconstructing the new region are designated (step A7). As a modification, in order to make the size of the new region at the changed position the same as that of the first ROI, the number of frame data may be increased or decreased depending on the changed position.

After the preparation, the image processor 56 uses the speed curve CB obtained at step A6 and the plurality of frame data designated at step A7 to reconstruct the sectional image of the changed partial region in the same way as that at step A3 (step A8). The speed curve CB used for this reconstruction can be exemplified as shown by a chain double-dashed line in FIG. 12.

Further, the pixel values of the reconstructed sectional image are multiplied respectively by coefficients proportional or inversely proportional to the gains (corresponding to the sectional position) used for the reconstruction (step A9). This process is to reduce differences in the apparent contrasting densities among the images, so that even if images are changed, it is easier to observe the images and interpretation work becomes easier.

The sectional image produced as above is not part of the panoramic image itself along the standard section, but is the image of a partial section of which position is changed based on the ROI specified on that panoramic image. When this partial sectional image meets an interpreter's demand, both the partial sectional image data and information indicating the position thereof (information indicating the position in the depth direction and the angle) are stored (steps A10 and A11). In contrast, if the produced partial sectional image is not desired by the interpreter, the processing is returned to step A4 (step A10).

Referring to FIGS. 13-18, exemplary processes for the gain preliminary measurement, panoramic imaging, and image interpretation, which are executed by the panoramic imaging apparatus 1 according to the present embodiment will now be described.

(Gain Preliminary Measurement)

First of all, referring to FIG. 13, the gain preliminary measurement (the gain calibration in cases where the gains are already set) will now be described.

As described, the gain means how much degree frame data should be synthesized on one another for the synthesizing addition. The gain that provides an optimized focus position with less blur depends on a position (distance) in each of the depth directions intersecting a row of teeth. As the gain becomes smaller, the focused position becomes closer to the X-ray tube 31 in each depth direction, while the gain becomes larger, the focused position becomes farther away from the X-ray tube 31 in each depth direction.

To preliminarily set the gains and possess the set gains, the controller 57 in the control/calculation unit 12 performs a process outlined in FIG. 13, interactively with an operator.

For preliminary measuring the gains, the phantom FT is fixedly located at the chinrest 25 (refer to FIG. 1) instead of a patient. The fixed position of the phantom FT corresponds to a spatial position decided as the standard position where the tooth row of a patient P is located when the actual imaging is carried out as detailed later. The phantom FT used in this embodiment is the one described with FIG. 5 or FIG. 7. The height of the up-and-down unit 23 is adjusted in conformity with the Z-axial directional position of the phantom FT to allow the collimated X-ray from the X-ray tube to be radiated onto the phantom FT.

After fixedly setting the phantom FT, the control/calculation unit 12 receives information showing X-ray radiating conditions (tube voltage, tube current, scan time and others) from the operator (step S1).

After this condition setting, the rotation unit 24 (that is, the pair of the X-ray tube 31 and the detector 32) is moved (scanned) around the phantom FT along the XY plane in response to an operator's command. During this movement, the X-ray tube 31 radiates X-rays and the detector 32 detects transmitted X-rays at a high frame rate, so that the frame data are acquired (step S2). By way of example, the acquired frame data are outputted from the detector 32 at a high frame rate of 300 fps, and those frame rates are sent to the image memory 54 for storage therein via the buffer memory 53.

The controller 57 then commands the image processor 56 to use the acquired frame data to reconstruct a panoramic image of a tooth-row section (predetermined section) located at a predetermined spatial position (step S3). This predetermined section is along a central line ST in a patient's standard tooth row, as shown in FIG. 14, where the standard tooth row is a standard-size horseshoe-shaped tooth row contour along which the respective teeth align. The predetermined section is made to agree with a standard section among a plurality of standard sections prepared in a selectable manner in the later-described actual imaging.

The gain G at each position Pn along this predetermined section (that is, the position at which each depth direction Dpd and the standard section intersects with each other) is previously decided as a gradient given by the speed curve for the standard section, which speed curve is shown by the foregoing curve CA in FIG. 9. The image processor 56 reads, from the image memory 54, all the acquired frame data, and adds those frame data to mapping positions decided by the speed curve CA (i.e., synthesizing addition). Hence the panoramic image of the standard section is reconstructed.

The controller 57 then enables the monitor 60 to display the panoramic image reconstructed along the standard section (step S4). An example of this display is shown in FIG. 15. As shown, the panoramic image of the standard section provides images of five measurement plates consisting of a left end measurement plate 72L, a left intermediate measurement plate 72LC, a central measurement plate 72C, a right intermediate measurement plate 72RC, and a right end measurement 72R, which are tilted at an oblique angle of 45 degrees on the phantom FT. The image of each measurement plate provides the plurality of phantom members 74 depicted therein. Though only pictorial depiction is allowed in the figure, the phantom members 74 provide various blurring states, in which one or more phantom members 74 residing at a central spatial region of the measurement plate in the plate longitudinal direction (along the depth direction) provide the least blur, that is, being best focused, which central spatial region corresponds to the standard section.

In the present embodiment, as a matter of convenience for gain preliminary measurement, the region of each measurement plate is roughly divided into five regions consisting of an outermost region Rotm, an outer region Rot, a central region Rc, an inner region Rin, and an innermost region Rinm (refer to FIG. 15). The standard section is set to belong to the central region. In the case of the foregoing phantom FT1 shown in FIG. 5, the predetermined distance range R1 projected onto the base 71 (the XY plane), which is for example 20 mm, is divided into five regions. In this range R1, the tooth row section can be moved freely for diagnosis in each of the depth directions.

In the example, the two regions, that is, two sections can be set respectively before and after the standard section in the depth directions, whereby in total five types sections including the standard section can be measured. FIG. 14 pictorially exemplifies this setting, in which the outermost virtual line expresses an outermost section OTM, the next inner virtual line expresses an outer section OT, the next inner virtual line expresses the standard section ST, the next inner virtual line expresses an inner section IN, and the innermost virtual line expresses an innermost section INM, respectively. An interval between adjacent sections in the depth direction is set to 4 mm, for instance.

The reason why the depth-directional region is roughly divided into five regions comes from the fact that it is sufficient to secure a range of about 20 mm in which the section can be changed positionally in the depth direction of the tooth row. As will be detailed later, the gains are interpolated finally. Accordingly a compromise between the calculation amount and the calculation time gives a conclusion that it is enough that, in the preliminary measurement stage, the gain basic data are acquired at five points (i.e., the gains in the five regions).

While viewing and observing this panoramic image, the operator interactively sets gains at sections (positions) other than the standard sections in each of the depth directions. Practically, is the operator selects the first measurement plate 72 of the phantom FT to display an enlarged image of the measurement plate 72 (step S5; refer to FIG. 16). This enlargement display makes the plural phantom members 74 on the measurement plate 72 easier to see, whereby the gain can be set accurately as much as possible. This enlargement display will now be explained using the central measurement plate 72C. The plural measurement plates can be subjected to the enlargement display at any order.

The controller 57 receives information in relation to operations of the operator who visually observes the enlarged-displayed central measurement plate 72C and, in replay to receiving the information, specifies regions other than the central region of this central measurement plate 72C in its plate longitudinal direction (step S6). In reply to the region specification, the controller 57 calculates the positions of the specified regions in each depth direction, and stores information indicative of the calculated positional coordinates (step S7). Through the steps S6 and S7, for example, the outermost region Rotm of the central measurement plate 72C, that is, the position of the outermost section OTM in the depth direction along which the central measurement plate 72C are arranged, is first specified.

In reply to the operational information from the operator, the controller 57 determines whether or not the one or more phantom members 74 residing in the outermost region Rotm observed now have no blur (including almost no blur or the least blur state) (step S8). That is, it is determined whether or not the focus is best (i.e., whether or not the focus-optimized state is realized). Each phantom member 74 is a round lead ball. Thus, when the lead ball image is round and clear in its contour, the operator can decide that the focus-optimized state is realized, so is the operator presses a button (not shown) on the monitor screen, which button is previously set to show a focus-optimized state. In contrast, the operator determines that there is realized no focus-optimized state, the operator presses a not-shown button on the monitor screen, which button is previously set to show a non-focus-optimized state. Then the operator operates buttons for changing (increasing or decreasing) the gain, in which such buttons will appear on the monitor screen responsively to pressing the button showing non-focus-optimized state (step S9).

When changing the gain, the changed gain is used to reconstruct the changed section, that is, a panoramic image at the changed position in the depth direction (step S10). In this process, only the image of the central measurement plate 72C, which is now displayed in the enlarged manner (the image region thereof is specified), is reconstructed, thus shortening the calculation time. This newly reconstructed panoramic image is again displayed as an enlarged image (step S11).

In the controller 57, the processing is then shifted to step S8, where, as described above, it is determined whether or not there is a blur on the image of the phantom member 74 residing the outermost region Rotm of the central measurement plate 72C. If the determination results in NO, there is still a room for optimizing the focus. Thus, the controller 57 changes the gain in reply to an operator's command so that an updated panoramic image is reconstructed and displayed (steps S9-S11). In this way, the gain is changed in the trial and error manner to obtain a panoramic image with no or less blur (YES at step S8). When this panoramic image is obtained, the operator is able to recognize that the current gain is optimum to obtain the best focus at the outermost section OTM in the depth direction along the central measurement plate 72C. The controller 57 stores this gain, as a focus-optimizing gain, into the image memory 54 in response to an operator's command (step S12).

The controller 57 then shifts its processing to step S13, where it is determined whether or not the gain measurement has ended as to all the longitudinal regions of the current measurement plate 72. When this determination shows NO (NO at step S13), the controller 57 returns to step S6 to repeat the foregoing processing at another region. Thus, for example, it is possible to measure the focus-optimizing gains at the position of the outermost section OT, which corresponds to the outer region Rot in the depth direction along the central measurement plate 72C.

In contrast, when the determination at step S13 is YES, the controller 57 further determines whether or not the foregoing measurement of the focus-optimizing gain has been ended as to all the measurement plates (step S14). When the determination is NO at this step, it is understood that there remains a measurement plate to be measured. Thus the controller 57 returns its processing to step S5 to repeat the foregoing processes to another measurement plate, for example, the right intermediate measurement plate 72RC. Thus, the gains at the sections corresponding to the regions other than the central regions Rc in the longitudinal direction of the newly specified measurement plate. On the other hand, when the determination at step S14 is YES, the gains are obtained as reference data at the positions shown by a total of 25 points (refer to the black circles shown in FIG. 17) using all the five measurement plates 72. The 25 points are composed of a total of 20 points residing in the outermost, outer, inner, and innermost regions of the respective plates and a total of 5 points along the reference plane.

The controller 57 then applies a properly selected interpolation technique to the reference gains at the total of 25 points mapped in a two-dimensional region (refer to a shaded area in FIG. 17), which has, as a width, the predetermined distance range R1 and extends along the standard section ST in the XY plane. By this interpolation, gain data are calculated at positions that interpolate the space among the spatial positions providing the reference data (refer to the positions of x-indications in FIG. 17: step S15). When this interpolation is completed, the gains at the respective points (the positions shown by both the black circles and the x-indications) in the horseshoe-shaped two-dimensional region are stored in the look-up table LUT of the image memory 54 (step 516). The look-up table LUT thus provides the values of the gains at the positions intersecting the standard section ST, the positions dotted along the depth direction passing each of the intersections, and the interpolated positions.

The gain values along the up-and-down direction (the Z-axis direction) perpendicular to the two-dimensional region are the same, position by position, in this region. Thus the two-dimensional look-up table LUT is synonymous with a look-up table for the three-dimensional gains.

Through the series of steps shown in FIG. 13, the gains are preliminarily measured at the respective positions in the three-dimensional region having the horseshoe-shaped two-dimensional region defined by the predetermined distance R1 in the depth direction centering at the standard section ST. It is sufficient that this gain preliminary measurement is carried out when being shipped from the factory or installed at the site. It may be possible to carry out the measurement as calibration every time the apparatus is activated, not limited to the time for the regular or irregular maintenance. In the calibration, the gain data of the look-up table LUT are updated to new data.

The more the number of measurement plates of the phantom for the preliminary measurement and calibration, the more detailed the gain data measured as references. However, the operator's operational burden is also increased when the number of measurement plates increases. Thus, the number of measurement plates and the positions where the measurement plates are located may be decided in consideration of factors such as the operational burden and precision required for the gains.

(Imaging)

Referring to FIG. 18, the imaging, that is, actual data acquisition, will now be described.

For imaging, an operator inputs to the control/calculation unit 12 patient information including a patient ID, patient's name, and imaging date (step S21). In response to this input, the controller 57 records the patient information in a predetermined region at the image memory, and uses, as key information, for example the patient ID to relate, to the patient, frame data to be acquired from now.

Then, a person to be examined (patient) P is positioned as illustrated in FIG. 1. The operator adjusts the height of the up-and-down unit 13, the mouth cavity portion of the person to be examined P is positioned at the predetermined imaging position using the chinrest 25 and the headrest 28, with the mouthpiece 26 bitten by the person. This positioning may be performed before inputting the patient information or may be performed after setting X-ray radiating conditions later described.

The controller 57 sets an actually imaged standard section on the basis of operational information from the operator in an interactive manner (step S22). This standard section is set by selecting a desired one among several standard sections previously prepared by the apparatus. This setting will be detailed later.

Further, the control 57 uses operational information from the operator to set X-ray radiating conditions (such as an X-ray tube voltage, an X-ray tube current, a scan time and a scan orbit) similarly to those for the foregoing gain preliminary measurement (step S23).

After this preparation, the controller 57 responds to a command from the operator by moving (scanning) the rotation unit 24 (, namely the pair of the X-ray tube 31 and the detector 32) in the XY plane around the mouth cavity portion of the person P being examined, and, during the movement, enables the X-ray tube 31 to radiate the X-rays and the detector 32 to detect transmitted X-rays at high-speed frames. Thus the frame data are acquired (step S24). That is, the frame data are outputted from the detector 32 at a fast frame rate of 300 fps, for instance, and transferred to the image memory 54 via the buffer memory 53, with the frame data stored in the image memory 54.

If necessary, it may be possible to receive image data acquired by an intraoral X-ray imaging apparatus placed differently from the present panoramic imaging apparatus and store those image data in the memory device before or after acquiring the foregoing frame data.

When this scan is completed, the examined person P is released from the panoramic imaging apparatus.

(Interpretation (Observation))

When the acquisition of the frame data has been finished, a doctor is able to interpret panoramic images, as a post process, using the acquired frame data.

A series of processes for the interpretation, carried out by the controller 57 are shown in flowcharts of FIGS. 19-20, and operational examples of the interpretation are shown in FIGS. 21-25.

As shown in FIG. 19, the controller 57 responds to a command from the operator to receive input about a patient, that is, an object being interpreted (step S31). For example, information designating an object to be interpreted, such as an patient ID and an imaging date and time, is inputted, the controller 57 notifies the image processor 56 of the reception of the information. The image processor 56 reads out frame data of an examined person P designated by the inputted information from the image memory 56 and stored them into the work area of the image processor 56 (step S32).

The controller 57 then commands the image processor 56 to reconstruct a panoramic image of a standard section and display the reconstructed panoramic image on the monitor 60 (steps S33 and S34). In reply to this, as pictorially shown in FIG. 21, the panoramic image of the standard section in the tooth row of the examined person P is displayed by the monitor 60. This panoramic image depicts a sectional structure along the standard section, which is an X-ray transmission image.

These processes are the same as those explained with the foregoing gain preliminary measurement (refer to FIG. 13, steps S3 and S4), and correspond to a preparatory step for the interpretation work.

The controller 57 then waits, during which the controller determines whether or not information showing a ROI to be set on the panoramic image of the standard section is given by an operation, namely a doctor who interprets images (step S35). As stated already, this ROI becomes information locally specifying a region of interest on the panoramic image of the standard section and is used when the doctor desires the local region to be observed in different angle and/or sectional views. In the present embodiment, this ROI can be set as a small rectangular region whose longitudinal and lateral dimensions are free, but smaller than those of the panoramic image.

How to set the ROI is exemplified in FIG. 22. A ROI, ROI1, shown in FIG. 22(A) is a region of interest specified when it is desired that a specific tooth among the upper tooth row is optimum-focused solely, while a ROI shown in FIG. 22(B) is a region of interest specified when it is desired that a plurality of teeth among the upper and lower tooth rows are optimum-focused as a group. In any case, it is desired that, for sake of shortening the calculation time for image processing later described, the longitudinal (Z-axis) size of the local region being specified is limited to a necessity minimum as much as possible.

Concerning the size of the ROI, as stated, it is also possible to set to the same value as that of an X-ray film used by the conventional intraoral imaging. It is possible to rotate (tilt) the section specified by the ROI from the plate given by the panoramic image so that the ROI contains side teeth properly.

When the determination at step S35 is YES, the specified ROI information is used to display the ROI on the panoramic image in a superposition manner (step S36). Assume that the superposed display state is shown like FIG. 22(A). The controller 57 examines the displayed ROI as to its position and size in response to operational information from the operator (step S37), and, according to necessity, obtains information for changing the position and/or size to again display a changed ROI in the superposition manner (step S38).

When the ROI specification is finished, the controller 57 specifies a range of the frame numbers of the frame data (i.e., a range of the frame data) that provide the pixels specified by the ROI set on the panoramic image (step S39). This specification is for a process for observing a section having the size of the region of interest given by the ROI, as another section tilted (rotated) from the section specified by the region of interest. That is, as stated with FIG. 11, by making reference to the speed curve for the standard section, the range of the frame numbers corresponding to the lateral size (the X- (Y-) axis directional size) of the specified ROI is decided. With regard to the longitudinal direction (i.e., the Z-axis direction) of the panoramic image, the range is cut according to the longitudinal size of the specified ROI, as stated.

Since the amount of the effective width of the detector 32 is known previously, the controller 57 designates the numbers of finally used frame data that covers this effective width (step S40).

The controller 57 then performs, in various ways, the processing for observing the section of the region of interest specified on the ROI (steps S41-S54).

Specifically, using an operational command from the operator, it is first determined whether or not the image itself of the region of interest on the panoramic image of the standard section should be displayed in an enlargement manner (step S41). When the enlargement display is commanded, the image is enlarged at a desired enlargement factor and displayed on the panoramic image in a superposition manner (step S42). This enlargement/superposition display is exemplified in FIG. 23. The enlargement factor may be a default value or may be a value arbitrarily selected from a given range of values.

The controller 57 further responds to operational commands from the doctor who is in charge of interpreting images, such that the section having the size of the region of interest on the panoramic image of the standard section is moved in parallel in the depth direction to observe images of parallel-moved sections (steps S43-S46). FIG. 24 explains the concept for this parallel movement of sections. Displayed currently on the monitor is the image of a partial section along the previously selected standard section. Hence the parallel movement of this displayed image gives sectional views at positions shifted before or after the standard section. A range in which this parallel movement is allowable depends on the foregoing predetermined distance range R1 (for example, 20 mm: refer to FIG. 5). In other words, if the movement is carried out within this predetermined distance range R1, the gains, which have already been measured within the range, can be used to reconstruct sectional images as post processes. Thus, in cases where a lesion is found on the image of the standard section, moving part of this section in parallel gives information in relation to a disease state and a gum state in the tooth thickness direction.

It is thus determined using the operational information whether or not it is required to observe a parallel-moved section (step S43). If this is required, the controller obtains information showing that how much of distance and in which way the section should be moved by how should be moved (step S44). In this process, when the movement distance=0 is given, it is meant that part of the section itself that provides the basic panoramic image is designated.

Then, a new section depending on the movement information (for example, a parallel backward movement of 4 mm), that is, a new section moved in parallel, is specified. From the look-up table LUT, gains G uniquely decided at the position of this new section are read out, and the frame data to be targeted is subjected to synthesizing addition, as explained, using the read-out gains. This gives a reconstructed image of the local section decided in size by the ROI and moved in parallel by a desired distance in the depth direction (step S45). As a result, a focus-optimized image with no or less blurs can be provided.

The image thus reconstructed is then displayed in a predetermined or desired mode (step S46). The predetermined-mode display is a display technique provided by default, which allows the reconstructed image is displayed at a predetermined position of the currently displaced basic panoramic image, as part thereof, in a superposition manner. On the other hand, the desired-mode display, which will be described later, allows the interpretation doctor to select how to display from previously prepared display modes, according to need for the interpretation.

Moreover, when the determination at step S43 is NO (i.e., the parallel movement is not necessary), the controller 57 determines interactively whether or not it is necessary for a tilt (rotation) (step S42). That is, the controller 57 responds to operational information from the interpretation doctor by interactively performing the processing for the tilt (rotation). Concretely, the section having the size of the region of interest (specified by the ROI) in the basic panoramic image of the standard section is rotated about the depth direction, and an image along this tilted (rotated) section is observed (steps S48-S50).

Performing the processing for this tilt (rotation) means to obliquely change the projection direction by an amount of tilt (rotation) of a section. The tilt (rotation) angle is usually a range from several degrees to several dozen degrees.

FIG. 25 explains the concept of tilting (rotating) the section given by the ROI. The tilt of a section can be defined by a central axis position, a tilt direction, and a tilt angle. Thus, as the "tilt" of the section can be said as "rotation (turn)" around the central axis of the section, the term "tilt" may be representatively used in the following. The figures shown in FIG. 25(A)-(C) show that a section is tilted by a desired angle about an axis located at a central position, an upper end position, and a lower end position in the longitudinal (Z-axis) direction of the section specified by the ROI. In addition, the figures shown in FIG. 25(D)-(F) show that a section is tilted by a desired angle about an axis located at a central position, a left end position, and a right end position in the lateral (X-axis) direction of the section specified by the ROI. The limits to which the local section specified by the ROI can be tilted should be within a predetermined range in the depth direction, in which the gains are preliminary set in the predetermined range. This gives a meaning to the interpretation.

Thus, the determination at step S47 shows the tilt display, the controller 57 obtains operational information indicating a central axis center, a tilt direction, and a tilt angel (step S48). The controller 57 then decides a new section depending on the tilt angle, that is, the position of the tilted section, reads out, from the look-up table LUT, gains G uniquely decided on the position of this new section, designates frame data contributing to reconstruction of the is image of this section, and performs, as described, synthesizing addition with the designated frame data and the read-out gains G. This enables the ROI-specifying tilted local section to be reconstructed as an image (step S49). The tilt information is for example bits of information specifying a clockwise tilt of the ROI-specifying local section about the central axis in the longitudinal direction thereof by an amount of 10 degrees.

The reconstructed image is displayed in a predetermined or desired manner (step S50). How to display this image is similar to the process at step S46.

Moreover, when it is found that the determination at step S47 shows NO (i.e., the tilt (rotation) is not required), the controller 57 then shifts to determination about whether or not it is required to interactively perform "parallel movement+tilt (rotation)" (step S51). Practically, the controller 57 interactively replies to operational information from the interpretation doctor such that the section having the size of the region of interest ROI-specifying in the basic panoramic image along the standard section is moved in parallel in the depth direction and tilted (rotated) with regard to the depth direction, and the moved and tilted section is subjected to the processing for observing the image thereof (steps S52-S54). In this case, the technique to decide the position of the moved and tilted section may have a process order in which the parallel movement first comes, preceding the tilt (rotation), and vice versa in the process order. Thus, information specifying the two types of movement (parallel movement and tilt (rotation)) for the local section specified by the ROI is inputted, the section is focus-optimized, and the focus-optimized sectional image is displayed.

In displaying on the monitor 60 this focus-optimized ROI image, that is, the local sectional image, it is also possible to the longitudinal and lateral sizes of this local image are made to be equal to actual distances.

When the determination at step S51 is sill NO, the processing is shifted to step S55. At this step S55, it is determined by the controller 57 whether or not a command for ending the interpretation work has been issued from the interpretation doctor. When it is determined that the interpretation should be continued (NO at this step), the processing is returned to the foregoing step S35 to repeat the foregoing processes.

In contrast, it is determined the end of the interpretation (YES), the controller 57 then determines whether or not the data should be stored in a recording medium in an interactive manner (step S56). In this case, the data includes the data of the interpreted images (including the basic panoramic image and the sectional image specified by the ROI) and the related information (patient information). When the determination is YES, that is, the data storage is desired, the data is stored in the image memory 54 (step S57). Furthermore, the controller 57 uses a command from the interpretation doctor to determine whether or not it is desired that the data are transferred to an external DICOM server (step S58). If the determination is TES, that is, the data transfer is desired, the data is subjected to conversion to DICOM specifications, before being transferred to an external communication line via the communication interface 62. The DICOM server meets the DICOM (Digital Imaging and Communications in Medicine) standard.

The controller 57 then use operational information from the interpretation doctor to determine whether or not the image data which have been processed are desired to be printed (step S60). When the determination is YES, that is, the printing is necessary, a printing command is issued to the printer 64 for printing the image data (step S61).

(Selection Process of Standard Section)

Referring to FIGS. 26 and 27, the selection process of the standard section (step S22) needed in the foregoing imaging will now be supplemented.

The controller 57 first depicts, on the monitor 60, as an initial screen, a pictorial figure Tst of a standard tooth row and a curved line SC1 superposed on the standard tooth row Tst, as shown in FIG. 27 (FIG. 26, step S22$_1$).

The curved line SC1 indicates a first standard section (corresponding to the forgoing standard section) which is set along the standard tooth row. This first standard section SC1 is a section having a standard size decided based on a standard tooth row Tst sampled statistically from a large number of people. Accordingly, as long as the size and position of respective teeth of a patient P to be examined agree with those of the standard tooth row Tst, the first standard section SC1 is enough for imaging. That is, by making the X-ray tube 31 and the detector 32 move (rotate) so that the X-rays radiated from the X-ray tube 31 are always focused on the first standard section SC1, the first standard section SC1 itself becomes an optimum-focused section, whereby the image of this section is projected as a basic panoramic image. As described, this projected image is acquired as frame data (line data) by the detector 32 at a fast speed. In such a case, there is no necessity of selecting another section as the basic section.

However, it should be noted that the patient P is an adult or a child and the tooth-row shapes (teeth forms) have individual differences. In such cases, it is very often that the first standard section SC1 is different from that of the patient. On the other hand, it is preferable that a panoramic image serving as the base image is made to agree in its shape with an actually imaged patient P as much as possible from the beginning, thus providing more reliable image information, thus providing diagnosis and interpretation with higher accuracy. In addition, a local region for interpretation, which is carried out based on the base image, that is, the panoramic image of a whole tooth row, will be specified accurately. For this reason, the standard section is selected.

The controller 57 makes an inquiry to the operator about whether or not the operator selects the first section SC1, which is now displayed on the initial screen (step S22$_2$). In consideration of the size of the tooth form and the shape of the tooth row of the patient P, the operator determines whether or not the standard section should be changed to another one. Other selectable standard sections, the second and third standard sections SC2 and SC3 are prepared (refer to FIG. 27). The second standard sections SC2 is horseshoe-shaped and has a curvature less than the first standard section SC1. The third standard section SC3 is also horseshoe-shaped, but has a curvature larger than the first standard section SC1.

Thus, when the operator considers the size and shape of the tooth row of the patient P and determines that the first standard section SC1 is still enough for the basic image, the operator operates to establish the selection of the first standard section SC1 (step S22$_3$). In contrast, when it is determined that the first standard section SC1 has excess and deficiency, the second or third standard section SC2 or SC3 is selected (step S224). To confirm the selected section SC2 (SC3), the monitor screen shown in FIG. 27 renders the selected on in a different color (step S22$_5$).

In this way, from the beginning, the standard section fit to the shape and size of the tooth row of each patient P as much as possible is selected, so that a panoramic image along this selected standard section is produced as the base image.

(Selection of Display Mode)

Furthermore, referring to FIGS. 28-31, selecting a display mode for the foregoing interpretation will now be detailed (steps S46, S50 and 554).

Image data to be displayed here are the data of a panoramic image first acquired as the base image, an original image of a local region specified by a ROI on the whole panoramic image (i.e., part of the base image), and a focus-optimized image of the local region specified by the ROI (i.e., an image of a parallel moved, tilted, and/or parallel-moved and tilted section: refer to steps S45, S49 and S53).

For this display, the controller 57 first uses operational information from an interpretation doctor so as to determine whether or not the whole panoramic image and the focus-optimized image should be displayed in a divided manner (step S61). If this determination is YES, that is, the divided display is desired, the controller 57 enables both the panoramic image and the focus-optimized image to be displayed on the monitor 60 as shown in FIG. 29, for instance (step S62). In this example, the panoramic image Ppano is displayed in a lower part of the screen and the focus-optimized image Popt is displayed in an upper part of the screen. On the panoramic image Ppano, for example, a rectangular ROI is superposed which specifies the local region.

Then, as waiting timing, the controller 57 determines whether or not an operation for ending the display has been performed (step S63).

On the other hand, no divided display is carried out (NO at step S61), the controller 57 determines based on operational information as to whether or not the superposition display is required (step S64). If this determination shows that the superposition display is required, the controller determines on operational information as to whether or not at least one of the original image and the focus-optimizes image is required to be enlarged for the display. When such an enlargement display is required, the processing for this display is executed (steps S65 and S66).

Then the controller 57 displays, on the monitor 60, the panoramic image Ppano on which the original image Pori and the focus-optimizes image Popt are superposed so as to be compared with each other, as shown in FIG. 30 (step S67). The processing is then shifted to step S63.

Further, when the determination at step S64 is NO, that is, no superposition display is required, the controller 57 determines whether or not the focus-optimized image is desired to be displayed alone (step S68). If the determination YES is issued at step S68, the controller 57 displays, on the monitor 60, only the focus-optimizes image, for example, as illustrated in FIG. 31 (step S69).

The images to be displayed are always accompanied with information indicating the sectional positions of the images. For example, as shown by reference P1 in FIGS. 29-31, the panoramic image Ppano is accompanied by positional information indicating the standard section, the original image Pori is accompanied by positional information indicting the ROI specified thereon, and the focus-optimized image Popt is accompanied by positional information indicating a local section providing the image Popt (that is, information about a position on the panoramic image, a distance from the standard section when being parallel moved, and/or an angle and a direction when being tilted (rotated)).

It is possible to select a desired display mode from various ones, so that the interpretation doctor can display interpreted results in an appropriate mode.

As described, according to the digital type of dental panoramic imaging apparatus according to the present embodiment, differently from the conventional, it is possible to provide panoramic images which fully meet demands from dentists.

Specifically, the same frame data acquired only one time can be used many times to reconstruct images of local sections to be diagnosed. The local sections can be moved in parallel and tilted (rotated) by changing projection directions. It is also possible for interpretation doctors to quantitatively specify a distance for the parallel movement and an angle for the tilt (rotation). In other words, the interpretation doctor observes the displayed panoramic image of the standard section and interactively moves a desired local section on the panoramic image for observation of teeth and gum-ridge displayed in the sectional image. It is thus possible to provide three-dimensional information about a lesion in teeth and the gum-ridge. In addition, the standard section providing the base image can be selected from the previously prepared plurality of standard sections. It is thus possible to select a standard section which is fit to an actually diagnosed patient's tooth row.

Though it is significant to set a best-optimized section to be imaged along a patient's tooth row, it is not required to be nervous about setting the section so much. That is, in the present embodiment, it is sufficient to select a standard section which seems to be best, from the plurality of sections prepared in advance. Using the frame data acquired by the imaging, as described, subsequent interpretation can be performed freely. This makes it possible to remarkably reduce an operator's burden in setting optimum sections, thus alleviating operational skill required to operators.

Thus, images of local sections to be specified on the whole panoramic image along the standard section subjected to the data acquisition at a moderate optimum and images of other sections whose spatial positions are three-dimensionally changed from the local section are always reconstructed into focus-optimized images with less blurs, with the use of the gains preliminary measured and stored. Accordingly, being less in the blur results in being rich in the structural information about the teeth and gum-ridge as well as higher in accuracy, reducing a burden to dentists in diagnosis.

In addition, the image of the section interactively specified by the ROI is displayed together with the positional information thereof. For example, the positional information shows that the section is moved in parallel rearward from the standard section by 5 mm or the section is tilted (rotated) by 20 degrees about the axis passing the longitudinal center such that the lower end of the section comes frontward. Thus the interpretation doctor is able to interpret the images, with having an understanding of distances within the inner structures of the teeth and the gum-ridge. Thus the interpretation doctor can consider individual differences of the teeth and tooth row and engage in free observation of the sections. That is, it is possible to meet doctor' demands, such as "wants to observe a portion located a little bit rearward or frontward," "wants to observe a section along an oblique tooth," and "wants to observe a section along the thickness direction of a tooth," which are difficult to perform by the conventional apparatus. Thus, lots of information effective for diagnosis can be obtained, contributing to improving the accuracy of the diagnosis.

In this way, using the frame data acquired once, rich internal structural information of a tooth row can be obtained easily, so that, differently from the conventional, in almost all situations, it is unnecessary to perform another imaging to compensate the panoramic images acquired by the present apparatus. Accordingly, time necessary for obtaining diagnosed results becomes shorter and work necessary for the diagnosis becomes less, improving a patient throughput and suppressing the amount of X-rays exposed to patients from increasing.

As to the computer 12, its functions in charge of postprocessing the panoramic images may be realized by adopting a further computer in a stand-alone or on-line structure.

Second Embodiment

Referring to FIGS. 32-38, a second embodiment of the panoramic imaging apparatus according to the present invention will now be described.

The panoramic imaging apparatus according to the present embodiment is characteristic of performing a process (contrast enhancement process) for enhancing the contrast of images of two-dimensional regions specified by ROIs, that is, images (original images) of local regions on the panoramic image produced at the foregoing step 39 (in FIG. 19); the contrast of enlarged original images subjected to enlargement display at step S42 (in FIG. 20); and the contrast of focus-optimized images to be displayed at steps S46, S50, and S54 (in FIG. 20). The other configurations and processes are the same or similar as or to those in the first embodiment. Hence, the identical components to those in the first embodiment are given the same reference numbers.

The contrast enhancement will not always be limited to the application to two-dimensional regions specified by ROIs, but may be applied to the entire panoramic image reconstructed at the standard section, as explained in the previous embodiment. However, the contrast enhancement process normally increases calculation load and reduces processing speed. When taking it account various factors including a reduction in the calculation load, an increase in the processing speed, and an actual interpretation in which it is sufficient to raise the contrast of necessary partial regions, it is desired to apply the contrast enhancement to two-dimensional regions specified by ROIs.

This contrast enhancement process can be executed by the image processor 56 or the controller 57. In the present embodiment, the image processor 56 is in charge of executing the contrast enhancement process.

It is now supposed that this contrast enhancement process is executed in the focus optimization and display of a local section subjected to parallel movement at steps S45-S46. In this case, the image processor 56 will execute the contrast enhancement process between the focus optimization process at step S45 and the display process at step S46. In the image memory 54, the data of a gray-scale two-dimensional digital image, which is a reconstructed local image whose focus has been optimized, are stored previously. This two-dimensional image is used as an original image to which the contrast enhancement process is applied.

FIG. 32 shows a flow of steps required for the contrast enhancement, which is executed by the image processor 56.

In summary, the processes of this contrast enhancement includes input of frame data (gray-scale image data) serving as an original image data (step S101); a preprocess called a density (pixel value) shift, which is applied to the original image data (step S102); a wavelet transform serving as multiresolution decomposition applied to the original image data subjected to the density shift (step S103); a weighting process applied to coefficients derived from this transform, which is for the contrast enhancement (step S104); an inverse wavelet transform serving as a reconstruction process, which is applied to the weighted coefficients (step S105); and display and storage of a contrast-enhanced image obtained by the inverse wavelet transform (step S106). Hereinafter, these processes will now be described in turn.

(Input of Original Image)

At first, the image processor 56 responds to an operator's command given from the operation device 58 so as to read, into its work, memory gray-scale digital image data (data of frames) to be subjected to the contrast enhancement process from the image memory 54 (step S101).

(Shift of Densities)

The image processor 56 then automatically executes a preprocess called a density shift on the read-in image data (step S102).

This density shift is a preprocess for shifting the densities (pixel values) of the whole image in the density gradation domain so that an average density of this image is located at the center of the density gradations (scale; in the present embodiment, the scale of gray levels). By performing this density shift, the dynamic range of an image display unit (the monitor 60) can be utilized fully and the original image to be processed can be subjected to the contrast enhancement in a proper manner. That is, it is possible to suppress the number of pixels which run off from the scale.

Now, for example, suppose that the original image has a density gradation of 8 bits (256 gradations) and this density is given by f(x, y). In this case, a value to be shifted, offset, is given by $$\text{offset} = 128 - (\text{a sum of all pixel values})/(\text{the number of all pixels}) \quad (1)$$
$$= 128 - \sum_{x=1}^{M}\sum_{y=1}^{M} f(x, y).$$

Thus, a density-shifted image $\hat{f}(x,y)$ is given by $$\hat{f}(x,y)=f(x,y)+\text{offset} \quad (2),$$

where pixels satisfying $\hat{f}(x,y)<0$ are limited to $\hat{f}(x,y)=0$, while pixels satisfying $\hat{f}(x,y)=255$ are limited to $\hat{f}(x,y)=255$.

Practically the image processor 56 executes the processes shown in FIG. 33. First, the image processor 56 uses the density f(x, y) of each pixel (x, y) to calculate the shift amount "offset" based on formula (1) (step S102A). The image processor 56 then specifies a pixel position (x, y) according to a preset algorithm (step S102B). This process makes it possible to specify a pixel located at the first line and the first column in the two-dimensional image.

The image processor 56 uses formula (2) to calculate a new density $\hat{f}(x,y)$ shifted at the specified pixel (x, y) (step S102C). This density shift is one of the features of the present invention.

This new density $\hat{f}(x,y)$ is then subjected to the foregoing limit processes executed by the image processor 56. Specifically, it is determined whether or not the currently processed pixel (x, y) meets the density $\hat{f}(x,y)<0$, and if this is met, the lower value is limited to $\hat{f}(x,y)=0$ (steps S102D and S102E). In contras, when the determination is $\hat{f}(x,y)=0$ (NO at step S102D), it is then determined whether or not the pixel (x, y) meets the density of $\hat{f}(x,y)>255$. If this is met, the upper value is limited to $\hat{f}(x,y)=255$ (steps S102F and S102G).

After this, the image processor 56 determines whether or not the foregoing processes have been compelled at all the pixels (x, y) (step S102H). When this determination is NO, the processing is returned to step S102B, and the processes at steps S102B to S102G are repeatedly performed at the next pixel (x, y). In contrast, the determination at step S102H is YES, this processing for the density shift is ended.

In this way, the density shift is performed as a preprocess, curves in the density histogram are shifted as exemplified in FIG. 34. In this example, a histogram curve A explains that there are lots of pixels running off the scale (scale out) before the density shift. By contrast, after the density shift, the whole histogram curve is moved to the center of the scale, thus reducing the number of pixels running off the scale.

(Multiresolution Decomposition)

Returning back to FIG. 32, the description will be continued. The image processor 56 executes a process for the multiresolution decomposition on the original image whose densities (pixel values) are shifted by applying, for example, wavelet transform thereto (step S103). By way of example, this wavelet transform is sequentially executed at each of the levels j=1 to 8. The levels j show the degree how deeply the multiresolution decomposition is carried out. The lower the levels j, the higher the resolution (accordingly, the level j=1 shows the highest resolution).

The wavelet transform can be performed using a two-dimensional discrete wavelet transform whose basis function is Daubechies function. By applying this wavelet transform to the densities $\hat{f}(x,y)$ of the original image subjected to the density shift, sub-bands are produced.

This wavelet transform is a means which uses a basis function belonging to a square integrable function $L^2(R)$ to express arbitrary signals falling into this function $L^2(R)$. That is, the wavelet transform provides an inner product calculated between the basis function obtained by shifting or scaling up/down the wavelet (short wave; wave-lets) function in the time domain and objects to be processed.

This wavelet transform is performed on the assumption that original image data $\hat{f}(m,n)$ provide a scaling coefficient $s_{m,n}^{(0)}$ at the level 0. This scaling coefficient $s_{m,n}^{(0)}$ is subjected to the discrete wavelet transform in its lateral diction, and resultant two coefficients in the lateral direction (i.e., scaling coefficient s and wavelet expansion coefficient w) are then subjected to discrete wavelet transform in the longitudinal direction. These steps provide the following four coefficients:

$$s_{m,n}^{(j=1)} = \sum_l \sum_k \overline{p_{k-2m} p_{l-2n} s_{k,l}^{(j)}} \quad (3)$$

$$w_{m,n}^{(j+1,h)} = \sum_l \sum_k \overline{p_{k-2m} q_{l-2n} s_{k,l}^{(j)}}$$

$$w_{m,n}^{(j+1,v)} = \sum_l \sum_k \overline{q_{k-2m} p_{l-2n} s_{k,l}^{(j)}}$$

$$w_{m,n}^{(j+1,d)} = \sum_l \sum_k \overline{q_{k-2m} q_{l-2n} s_{k,l}^{(j)}},$$

where j denotes the level, and m and n denote sizes in the lateral and longitudinal directions, respectively. $s_{m,n}^{(j+1)}$ denotes an expansion coefficient of low frequency components after performing the wavelet transform, while $w_{m,n}^{(j+1,h)}$, $w_{m,n}^{(j+1,v)}$ and $w_{m,n}^{(j+1,d)}$ denote expansion coefficient of high frequency components. Of these, $w_{m,n}^{(j+1,h)}$ shows a coefficient produced by applying the scaling function in the lateral direction and applying the wavelets in the longitudinal direction, $w_{m,n}^{(j+1,v)}$ shows a coefficient produced by applying the wavelets in the lateral direction and applying the scaling function in the longitudinal direction, and $w_{m,n}^{(j+1,d)}$ shows a coefficient produced by applying the wavelets in both lateral and longitudinal directions. $P_k$ denotes a sequence of numbers of the scaling function and $q_k$ denotes a sequence of numbers of the wavelets. The symbols h, v and d mean applications of the wavelets in the lateral, longitudinal, and, both lateral and longitudinal directions, respectively. In addition, the superior bars in the formula (3) represent complex conjugate.

The image processor 56 executes the wavelet transform at the level j=1 on the assumption that the original image data $\hat{f}(m,n)$ are the scaling coefficient $S_{m,n}^{(0)}$ at the level j=0. Completing the wavelet transform at the level j=1 results in producing low-frequency expansion coefficients $s^{(1)}$, which are then subjected to the wavelet transform at the level j=2. When completing the wavelet transform at the level j=2, resultant low-frequency explanation coefficients $s^{(2)}$ are subjected to the wavelet transform at the level j=3. This process is repeated, so that the multiresolution analysis is performed.

Incidentally, the wavelet transform is helpful for the multiresolution analysis, but other appropriate transform techniques can also be used. Even if the wavelet transform is employed, it is not always limited to the wavelet transform whose basis is Daubechies function. For example, other transform techniques on Haar wavelet may be used.

FIG. 35 pictorially shows a coefficient image (FIG. 35 (*b*)) produced by applying the level J=1 wavelet transform to the original image $S^{(0)}$ whose pixel number is n×m pieces (refer to FIG. 35 (*a*)); a further coefficient image (FIG. 35(*c*)) produced by applying the level j=2 wavelet transform to an expansion coefficient image $S^{(1)}$ of low frequency components of the coefficient image in FIG. 35(*b*); and a further coefficient image (FIG. 35(*d*)) produced by applying the level j=3 wavelet transform to an expansion coefficient image $S^{(2)}$ of low frequency components of the coefficient image in FIG. 35(*c*).

(Weighting Process)

When the wavelet transform is finished, the image processor 56 applies a weighting process for the contrast enhancement to the coefficients resultant from that transform (step S104). This weighting process provides another feature of the present invention, which is outlined in FIG. 36. This weighting process is performed depending on characteristics (attributes) of densities of the original image.

<Automatic Setting of Reference Weight>

First, the setting (specification) of a reference weight, which is executed by the image processor 56, will now be described (step S104A).

Both of the coefficients s of the low frequency components and the coefficients w of the high frequency components of the sub-bands are obtained by the foregoing wavelet transform at each level j (in the present embodiment, j=1 to 8). Since gradient information of an image is contained in the high frequency components, the contrast to the image can be enhanced (or adjusted) by treating the high frequency components. For that, the high frequency components of the sub-bands at each level j are weighted. Those weights are denoted as α(j).

How this weights α(j) are calculated for the adjustment (i.e., automatic setting of the weights) will now be described.

The present inventors conducted a research of relationship between the weights α(j) and the density histogram and had knowledge of some features of this relationship. One feature is that the weights α(j) are set at the same value regardless of how the level j is, a range in which pixel densities reside can become large in proportion to the magnitudes of values of the weights α(j). It is also found that the weights α(j) are set to be excessively larger, the number of pixels whose values run off the scale of densities 0 to 255 increases as well, which is undesirable. In consideration of this fact, in the present embodiment, the weights α(j) are set automatically based on a ratio of the number of scaled-out pixels to the number of all pixels. For such setting, a reference weight $α_0$ (=α(1)) will now be decided as follows.

This reference weight $α_0$ is required to provide the top priority to the highest-frequency (high resolution) image (image at the level j=1) among images to be subjected to the contrast enhancement. Thus, this image is weighted with the use of the largest weight (=the reference weight $α_0$).

The value of this reference weight $α_0$ depends on setting conditions, in which by way of example, that value is nearly 3 to 4 or thereabouts.

First, the image processor 56 uses the original image $\hat{f}(x,y)$, whose densities (pixel values) are shifted, to produce a density histogram h(i) (i=0 to 255). Then an accumulated densities expressed by $$C_l(i) = \sum_{k=0}^{i_l} h(k) \qquad (4)$$

$$C_h(i) = M^2 - \sum_{k=0}^{i_h} h(k) \qquad (5)$$

are produced

When assuming that the scale-out ratio is denoted as $\beta$ ($0 \leq \beta < 1$), the number of pixels scaled out is $M^2\beta$. Hence, the values of parameters $i_l$ and $i_h$ that meet a condition of $$M^2\beta \cong C_l(i_l) + C_h(i_h) \qquad (6)$$

are calculated in parallel by, as to the parameter $i_l$, incrementing one by one from 0 and by, as to the parameter ih, decrementing one by one from 255. Using the calculated values of the parameters $i_l$ and $i_h$, the reference weight $\alpha_0$ is set based on a formula of $$\alpha_0 = \frac{256}{i_h - i_l}. \qquad (7)$$

<Setting of Weighting Function>

As described, when the reference weight $\alpha_0$ is found from the density histogram of the original image itself to be processed, that is, an attribute of the original image, the image processor 56 uses that reference weight $\alpha_0$ to automatically set a weighting function in accordance with one of a plurality of types of patterns which are preset (step S104B).

In other words, in the present embodiment, in consideration of the fact that the image contrast enhancement effect can be changed by changing the weights $\alpha(i)$ at every sub-band, the image processor 56 applies the decided reference weight $\alpha_0$ to the following formulas to calculate five types of weighting functions. The functional values of those five type of weighing functions calculated as above are stored, at every level j, in a table, for instance.

$$\alpha(j) = \alpha_0 \qquad (8)$$

$$\alpha(j) = \frac{\alpha_0 - 1}{1 + \tan\left(\frac{j-1}{7} * \frac{\pi}{2}\right)} + 1 \qquad (9)$$

$$\alpha(j) = \frac{1}{7}\{(1 - \alpha_0) * j + (8\alpha_0 - 1)\} \qquad (10)$$

$$\alpha(j) = (\alpha_0 - 1) * \frac{\log(9 - j)}{\log 8} + 1 \qquad (11)$$

$$\alpha(j) = \frac{8(\alpha_0 - 1)}{7 * j} + \frac{8 - \alpha_0}{7} \qquad (12)$$

Of these formulas, the weighting function set on the formula (8), which is shown by a straight line in FIG. 37, has a weight $\alpha(j)$ of a constant value $\alpha_0$ (=the reference weight). This weight $\alpha(j)=\alpha_0$ is to be given to the highest frequency (high resolution) image components of a image to be enhanced.

The weighting function set on the formula (10) is shown by a straight line B in FIG. 37, in which the weight $\alpha(j)$ becomes the reference weight $\alpha_0$ at the level j=1 and decreases linearly from that value as the level j increases and reaches the weight $\alpha(j)=1$ at the level j=8. This weight $\alpha(j)=1$ is to be given to the image components at the highest level j=8. Such image components mean an average density over the original image. In the present embodiment, the density shift is carried out in advance, so that the weight is for the average density value=128.

The weighting function set on the formula (9) is shown by a curve B2 in FIG. 37. In this curve, the weight $\alpha(j)$ equals the reference weight $\alpha_0$ at the level j=1, and as the level j increases, the weight $\alpha(j)$ decreases along a gentle sigmoid (i.e., non-linear) locus and reaches the weight $\alpha(j)=1$ at the level j=8. More specifically, as the level j increases from 1, the curve goes along a weighting curve with a gentle downward deviation and, from a boundary at the level j=4, differently from the first half, goes along a weighing curve with a gentle upward deviation. And the weight $\alpha(j)=1$ is finally realized at the level j=8.

Further, the weighting function set on the formula (11) is shown by a weighing curve B3 in FIG. 37. In this case, the weight $\alpha(j)$ equals the reference weight $\alpha_0$ at the level j=1, and decreases gently from this value with an increase in the level j. The rate of decrease is lower when the level j is relatively lower, but becomes larger sharply in the last half part during which the level j is higher. By contrast, the weighting function set on the formula (12) is shown by a weighing curve B4 in FIG. 37. In this case, the weight $\alpha(j)$ equals the reference weight $\alpha_0$ at the level j=1, and decreases from this value with an increase in the level j. The rate of decrease is higher when the level j is relatively lower, but becomes lower gradually to be saturated in the last half part during which the level j is higher.

Of these weighting functions, the weighting functions expressed by the straight lines A and B1 and curves B2 to B4 can be classified into monotone non-increasing functions, and the weighing functions expressed by the straight line B1 and curves B2 to B4 can be classified as monotone decreasing functions.

The straight line B1 and curves B2 to B4 provides the weighting functions (monotone non-increasing functions) whose weights are non-constant depending on the levels J. Of these functions, the curves B2 to B4 provide the non-linear weighting functions. Incidentally, the straight line A provides the linear weighting function having a constant value, while the straight line B1 also provides the linear weighting function.

The reason why these plurality of types of weighting functions are set is for widening the scope of choice for a contrast enhancement manner proper for image contents, even if the original image to be processed has any type of contents (i.e., density attributes).

The various types of weighing functions shown in FIG. 37 is generalized into a form. This generalized weighing function is a function based on a variable j, which can be exemplified as follows:

$$\alpha(j) = a_n j^n + a_{n-1} j^{n-1} + \ldots a_1 j + a_0$$

($a_n, a_{n-1}, \ldots, a_0$: real coefficients), which can be expressed as a function passing $\alpha(1)=\alpha_0$ and $\alpha(8)=1$ and being monotone non-increasing at j=1 to 8. Setting the real coefficients $a_n, a_{n-1}, \ldots, a_0$ to proper values makes it possible to change the weighting function into a desired one, as exemplified by the curves B1 to B4 in FIG. 37. The weighing function expressed by the straight line A does not meet a condition of $\alpha(8)=1$, but this function may be used when all the enhancement weights are decided to be constant.

Incidentally, the maximum amount of the levels j depends on the size (matrix size) of an image to be processed. For example, for an image matrix size=256×256, the maximum level is set to j=8, while for an image matrix size=1024×1024, the maximum level is set to j=10. Thus, if it is required to have a weighing function up to the maximum level j=10, used is a decreasing weighting function whose weights $\alpha(j)$ are $\alpha_0$ and 1 at the levels j=1 and 10, respectively.

<Selection of Weighting Functions>

The calculation processor 13 selects (specifies) a proper weighting function depending on the attributes of densities of the original image, from the plurality of types of weighting functions automatically set in according with the reference weight $\alpha_0$ as above (steps S104C to S104J).

As described, in the present embodiment, the weights $\alpha(j)$ for the high frequencies are controlled for reconstructing images (performing inverse wavelet transform), so that contrast-enhanced images are produced. Meanwhile, a present inventors' research showed that how the weights $\alpha(j)$ are given makes degrees of resultant contrast enhancement differ from each other.

This will now be described. In general, the contrast enhancement is performed using the constant weights, like the straight line A (the formula (9)) in FIG. 37, the scale-out events become distinct. This owes to the fact that setting the weights $\alpha(j)$ to be constant regardless of being the levels j limits densities to be picked up, though its dynamic range can be widened. In cases where the weighting function is set to be non-linear, as shown by the curve B4 (the formula (12)) in FIG. 37, the effect of the contrast enhancement is low because the weights $\alpha(j)$ are small in higher levels j.

In contrast, when employing the non-constant weighing functions expressed by the curve B2 (the formula (9)), the straight line B2 (the formula (10)), and the curve B3 (the formula (11)) in FIG. 37, the scale-out events can be suppressed and fine characteristics of the contents of the original image can be enhanced well.

However, it has also been found that the non-constant weights $\alpha(j)$ are not always for all purposes. For example, it has been known that, when the original image has a specific area such as "sky" where there are lots of specific densities (pixel values), the non-constant weighting functions are not proper and artifacts are caused in such an area. In this kind of original image, from the viewpoint of suppressing the artifacts, the weighing function whose weights are constant should be used.

In summary, it is necessary to select a weighting function with taking it account that the original image includes many regions whose densities are similar, like the "sky"; the original image includes regions whose densities change sharply, like the roof and wall of a "house"; the original image includes lots of changes in densities, like a "figure"; and others. Namely, it is essential to determine the features of densities of an original image to be processed and to select (or switch over to) a weighting function proper for the features.

In the present embodiment, the ratio of high frequency components, included in the densities of an original mage, to low frequency components thereof is adopted as a basic index used in selecting a proper weighting function. This ratio was found by the inventors as one index which enables determination of the features of an original image. Another index is a maximum inclination obtained from the accumulated histogram, which is also useful for the determination. In the present embodiment, the foregoing "ratio of high frequency components" and the "maximum inclination of an accumulated histogram" are combined as a technique to determine the features of an original image, thereby making the determination upgrade in its reliability. Incidentally, in cases greater importance is given to simplifying the processing, only the "ratio of high frequency components" may be used for the determination, without using the "maximum inclination of an accumulated histogram."

With considering the above, the description will now be returned to FIG. 36. The image processor 56 calculates, at each level j, the ratio R of the sum of absolute values of high frequency components to the sum of absolute values of low frequency components, from the coefficient information of the multiresolution decomposition derived by the wavelet transform at each level j (step S104C). By this calculation, for example, the seven rates R from the levels j=1 to 8 are provided.

Then the image processor 56 determines whether or not each rate R is equal to or less than a predetermined threshold $R_{th}$ (step S104D).

When the determination is YES, that is, $R \leq R_{th}$ is established, the image processor 56 calculates the maximum inclination $INC_{max}$ of an accumulated density histogram (step S104E). The maximum inclination of the accumulated density histogram is a maximum inclination appearing on a curve obtained by integrating the accumulated histogram (refer to FIG. 38).

When this maximum inclination $INC_{max}$ is obtained, it is determined by the image processor 56 whether or not the maximum inclination $INC_{max}$ is $INC_{max} \geq INC_{th}$ (step S104F). The threshold $INC_{th}$ is a desired value which is set in advance. When it is determined YES at this determination, that is, the maximum inclination $INC_{max} \geq INC_{th}$, the image processor 56 selects, as the desired weighting function, a function having a constant weight $\alpha(j)$ based on the formula (8) (step S104G).

By contrast, when it is determined NO at step S104F, that is, the maximum inclination $INC_{max} < INC_{th}$, and it is determined NO at the foregoing step S104D, that is, the rate $R > R_{th}$, the non-linear weights $\alpha(j)$ based on the formula (9) (refer to the curve B2 in FIG. 37) is selected as an example (step S104H). As a modification, this step S104H may be configured to select appropriate weights $\alpha(j)$ based on any of the formulas (9) to (12).

The processes at steps S104D to S104H are repeated as for each of predetermined levels j (for example, j=1, 2) which are preset depending on the size of the original image (step S104I). For example, for a two-dimensional image whose pixels are 256×256, the determination of the rate $R \leq R_{th}$ is made as for each of the levels j=1, 2, repeating the foregoing processes at each level. If the two-dimensional image has the number of pixels of 1024×1024, the determination of the rate $R \leq R_{th}$ is made as for each of the levels j=1, 2 and 3, repeating the foregoing processes at each level.

In this way, the number of levels j to be determined is made larger as the number of pixels increases, so that the attributes and features owned by the densities of the original image can be determined finely. The reason why the determination of the rate $R \leq R_{th}$ is not always made for all the levels j=1 to 8 is that it is normal that this rate R has not so much significance at higher levels j. Hence it is desired to limit the levels j to a moderate amount in consideration of the amount of calculation.

Thus, when the determination and setting the weighting function have been made at the appropriate levels j=1, 2, the image processor 56 is able to estimate the tendency of the weighting functions for all the levels j=1 to 8. Based on this estimation, the weighting functions for the remaining levels j=3 to 8 are selected (step S104J).

As a result of the determination at the levels j=1, 2, the non-linear weighting functions based on the formula (9) or the constant weighing function based on the formula (8) may be selected at both levels j=1, 2. Alternatively, there may be a case where the non-linear weighting function based on the formula (9) is selected at the level j=1 but the constant weighing function based on the formula (8) is selected at the level j=2. Hence, by way of example, at step S104J, the weighting function selected at the level j=2 can be applied to the levels j=3 to 8. Alternatively, at higher levels j, the weighting process may be omitted (in this case, a weight=1 is set).

When completing the automatic setting of the optimum weighting functions at the respective levels j depending on the attributes and features of densities of the original image as above, the image processor 56 moves to setting the values of the weights α(j) by making reference to the functional values (tables) of the weighting functions which has been set (step 104K).

The image processor 56 then moves its processing to step S105 in the foregoing FIG. 32, where the image processor reconstructs an image whose high frequency components are given the weights α(j) which has been set. This reconstruction is performed based on the inverse wavelet transform based on a formula of $$s_{m,n}^{(j)} = \sum_k \sum_l \left[ p_{m-2k} p_{n-2l} s_{k,l}^{(j+1)} + \alpha(j) p_{m-2k} q_{n-2l} w_{k,l}^{(j-l,h)} + \alpha(j) q_{m-2k} p_{n-2l} w_{k,l}^{(j+l,v)} + \alpha(j) q_{m-2k} q_{n-2l} w_{k,l}^{(j+l,d)} \right]. \quad (13)$$

Based on the values $s_{m,n}^{(j)}$ resulting from the inverse wavelet transform, a new image is obtained which is subjected to the final contrast enhancement.

At step S105, the reconstructed image is displayed by the display device 17 and its image data are stored in the image data storage 12.

In the foregoing series of processes, it is preferable that the region for the density shift (the region from which the density average is calculated), the region for the multiresolution decomposition, the region used for determining the features of the image (the attributes of the densities), and the region used for setting the weighing functions are the same region in the ordinal image.

(Operations and Actions)

In this way, it is possible to apply the foregoing contrast enhancement process to a local region specified on the panoramic image. Accordingly, in addition to the operations and advantages gained in the first embodiment, various advantages derived from the contrast enhancement process can be provided.

First of all, the original image undergoes the density shift serving as a preprocess, with the result that the dynamic range of the density gradations can be used effectively and the contrast enhancement process following the preprocess can be optimized.

Moreover, since the weights α(j) are changed at every level j, a reconstructed image is based on a plurality of density levels. Hence, the scale-out events can be suppressed, while still suppressing block artifacts. With structures based on the low frequency components visually shown, it is possible to reliably enhance the contrast of even fine features of the original image. In consequence, it is possible to gain a superior representation in the gradations and to enhance the contrast of a wider density region in the entire image in an optimized manner.

Another advantage is that, differently from the conventional various image contrast enhancement techniques, the present embodiment adopts the way of combining "the rate of the absolute values of the high frequency components to the absolute values of the low frequency components" and "the maximum inclination of the accumulated histogram." This makes it possible that the contrast enhancement automatically and reliably considers the features of an image. Artifacts can be suppressed largely in the contrast-enhanced image, improving the panoramic images in quality.

In this way, according to the contrast enhancement technique according to the present embodiment, the enhancement of noise can be avoided from being excessive in image regions having smaller changes in the densities and the whole image keeps texture, while still enhancing the contrast of features of the original image. As a result, panoramic images which are helpful for dental interpretation can be provided.

Additionally, as described, the density shift is carried out, so that the dynamic range can be used fully to provide sharp images. At the same time, setting the smooth weighting coefficients leads to a reliable suppression of generation of block artifacts, improving the image quality.

Differently from some conventional contrast enhancement techniques, the weighing process is simply applied to the coefficients of the high frequency components which have been subjected to the multiresolution decomposition. Thus the amount of calculation is not so large, suppressing the calculation load from increasing excessively. The weighting is almost always matched to the features of images, so that undesirable events such as an excessive contrast enhancement and generation of block-shaped artifacts can be suppressed.

In the present embodiment, the contrast enhancement process representatively shown in FIG. 32 is executed by the image processor 56 in an automatic manner. It is enough that an operator simply handles the operation devices 58 to command the execution of the processing. Additionally this automatic contrast enhancement is based on the features of each original image, as described. It is therefore possible for operators to save the operations and gain contrast-enhanced images in a reliable manner.

The contrast enhancement process applicable to the present panoramic imaging apparatus cannot always be limited to the foregoing one, but may adopt known techniques. For example, a Histogram Equalization (HE) technique that involves histogram operations, a Contrast Limited Adaptive Histogram Equalization (CLAHE) technique that gives locality to the contrast enhancement to suppress the enhancement from being excessive, and a technique that uses information indicative of gradients in image densities. References for the known contrast enhancement processes are listed below.

[Non-patent reference 1]
W. K. Pratt: Digital image processing, John Wiley & Sons, New York, 1978

[Non-patent reference 2]
S. M. Pizer, et al.: "Adaptive histogram equalization and its variations," Comput. Vision, graph. image proc., vol. 39, pp. 355-368, 1987.

[Non-patent reference 3]
S. G. Mallat, S. Zhong: "Characterization of signals from multiscale edges," IEEE Trans. PAMI, vol. 14, pp. 710-732, 1992

[Non-patent reference 4]
J. Lu, et al.: "Contrast enhancement via multiscale gradient transformation," IEEE Int'l Conf Imag. Proc. (ICIP), pp. 482-486, 1994.

[Non-patent reference 5]
J. J. Heine, et al.: "Multiresolution statistical analysis of high-resolution digital mammograms," IEEE Trans. Medical Imaging, vol. 16, pp. 503-505, 1997
[Non-patent reference 6]
K. V. Velde: "Multi-scale color image enhancement," IEEE Int Conf Image Proc (ICIP), vol. 3, pp. 584-587, 1999
[Patent reference 1]
U.S. Pat. No. 5,467,404
[Patent reference 2]
U.S. Pat. No. 5,960,123

Third Embodiment

Referring to FIGS. 39 and 40, a third embodiment of the panoramic imaging apparatus according to the present invention will now be described. The similar hardware components to those described already are given the same reference numerals as those.

Even if a patient's tooth row is far from an ideal one such that, for example, adjacent teeth are overlapped with each other, the present panoramic imaging apparatus is able to image how those tooth are overlapped and the anteroposterior relationship of those tooth in a proper manner. In the past, there is an overlap between teeth, the overlap portion appears in white in a panoramic image, making the interpretation impossible or lowering accuracy in the interpretation.

This problem can be solved by performing a later-described effective width control process at a proper timing during the interpretation process shown in FIGS. 19 and 20 or after the interpretation process.

This effective width control process is to control the lateral effective width of the incident area 32A of the detector 32, which is executed by the controller 57 as a software process. To be specific, the X-ray-incident effective width of the detector 32 in the lateral direction along which the detector 32 is moved and the position of this effective position are controlled freely on the data of a panoramic image. Thus, in the present embodiment, the producing function of partial sectional images (images of partial sections specified by ROIs), which is functionally realized by the controller 57, has the effective width control process function. This effective width control process can be executed in each of the foregoing first and second embodiments.

FIGS. 39(A) and (B) pictorially shows an overlap between mutually adjacent teeth 1 and 2. The normal effective width W1, for example, 3.5 mm, of the detector 32, to which the X-ray comes, is made small (for example, W2=2 mm), and the X-ray entering the small effective width is moved to the right and/or left ends in the lateral direction of the incident area 32A of the detector 32 (i.e., the direction along which the detector 32 is moved for scanning). The process for reducing and moving the effective width is carried out by the controller 57 on software processing. At the overlap portion between tooth, the X-ray tube 31 and detector 32 are directed to both tooth 1 and 2 at the same time. The interpreter is therefore set the effective width of the detector so that the effective width is made small and moved to avoid the overlap as much as possible, thus making it possible to reduce the overlap on the image as much as possible. For instance, FIGS. 39(A) and 39(B) pictorially show that the X-ray tube 31 and the detector 32 reside at the same position along a movement trajectory for scanning, where the effective width W in FIG. 39(B) is narrower than that in FIG. 39(A). Thus, thanks to the smaller effective width, the case shown in FIG. 39(B) has less influence on the teeth overlap on the image, compared to the case shown in FIG. 39(A).

Utilizing this property, a process outlined in FIG. 40 is carried out interactively between the interpreter and the controller 57, whereby how much adjacent tooth are overlapped with each other can be understood visually.

As described, an overlap portion between teeth appears in panoramic images. Thus, the controller 57 receives from an interpreter ROI information to specify the overlap portion between teeth and a local region including this overlap portion (step S150). Then the controller 57 moves the effective width of the detector 31 to the left end of a detection plane 31A thereof depending on the overlap portion, and makes the image processor 56 reconstruct the image of the moved partial region (step S151). The movement of the effective width can be established, by way of example, by applying to the necessary frame data a filter composed of functional values of 1 and 0. Further, the reconstruction uses the foregoing gain. Then the controller 57 moves the effective width of the detector 31 to the right end of the detection plane 31A thereof depending on the overlap portion, and makes the image processor 56 reconstruct the image of the moved partial region (step S152). In this way, since the two types of images with their effective widths swung to the right and left respectively are produced, these images are displayed on the monitor 60 in a mutually comparative manner. Hence, the interpreter visually makes a comparison between the two types of displayed reconstructed images, so that it is easier for the interpreter to diagnose how the mutually adjacent teeth 1 and 2 overlap with each other. Further, any one of the reconstructed images provides an image which is less influenced by the overlap, improving diagnostic accuracy.

A collateral advantage can be derived from a configuration where the effective width (lateral width) of the detector 32 and the lateral position of the effective width is controlled in a preset manner from outside the apparatus, that is, the operation device 58. This configuration makes it possible that, at a position along the conventional tomographic orbit, which position provides observation of a tooth overlap, the lateral width of the detector 32 and the position of the lateral width are controlled equivalently such that the X-ray tube 31 and detector 32 takes a geometry allowing the tooth overlap to be reduced as much as possible. Hence this reduces tooth overlaps on a panoramic image as much as possible, where such overlaps made the diagnosis difficult in the past.

Fourth Embodiment

Referring to FIGS. 41 to 44, a fourth embodiment of the panoramic imaging apparatus according to the present invention will now be described. The hardware components similar to the foregoing will be given the same reference numerals.

Like the third embodiment, the panoramic imaging apparatus according to the present embodiment is intended to avoid an overlap between adjacent teeth in the depth direction, if any, in order to reliably represent the structure between the adjacent teeth.

To realize this feature, the panoramic imaging apparatus of the present invention is provided with a digital detector made of semiconductors having an X-ray incident area 82A shown in FIG. 41. As shown, the X-ray incident area 82A of the detector 82 is shaped as an approximately crisscross when viewed along an X-ray incident direction and consists of a first incident area K1 which extends in the lateral direction (X-direction) and a second incident area K2 which extends in the longitudinal direction (Y-direction) crossing the lateral direction. The size of the first incident area K1 is, for example, nearly "2.5 to 7.5 cm (its lateral length LA)×10 cm (its longitudinal length LB)." Thus this area K1 has a two-dimensional pixel area which is categorized as an area sensor, rather than a line sensor. In particular, it is preferred that the lateral length LA is larger than that of the conventional line sensor as large as possible. The longitudinal length LB is decided to fully cover the up-and-down region of patients' gum-ridges (refer to a chain double-dashed line H).

On the other hand, the second incident area K2 has linear pixel regions of which lateral widths are small, thereby making it possible to cover regions other than the gun-ridge to some extent. The reason why the second incident area K2 is elongated is to reduce the number of pixels which are not so much necessary for the imaging so that the amounts of signal processing and calculation are reduced. Incidentally, when the amount of processing does not become a main issue, the incident area of the detector 82 may be a rectangular shape which is able to cover the first and second incident areas K1 and K2.

Similarly to the foregoing detector 32, the detector 82 allows the first and second incident areas K1 and K2 to output digital detection signals corresponding to the strengths of X-rays transmitted via an object.

This detector 82 is arranged to be opposed to the X-ray tube 31 as illustrated in FIG. 42, and rotated around the jaw portion of a patient P for scanning so as to focus on a preset standard section. As a result, since the lateral direction of the first incident area K1 of the detector 82 is wide in the lateral direction, that is, the moved direction for scanning, the viewing range of X-ray paths that pass the tooth row expands. Hence some of the X-ray paths pass a path or a contacted gap between the mutually overlapped portions of adjacent teeth (i.e., a path between adjacent teeth). Namely, X-rays transmitted along X-ray paths passing a non-overlapped path between the mutually adjacent teeth also enter the first incident area K1.

Thus, the controller 57 uses frame data acquired with the use of the detector 82, to reconstruct a panoramic image Ppano of the object's standard section in the similar way as the above (refer to FIG. 43; steps S161 and S162; and FIG. 44). The controller 57 then uses operator's operational information to specify a partial viewing region on the panoramic image Ppano using a ROI (refer to step S163 and FIG. 44). It is preferred that this partial viewing region is specified at a certain region on the panoramic image Ppano, in which the certain region represents a tooth overlap in the depth direction or gives a doubt about the existence of such an overlap. The controller 57 specifies a partial region RG on a representation of the first incident area K1 of the detector 82 on the monitor screen, where the partial region RG corresponds to the partial viewing region (refer to step S164 and FIG. 44). This partial region RG is designated as an initial region, and, for example, put at one end in the lateral direction of the representation of the first incident area K1. The controller 57 uses part of frame data acquired by the initial region of the detector 82 to reconstruct and display an image Pa in the similar manner as the foregoing (step S165). Thus, as shown in FIG. 44, the image Pa is displayed in the viewing region (ROI) specified on the panoramic image Ppano.

Then, when the reconstruction and display are not finished (NO at step S166), the controller 57 automatically shifts the partial region RG on the representation of the first incident area K1 toward the other end by a predetermined amount, without changing the partial view region (ROI) (step S167). This is identical to the fact that the projection direction of the X-ray paths is changed without changing the position of the partial viewing region (ROI). The controller 57 then uses data (part of the remaining frame data) acquired at the moved partial region of the detector 82, so as to reconstruct and display an image in the same way as the above (step S165). The image Pa of the partial viewing region (ROI) specified on the panoramic image Ppano is thus displayed at another projection angle.

Hereinafter, similarly to the above, the controller 57 repeatedly reconstructs and displays the image of the partial viewing region, with automatically shifting the partial region on the representation of the first incident area K1 (steps S165 to S167). As a result, the image of the partial viewing region on the panoramic image Ppano is automatically displayed at different projection angles changed in sequence, by changing the partial region on the representation of the first incident area K1.

In this way, the operator specifies, as a ROI, a medically interested partial viewing region on the panoramic image Ppano only one time. Only this operation provides partial images whose projection angles are different from each other, while the viewing region is not changed in position. Accordingly, the operator is able to find images with less overlap or no overlap (gap), among the partial images to be displayed in sequence.

When such an image with less tooth overlap or no tooth overlap is found (YES at step S166), the operator commands to apply the foregoing focus optimization process to the found image so that the image is converted to an image Popt with less blur (refer to step S168 and FIG. 44).

As described, even when there is an overlap between mutually adjacent teeth in the depth direction, a focus-optimized image including a depiction of the structure between the mutually adjacent teeth can be obtained by employing the detector having a wider view, producing images with the projection angle shifted so that a projection angle passing a gap between the mutually adjacent and overlapped teeth is searched, and employing the focus optimization process when such a projection angle is searched.

Incidentally, depending on the degree of the view (largeness of the view) of the first incident area K2, the degree of an observable maximum overlap between mutually adjacent teeth is decided. The wider the first incident area K2, the larger the observable maximum overlap.

In the present embodiment, since the main point is to observe the tooth overlap, it is not necessary to give an excessively wide region to the second incident area K2 in the longitudinal direction. In order to reduce the amount of calculation load, the first incident area A1 is set to be narrower in the longitudinal direction. When searching the partial view image at the central projection angle, the second incident area is added to the first incident area so as to expand the partial view image in the longitudinal direction. The structural image provided by the expanded portion is also displayed as a reference.

The search for the projection angle that provides no tooth overlap may be automatically repeated until an operator's stop command.

Although the descriptions above contain many specificities, these should not be construed as limiting the scope of the invention but as merely providing illustrations of some of the presently preferred embodiments of the present invention. Thus the scope of the present invention should be determined by the appended claims.

Figure 1:
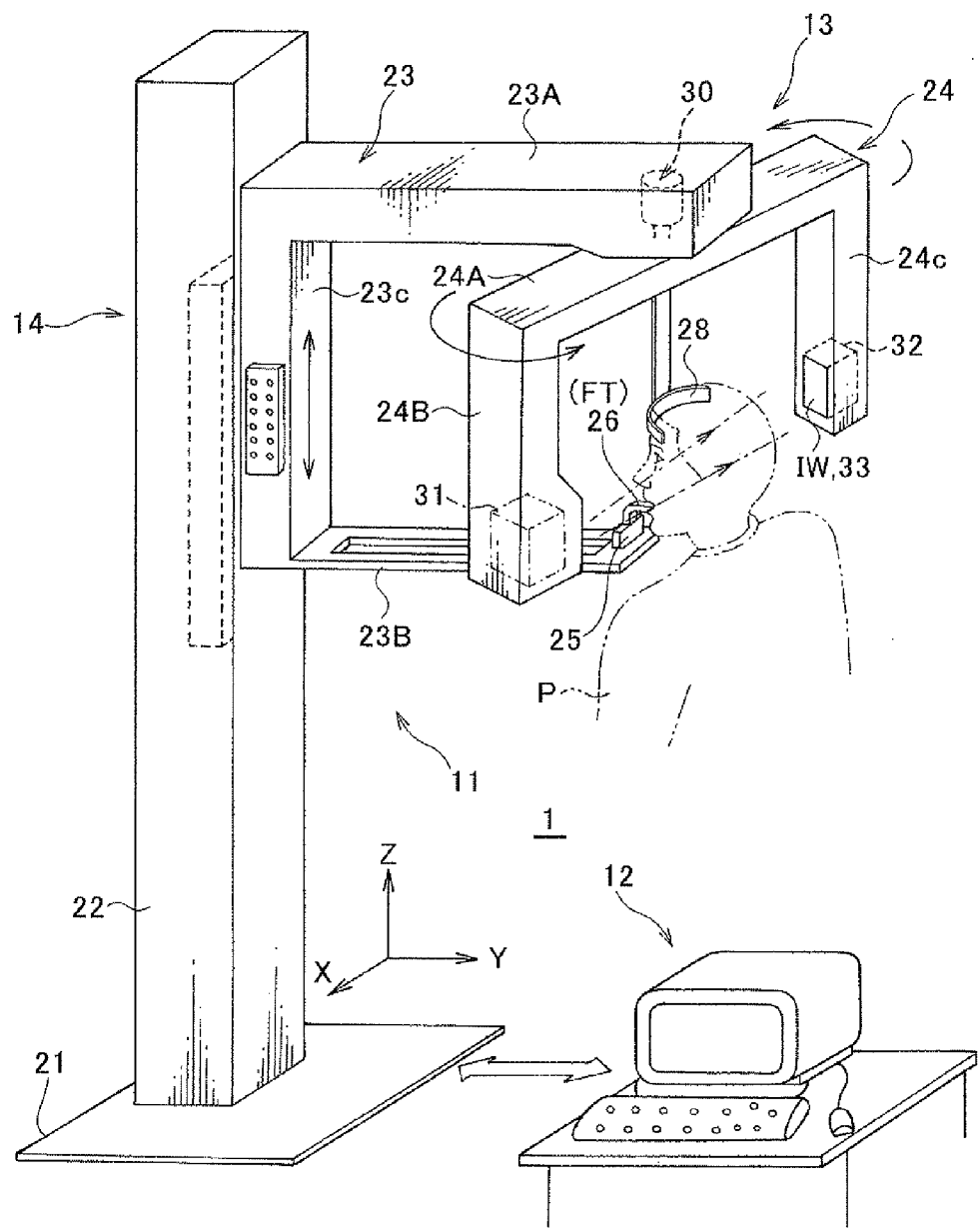
FIG. 1 is an outlined perspective view showing the an exterior appearance of a panoramic imaging apparatus according to the present invention.
Figure 2:
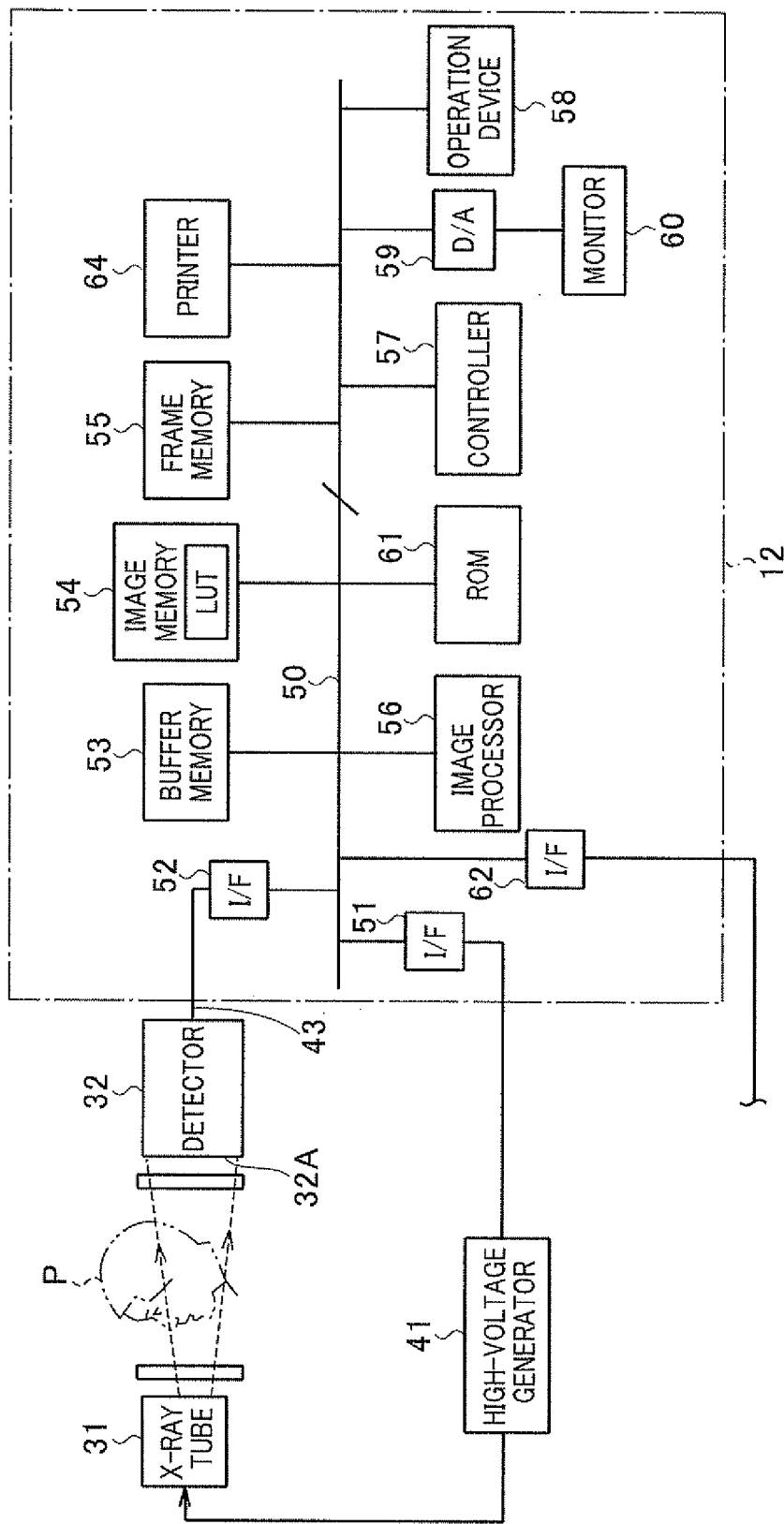
FIG. 2 is a block diagram showing the electrical configuration of the panoramic imaging apparatus according to the present invention.
Figure 3:
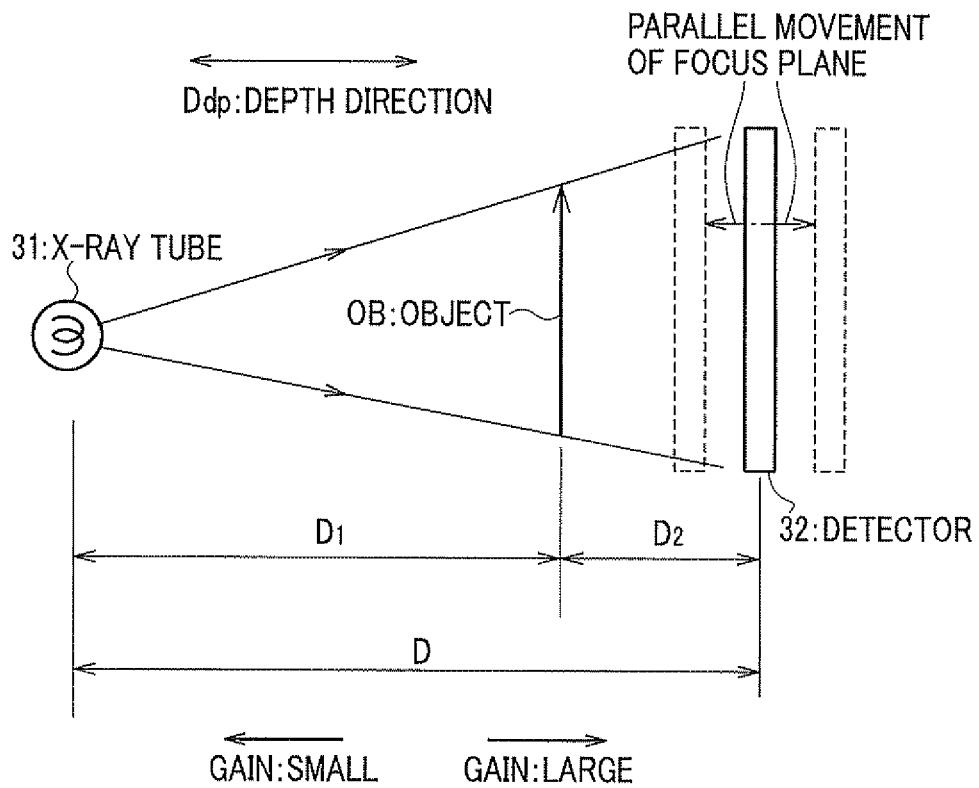
FIG. 3 explains a concept to show a gain for the focus, which is introduced by the present invention.
Figure 4:
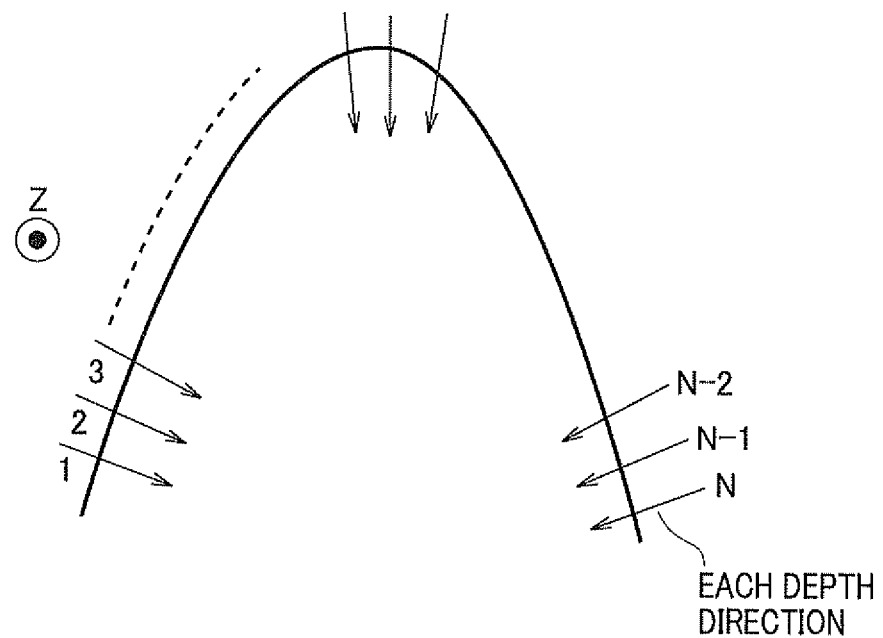
FIG. 4 explains the relationship between a row of teeth and the depth direction thereof.
Figure 5:
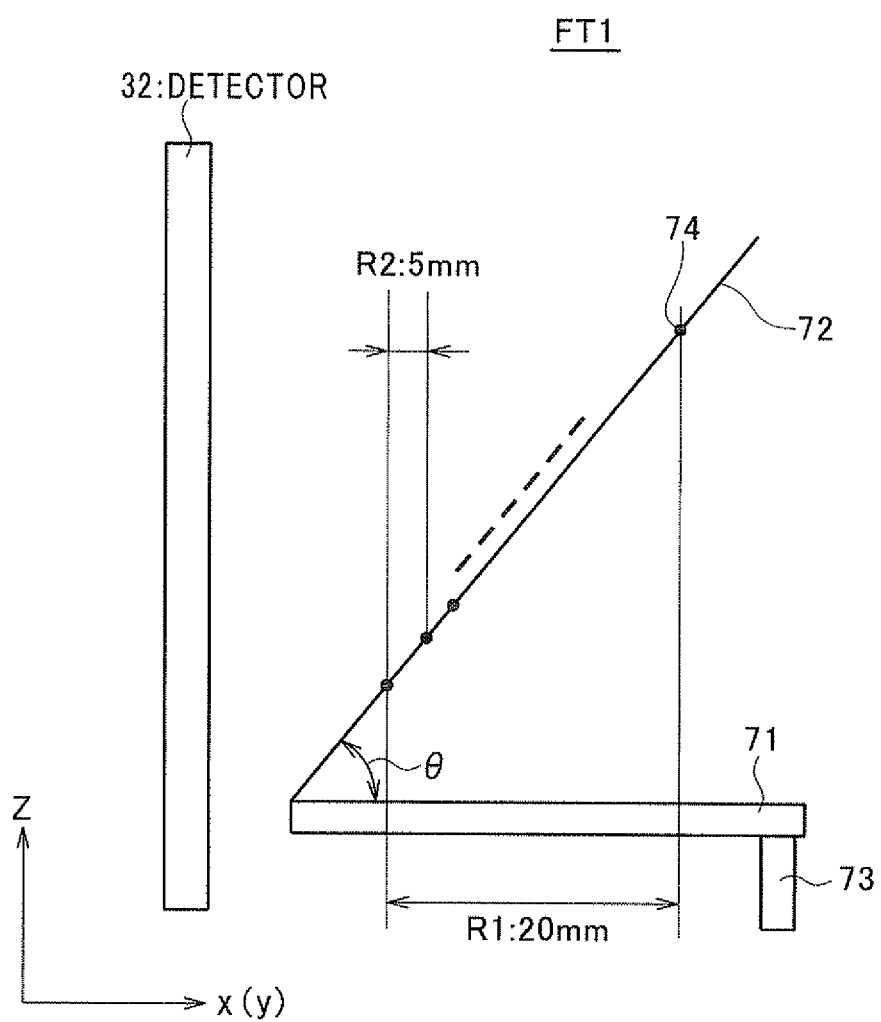
FIG. 5 is a view explaining one example of a phantom.
Figure 6A:
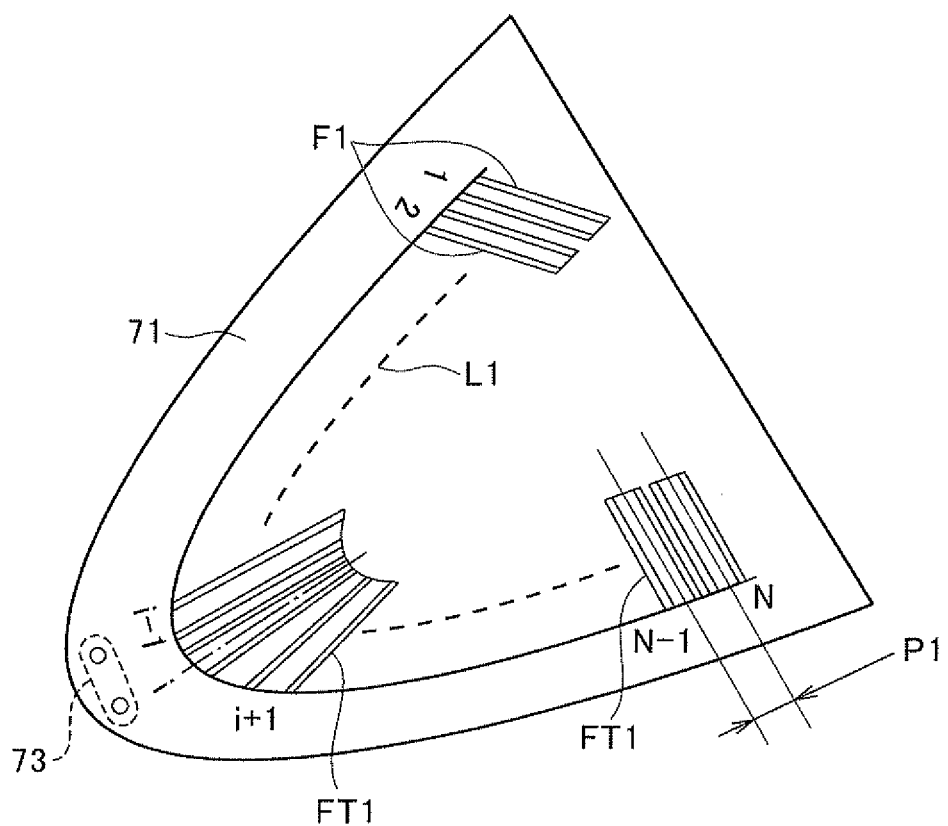
FIG. 6 is a view explaining another example of the phantom.
Figure 6B:
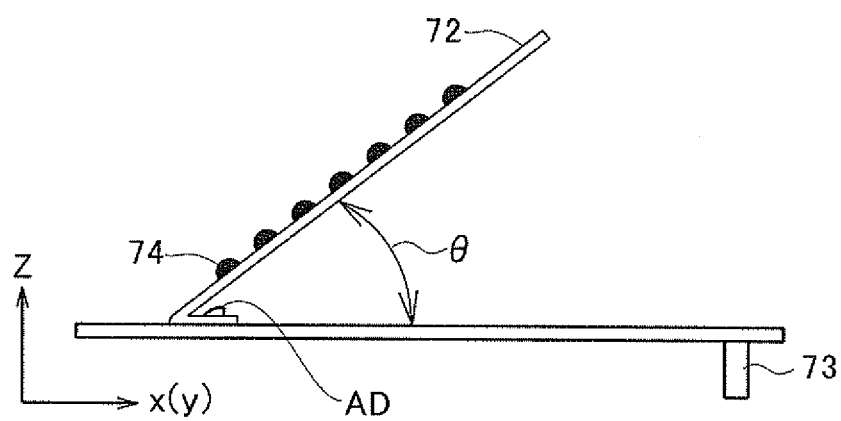
Figure 7:
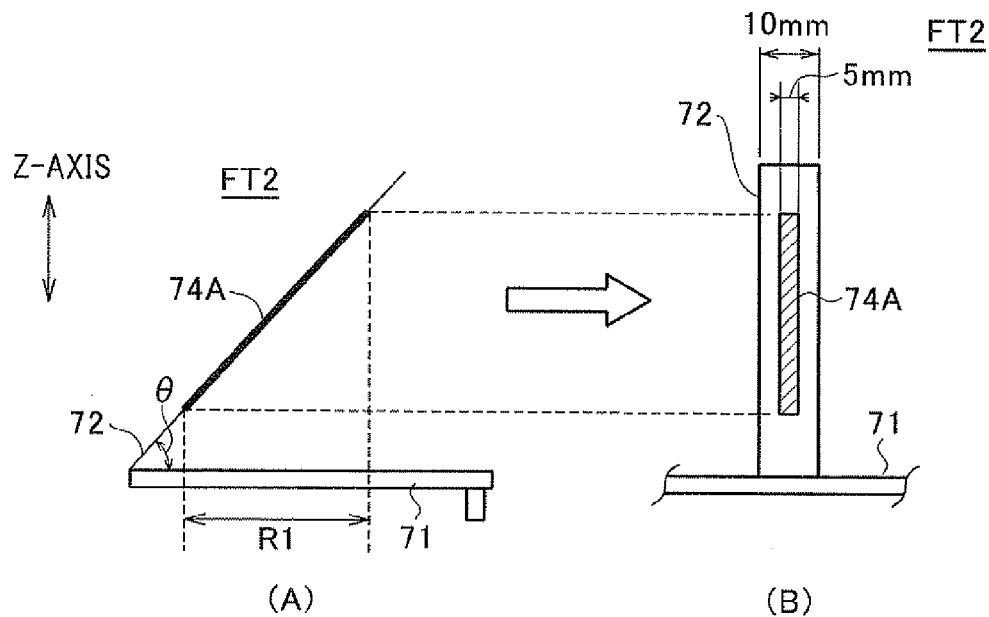
FIG. 7 is a view explaining another example of the phantom.
Figure 8:
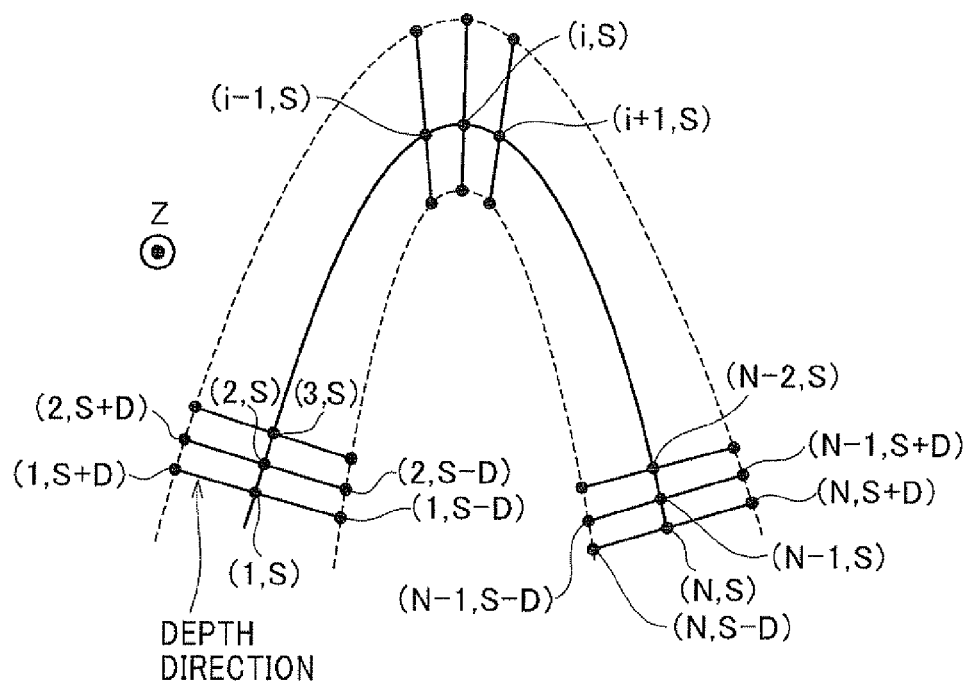
FIG. 8 is a view explaining both a row of teeth and a depth-directional range in which the gain is set.
Figure 9:
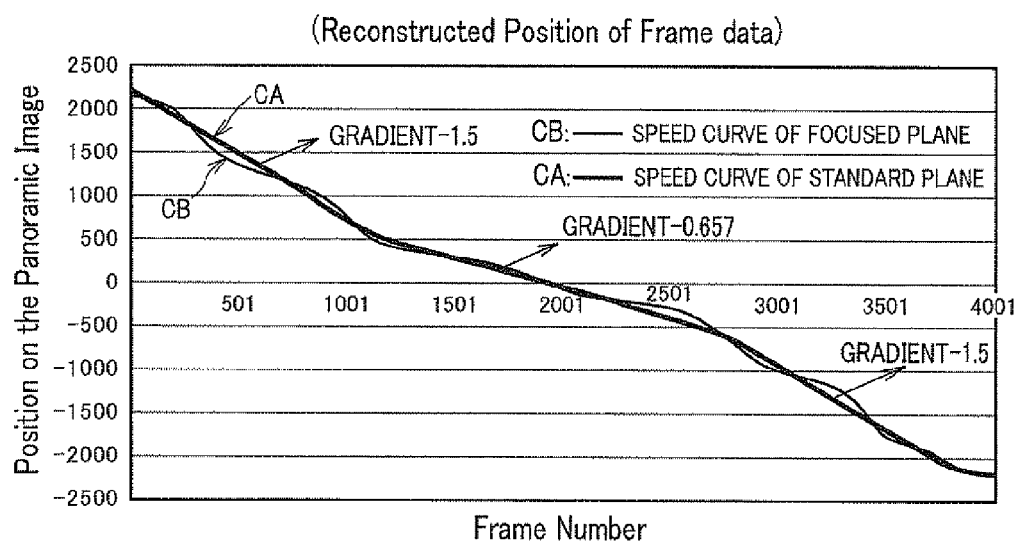
FIG. 9 a graph exemplifying a speed curve indicative of the gain introduced by the present invention.
Figure 10:
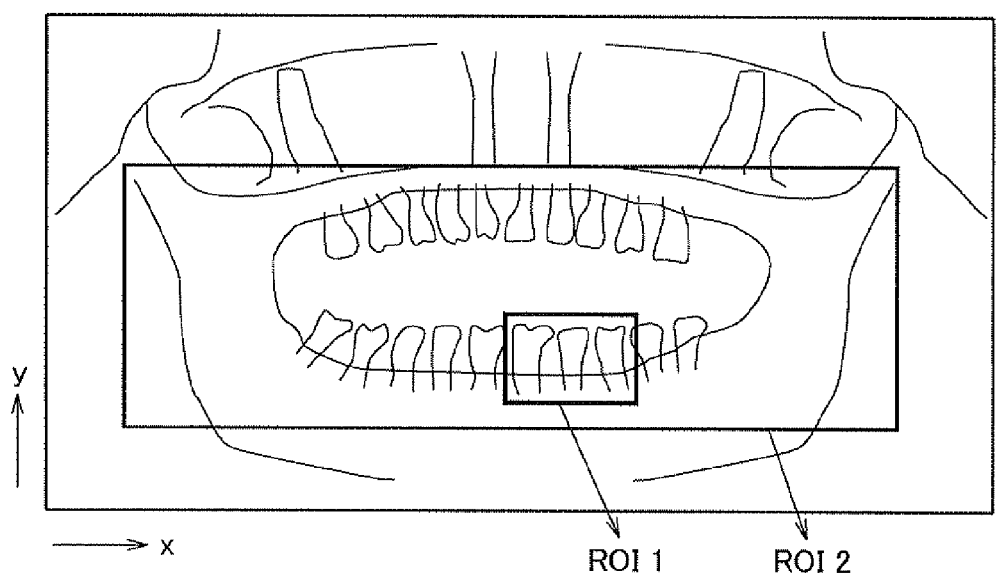
FIG. 10 exemplifies the types of ROIs which are set on a panoramic image of a standard section.
Figure 11:
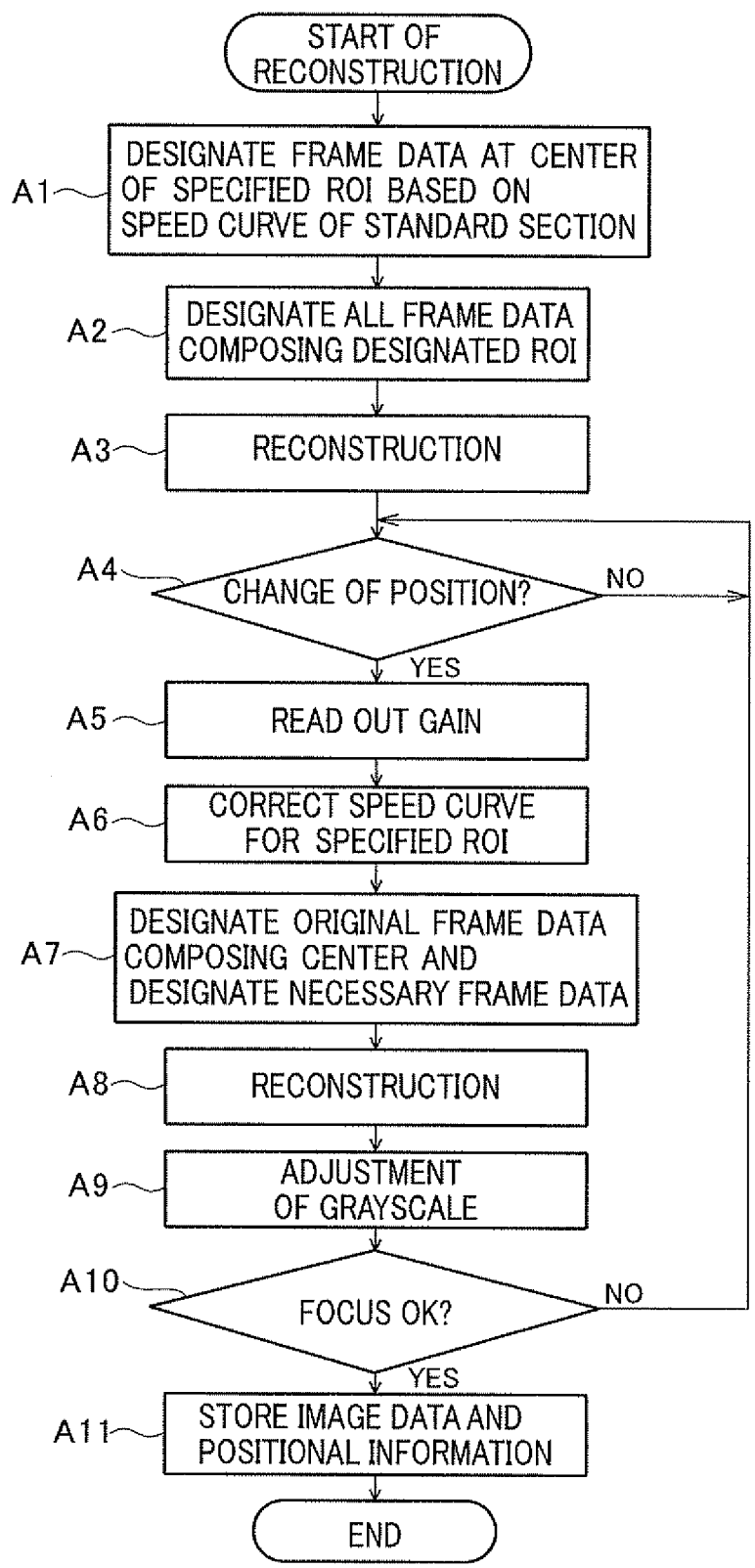
FIG. 11 is an outlined flowchart explaining the basic process for optimizing the focus according to the present invention.
Figure 12:
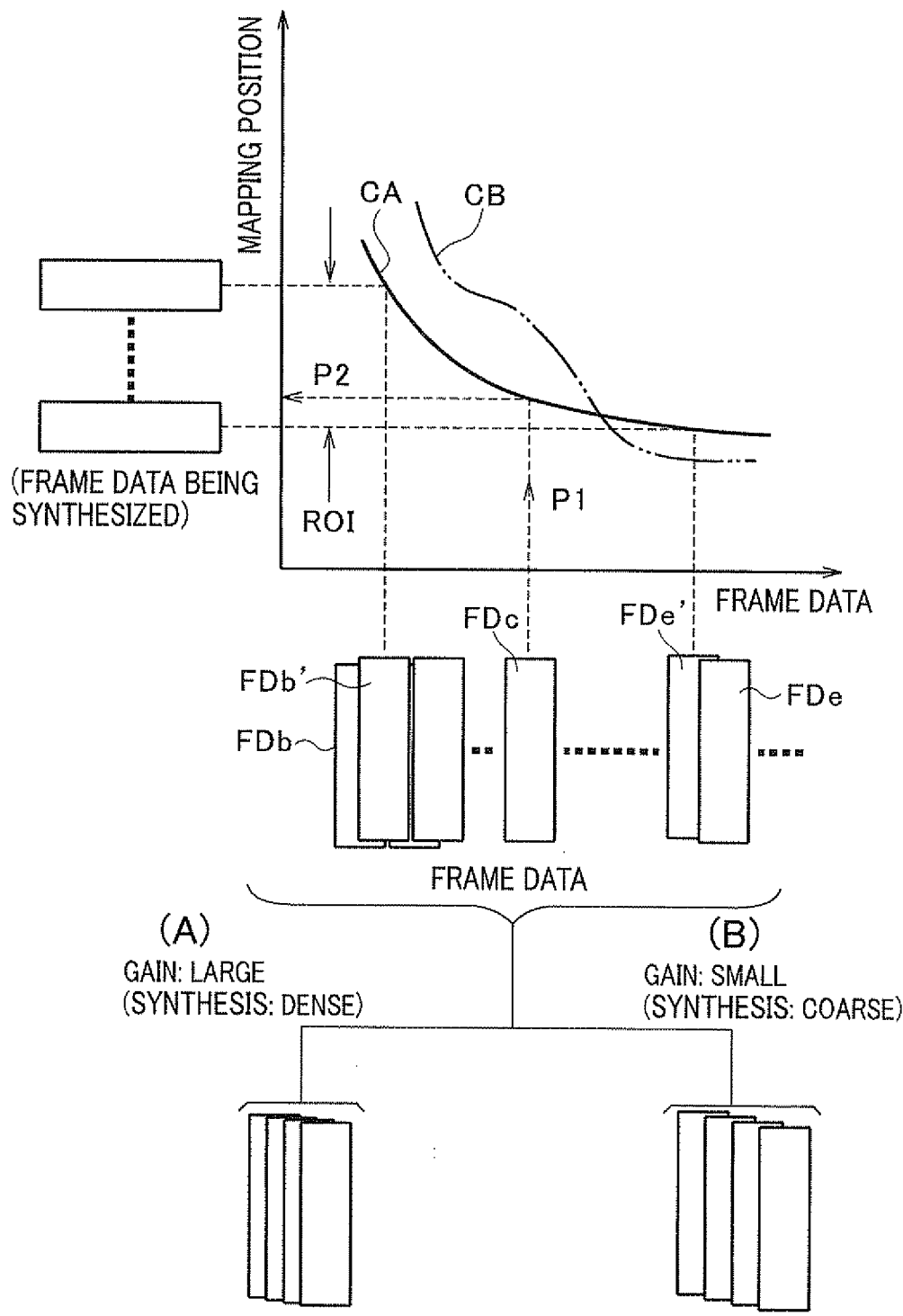
FIG. 12 is a view explaining synthesizing addition of frame data for optimizing the focus according to the present invention.
Figure 13:
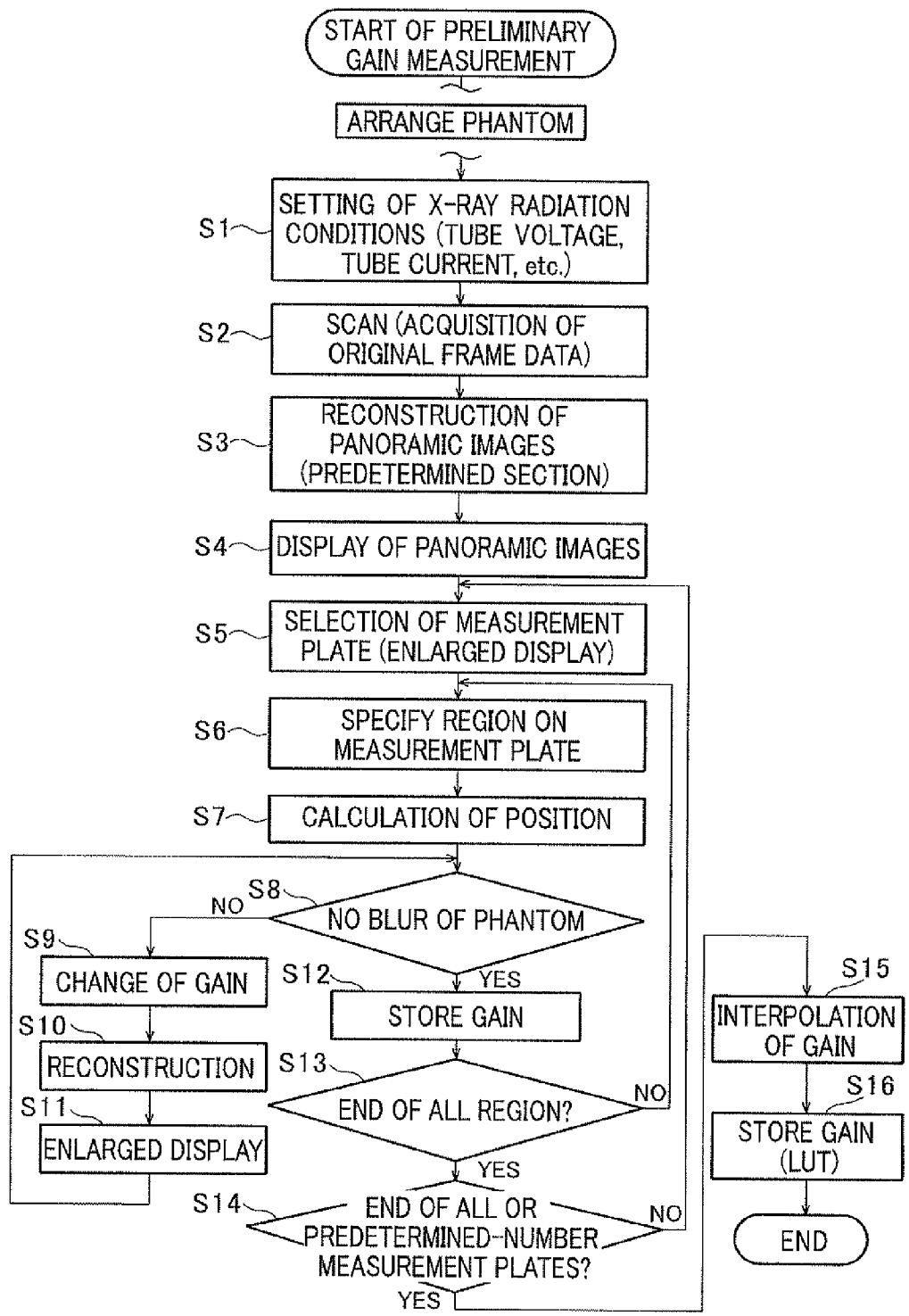
FIG. 13 is a flowchart explaining an outlined process for preliminary measuring the gain, which process is executed by a controller.
Figure 14:
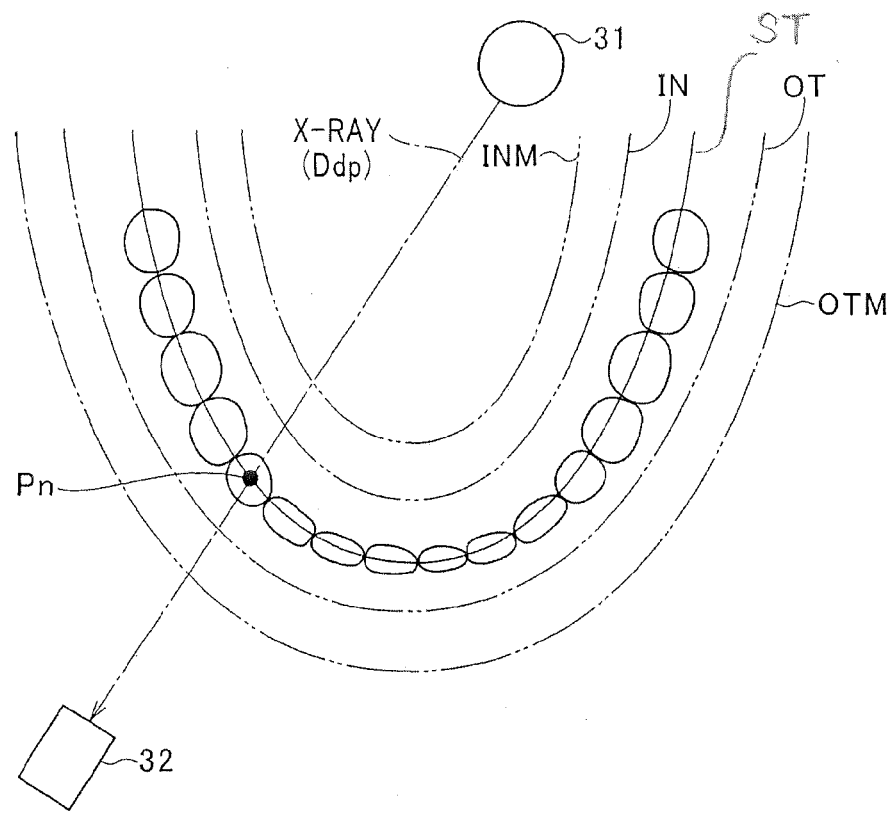
FIG. 14 illustrates the relationship between a plurality of sections along a tooth row and the directions (the depth directions) connecting an X-ray tube and a detector.
Figure 15:
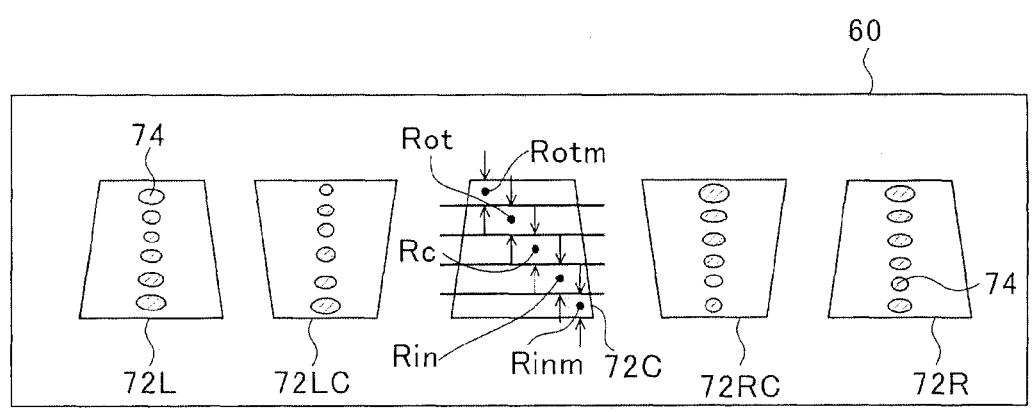
FIG. 15 illustrates measurement of an optimum gain at each position in each depth direction.
Figure 16:
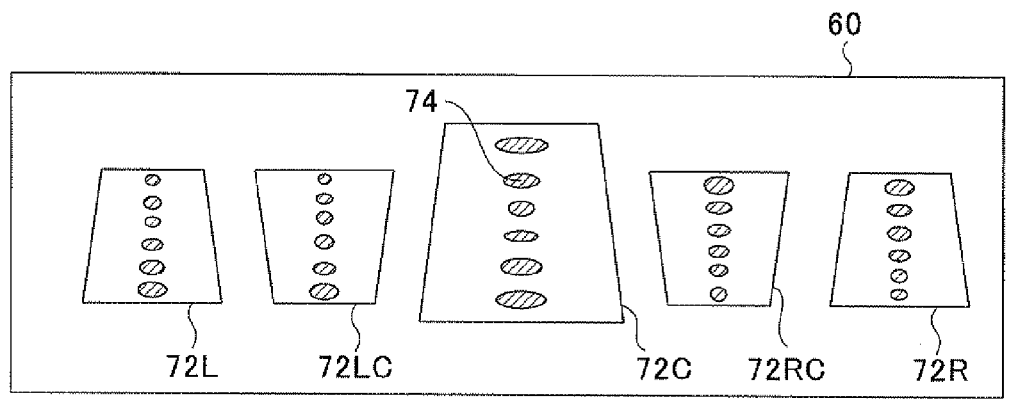
FIG. 16 further illustrates measurement of an optimum gain at each position in each depth direction.
Figure 17:
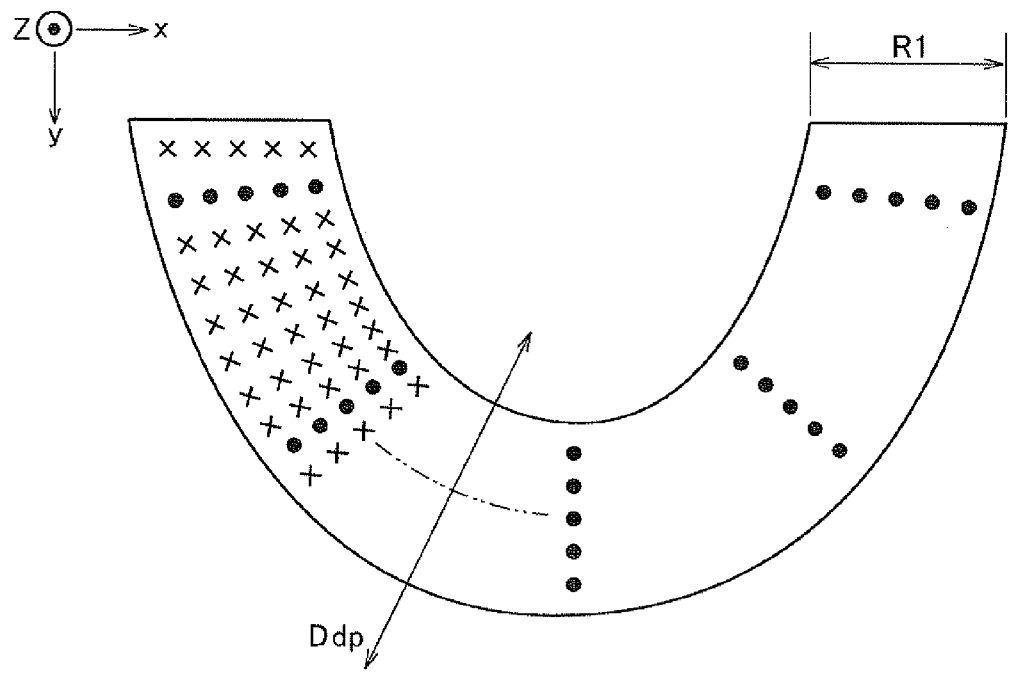
FIG. 17 is an illustration showing a three-dimensional distribution of gains to be measured.
Figure 18:
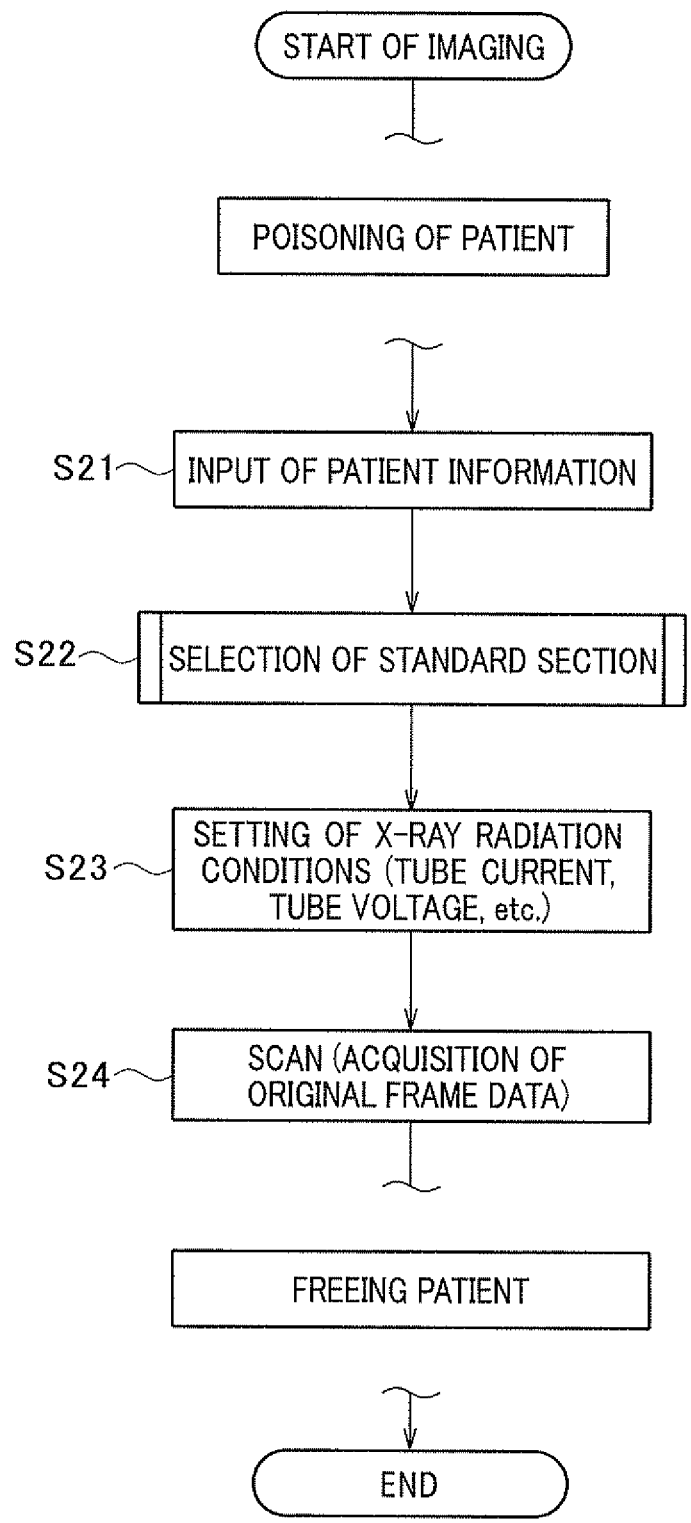
FIG. 18 is a flowchart explaining an outlined imaging process executed by a controller.
Figure 19:
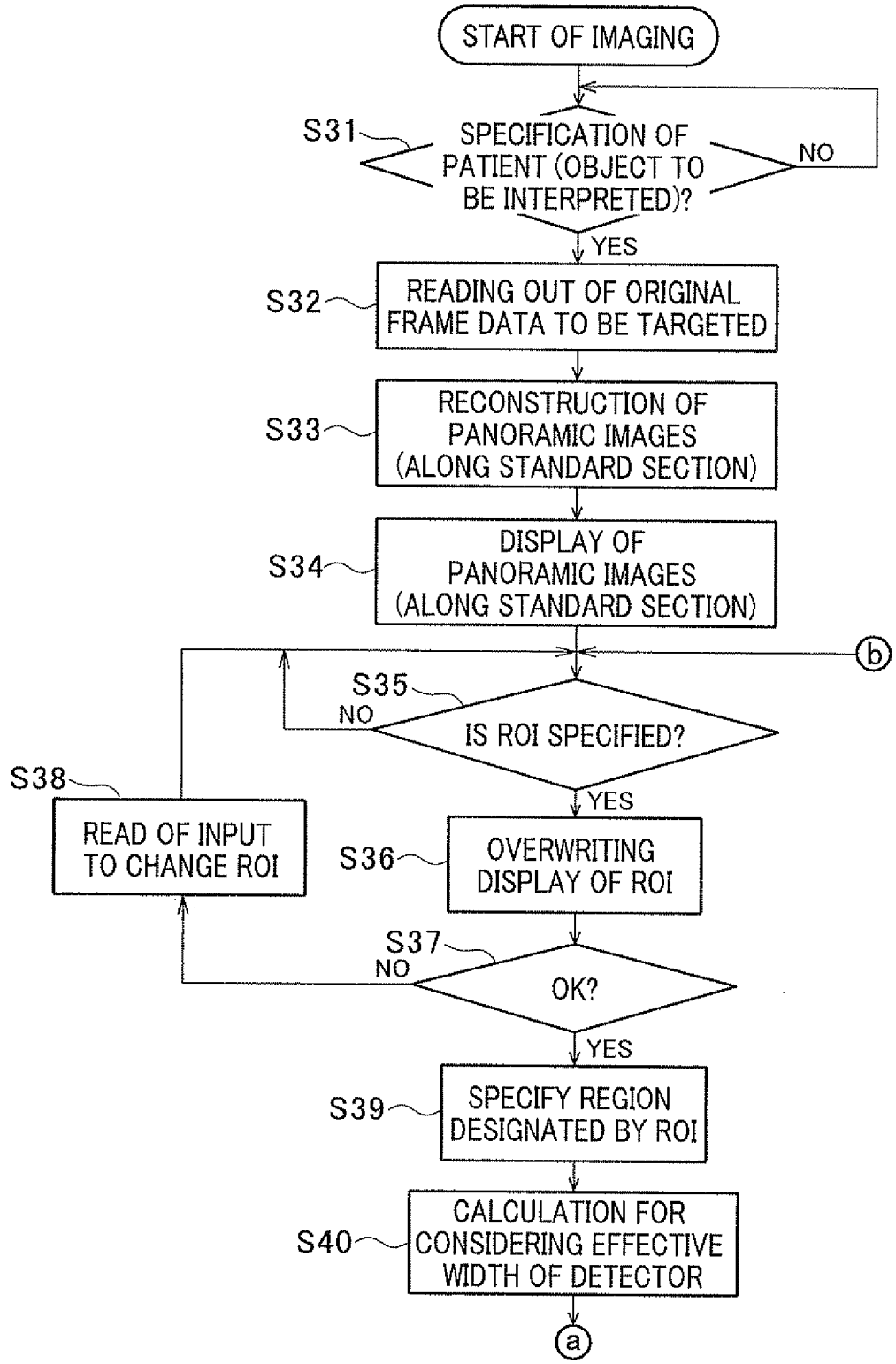
FIG. 19 is a flowchart exemplifying an outlined interpretation process executed by the controller.
Figure 20:
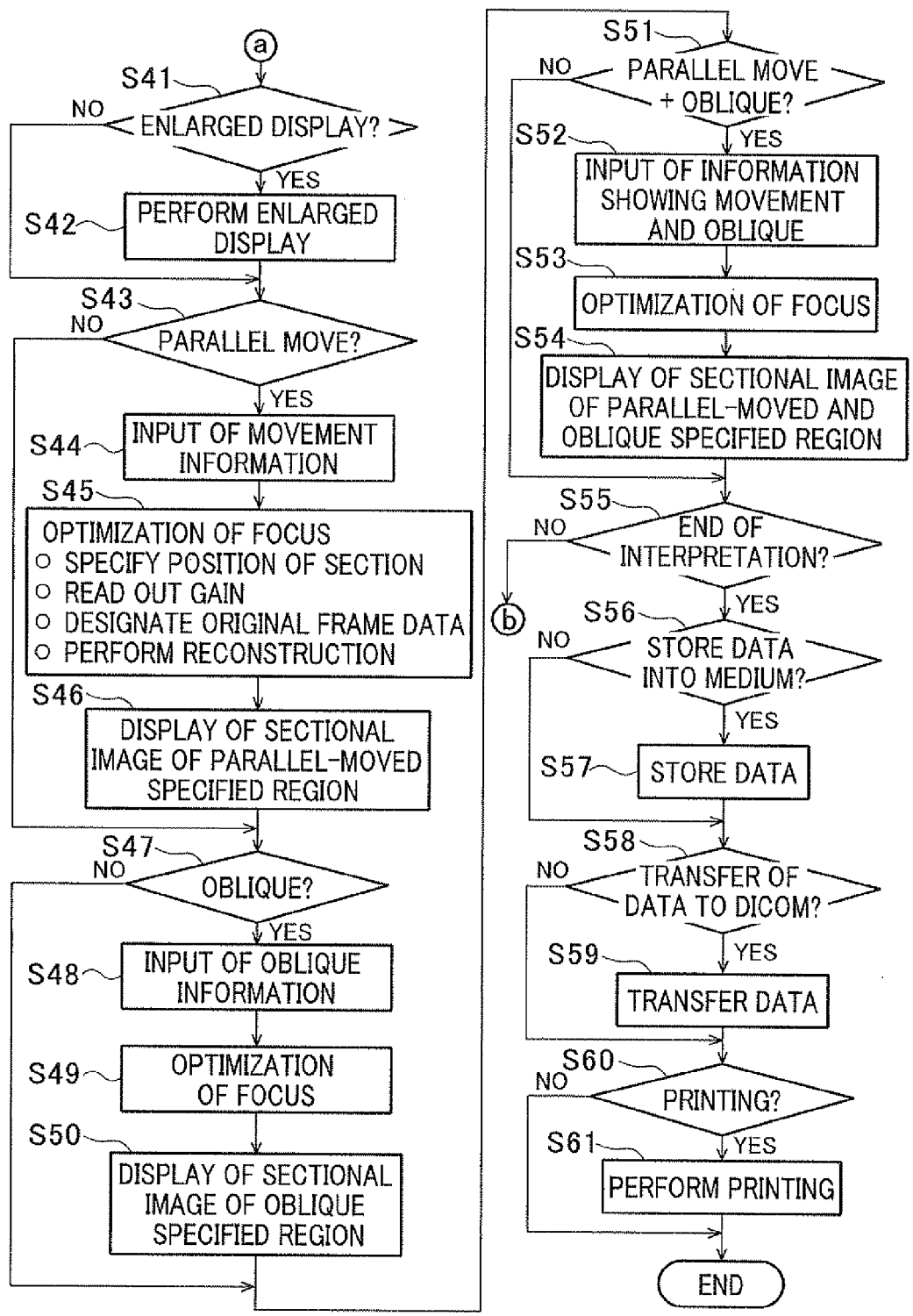
FIG. 20 is a flowchart exemplifying, together with FIG. 19, the outlined interpretation process executed by the controller.
Figure 21:
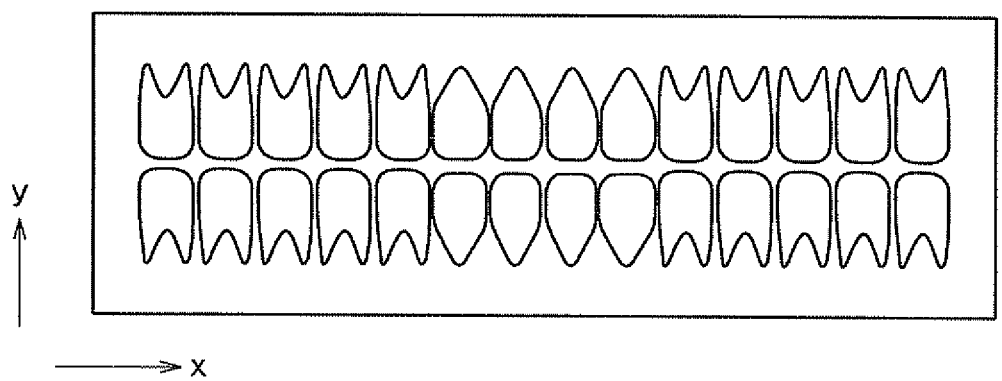
FIG. 21 is a screen view pictorially showing a panoramic image of a standard section.
Figure 22:
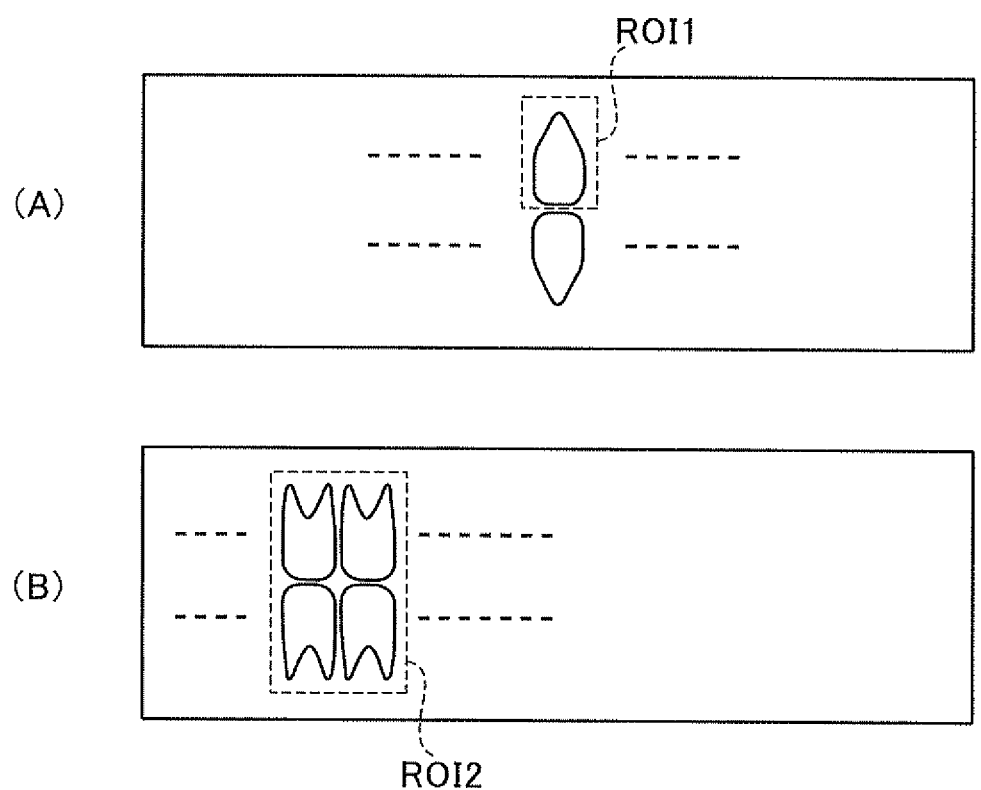
FIG. 22 shows screen views exemplifying various ROIs which can be specified on the panoramic image.
Figure 23:
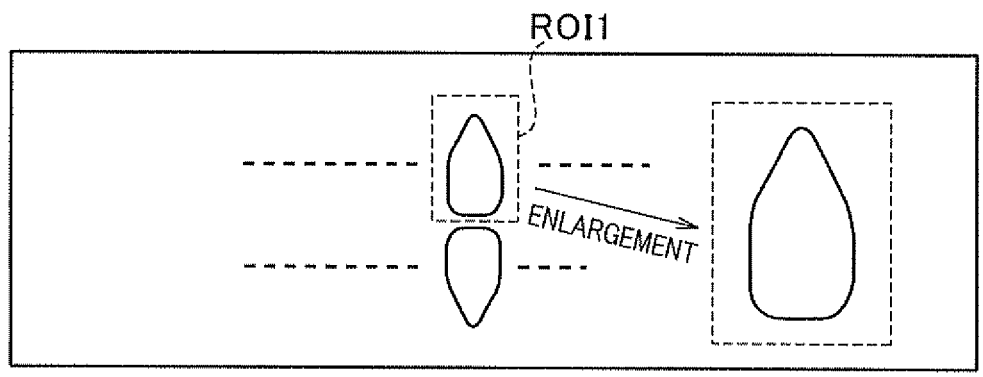
FIG. 23 is a screen view exemplifying the display of an enlarged view of the part (section) of a ROI specified on the panoramic image.
Figure 24:
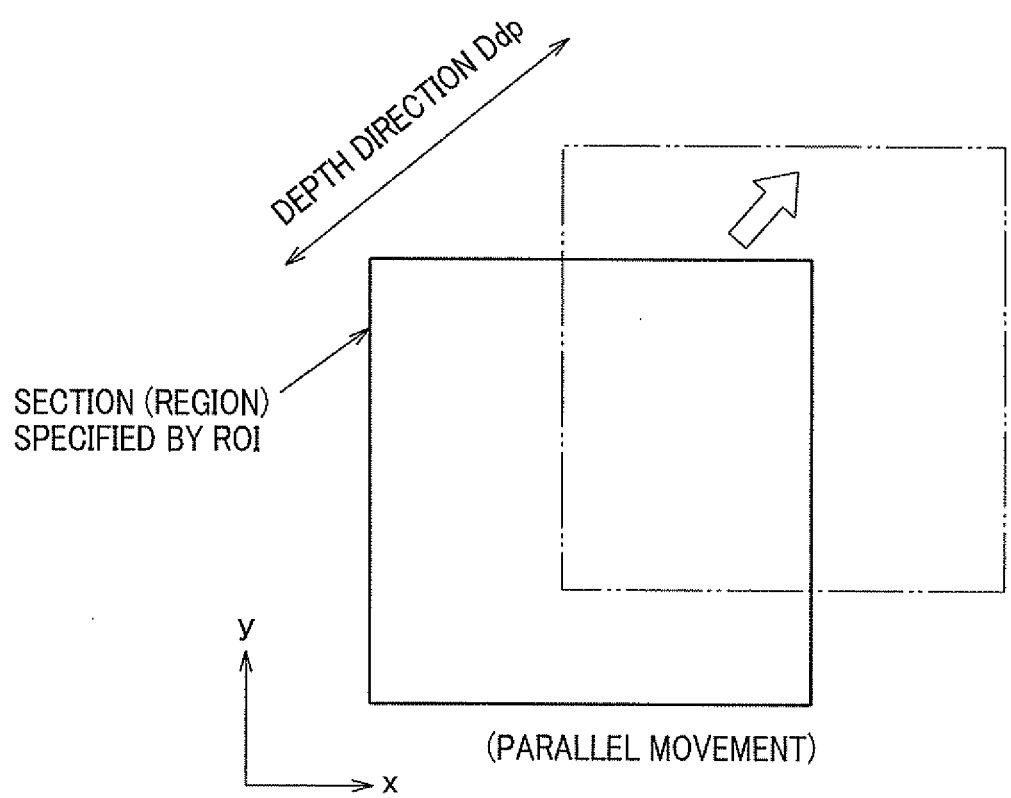
FIG. 24 is a view explaining a concept to move a section specified by a ROI on the panoramic image in parallel with the depth direction.
Figure 25:
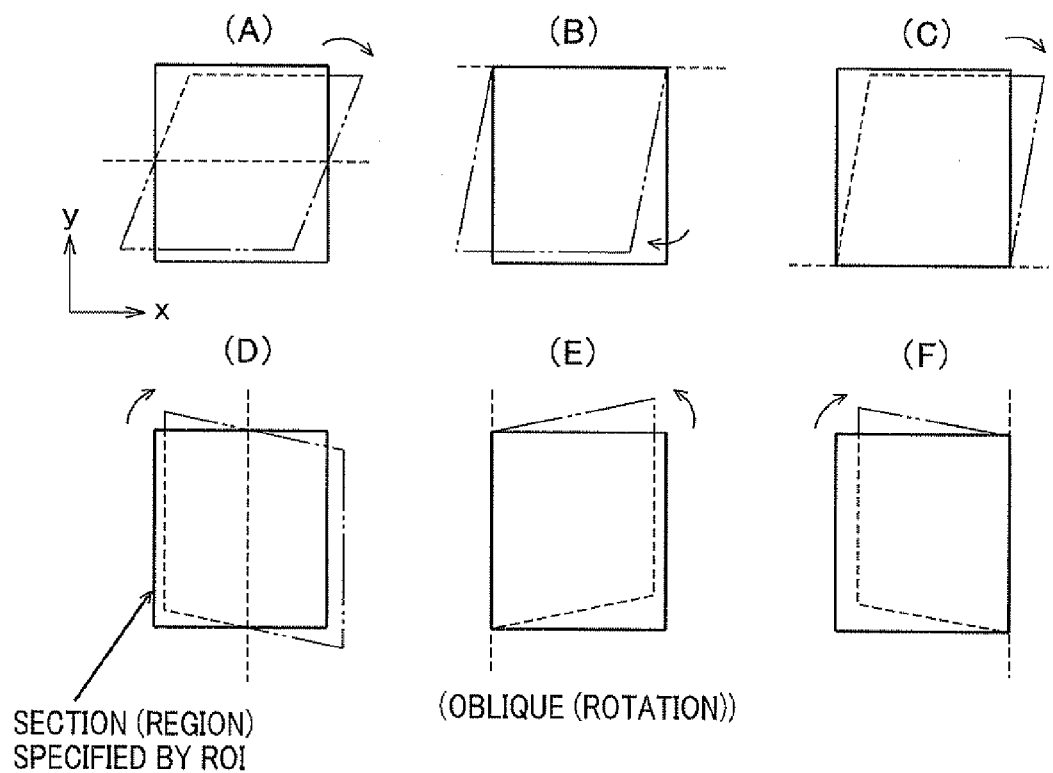
FIG. 25 shows views explaining a concept to tilt (rotate) a section specified by a ROI on the panoramic image.
Figure 26:
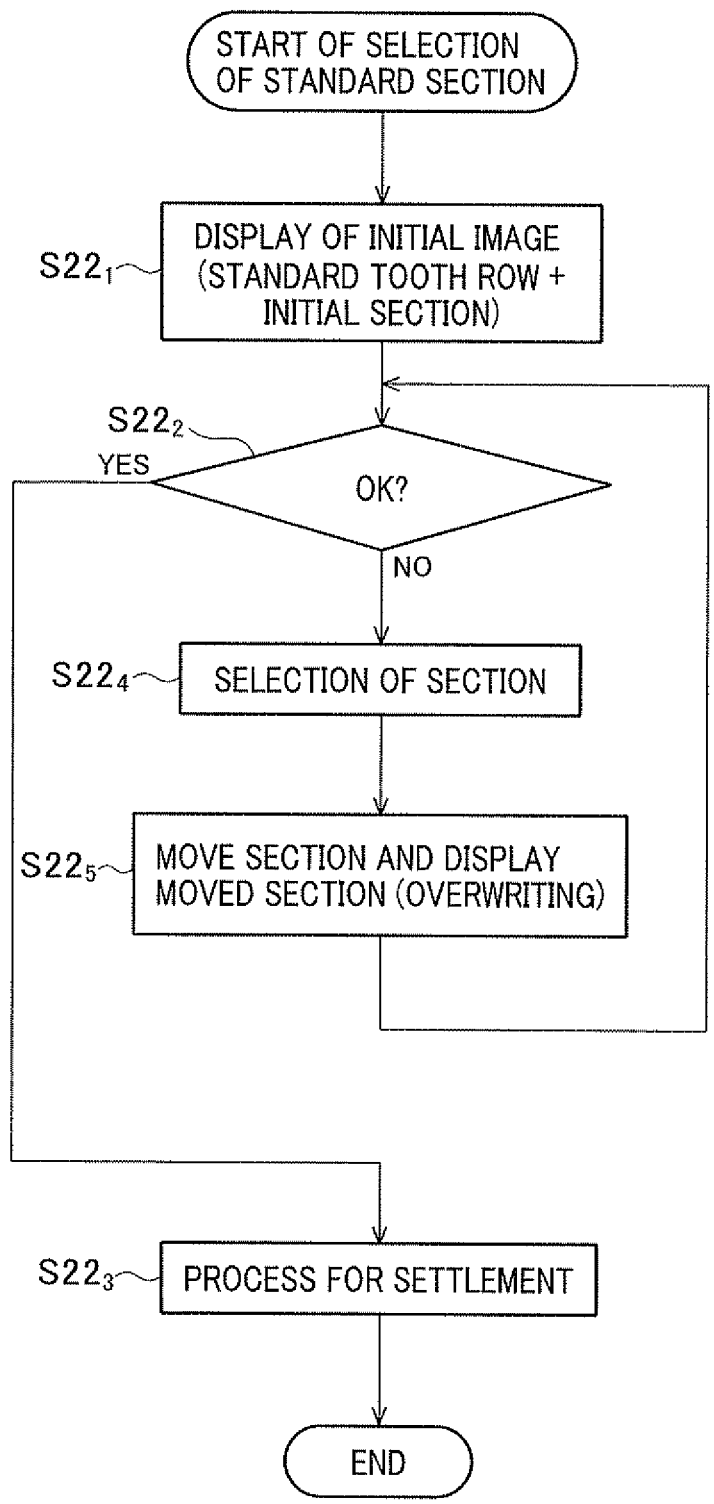
FIG. 26 is a flowchart explaining an outlined selection process of the standard section, which is executed by the controller.
Figure 27:
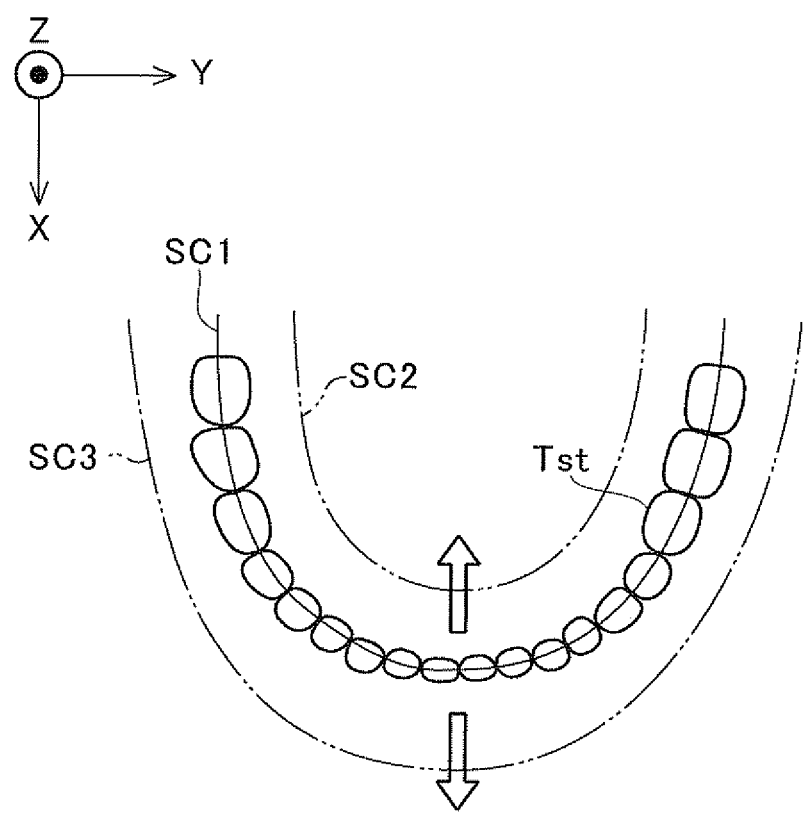
FIG. 27 is a view conceptually explaining the selection of the standard section.
Figure 28:
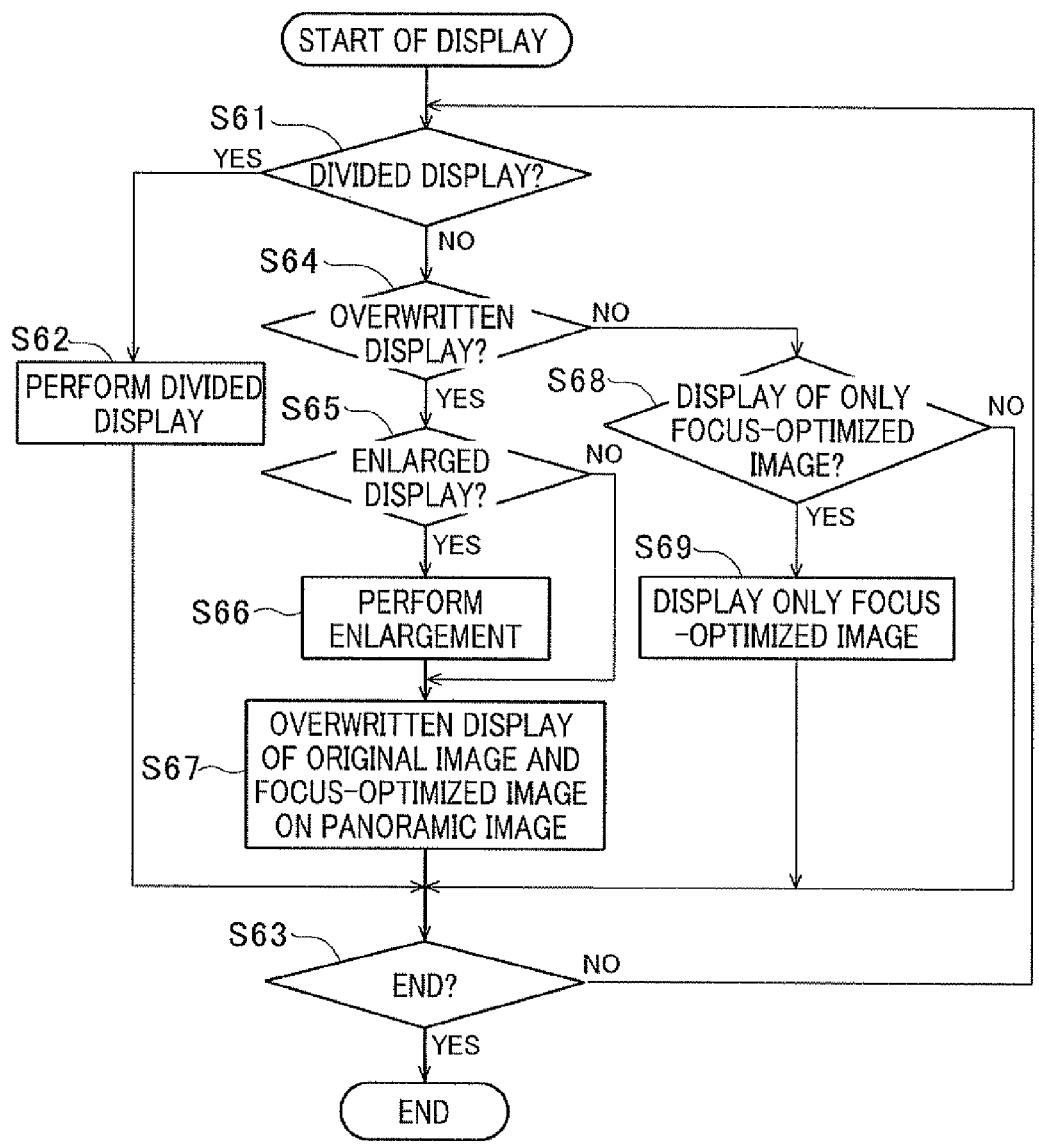
FIG. 28 is a flowchart exemplifying a selection process for display modes used to display a sectional image specified by the ROI.
Figure 29:
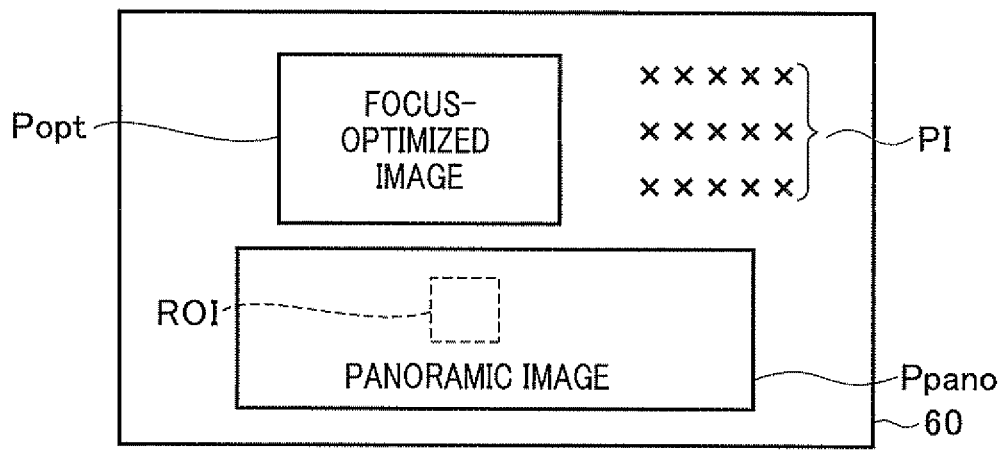
FIG. 29 is a screen view exemplifying a displayed image of a section specified by the ROI.
Figure 30:
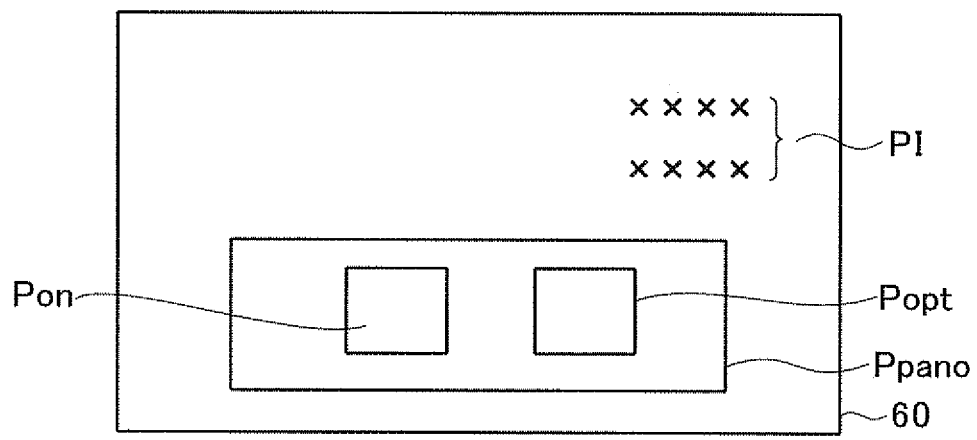
FIG. 30 is a screen view exemplifying another displayed image of a section specified by the ROI.
Figure 31:
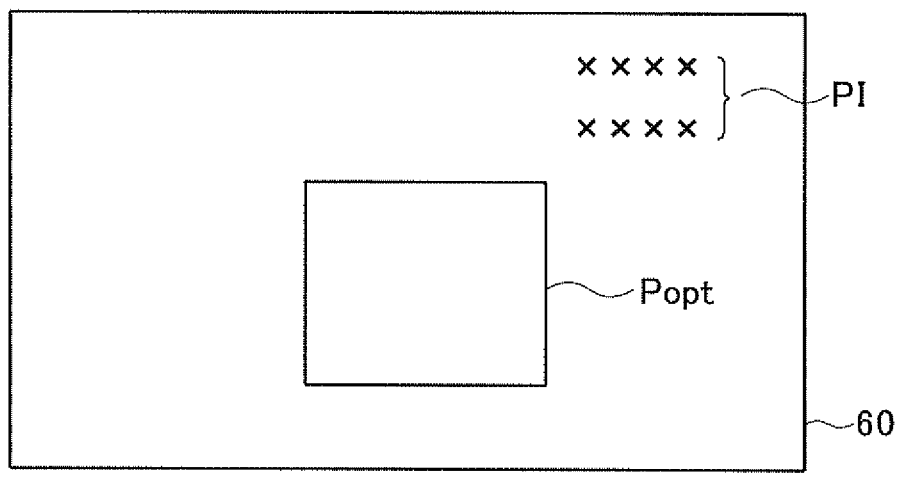
FIG. 31 is a screen view exemplifying another displayed image a section specified by ROI.
Figure 32:
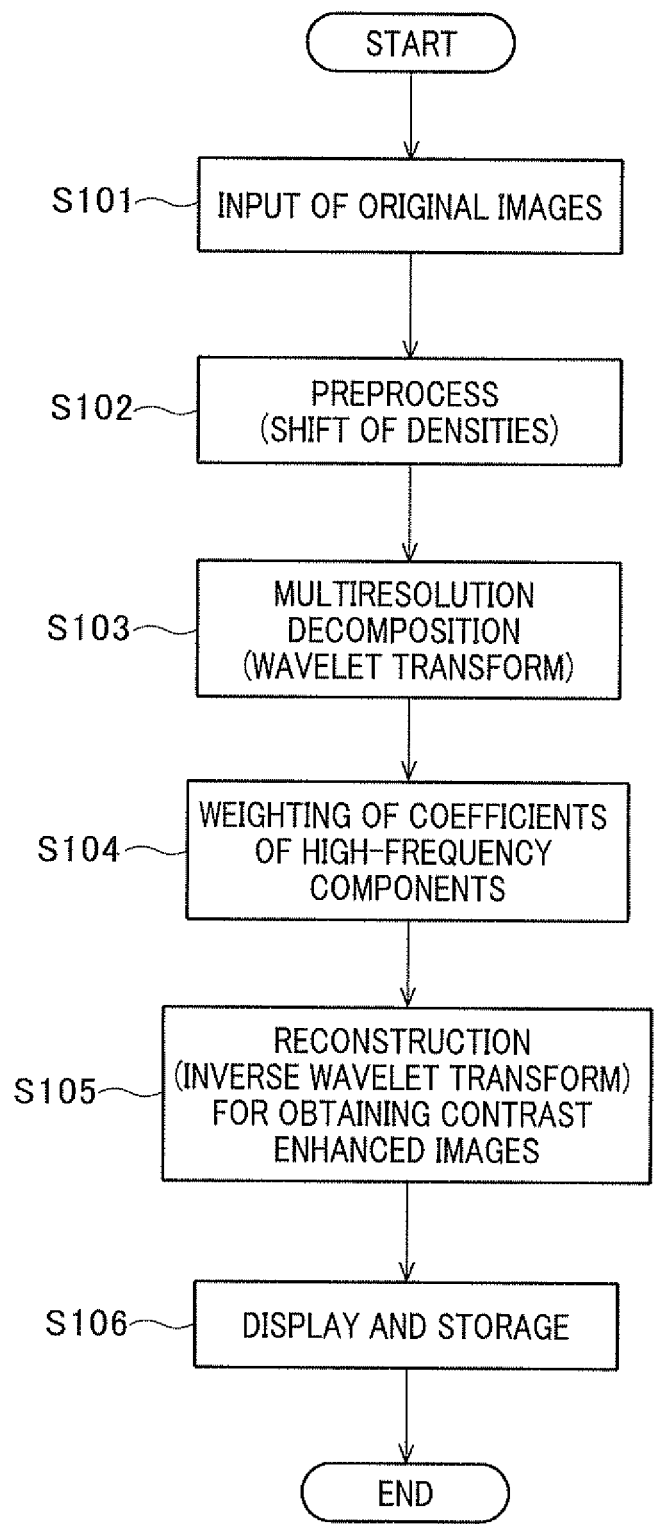
FIG. 32 is a flowchart outlining an automated contrast enhancement process executed by an image processor employed by a second embodiment of the panoramic imaging apparatus according to the present invention.
Figure 33:
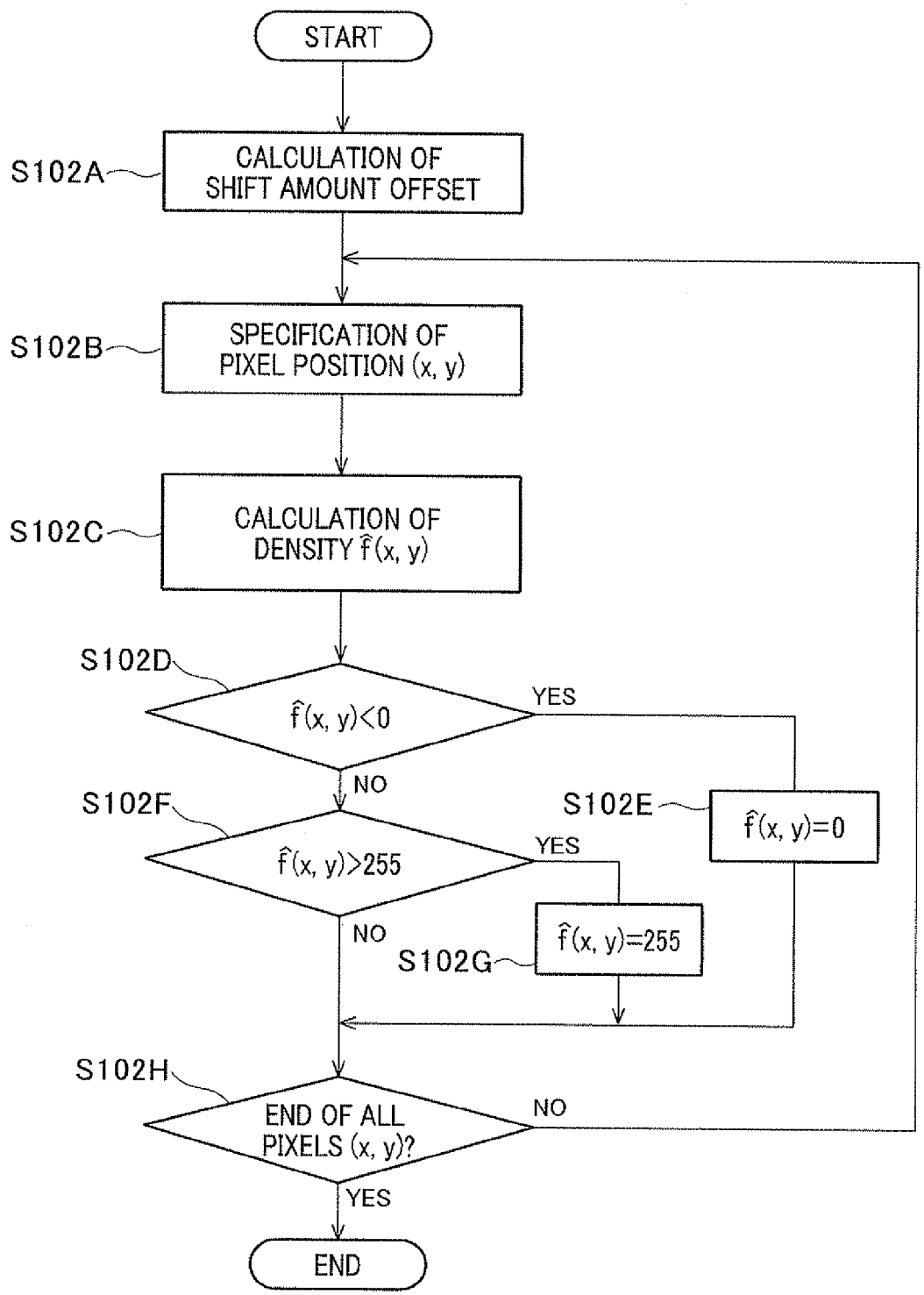
FIG. 33 is a flowchart outlining a density shift executed by the image processor in cooperation with the controller.
Figure 34:
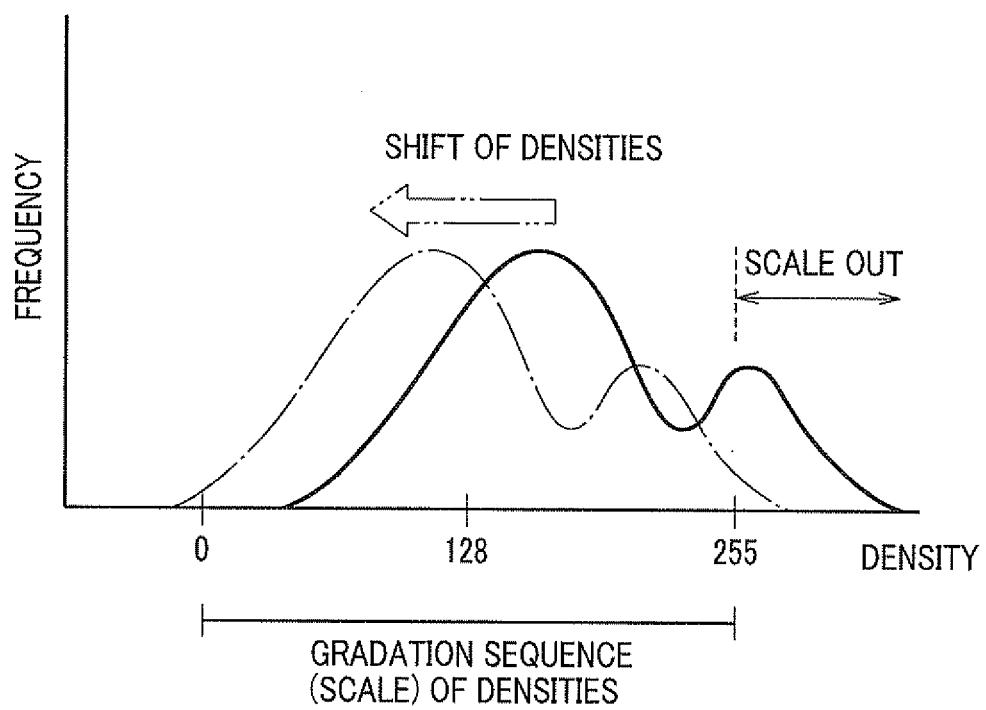
FIG. 34 is a view explaining the relationship between scale out and the density shift.
Figure 35:
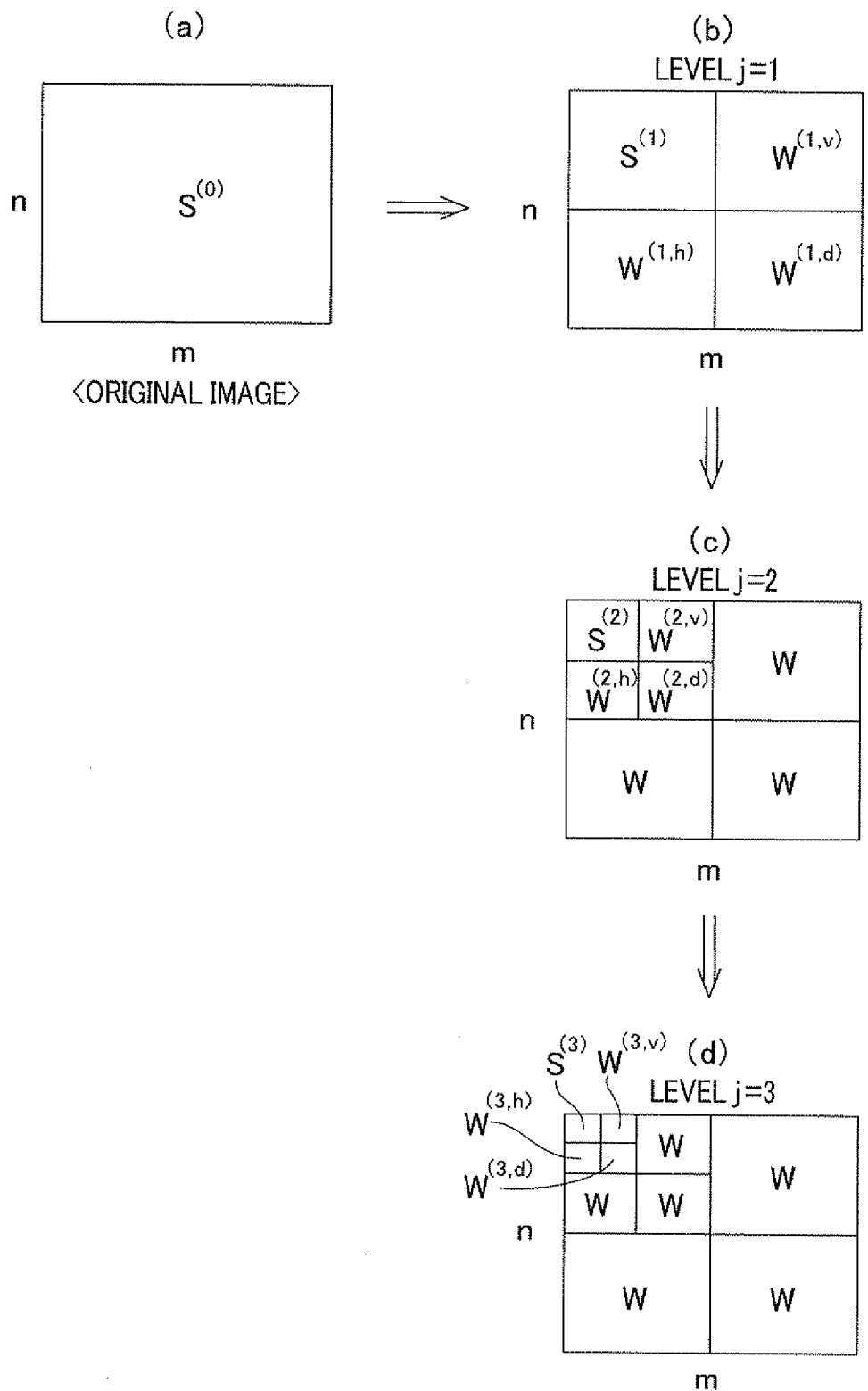
FIG. 35 is a pictorial illustration explaining each level of the wavelet transform which serves as a multiresolution analysis.
Figure 36:
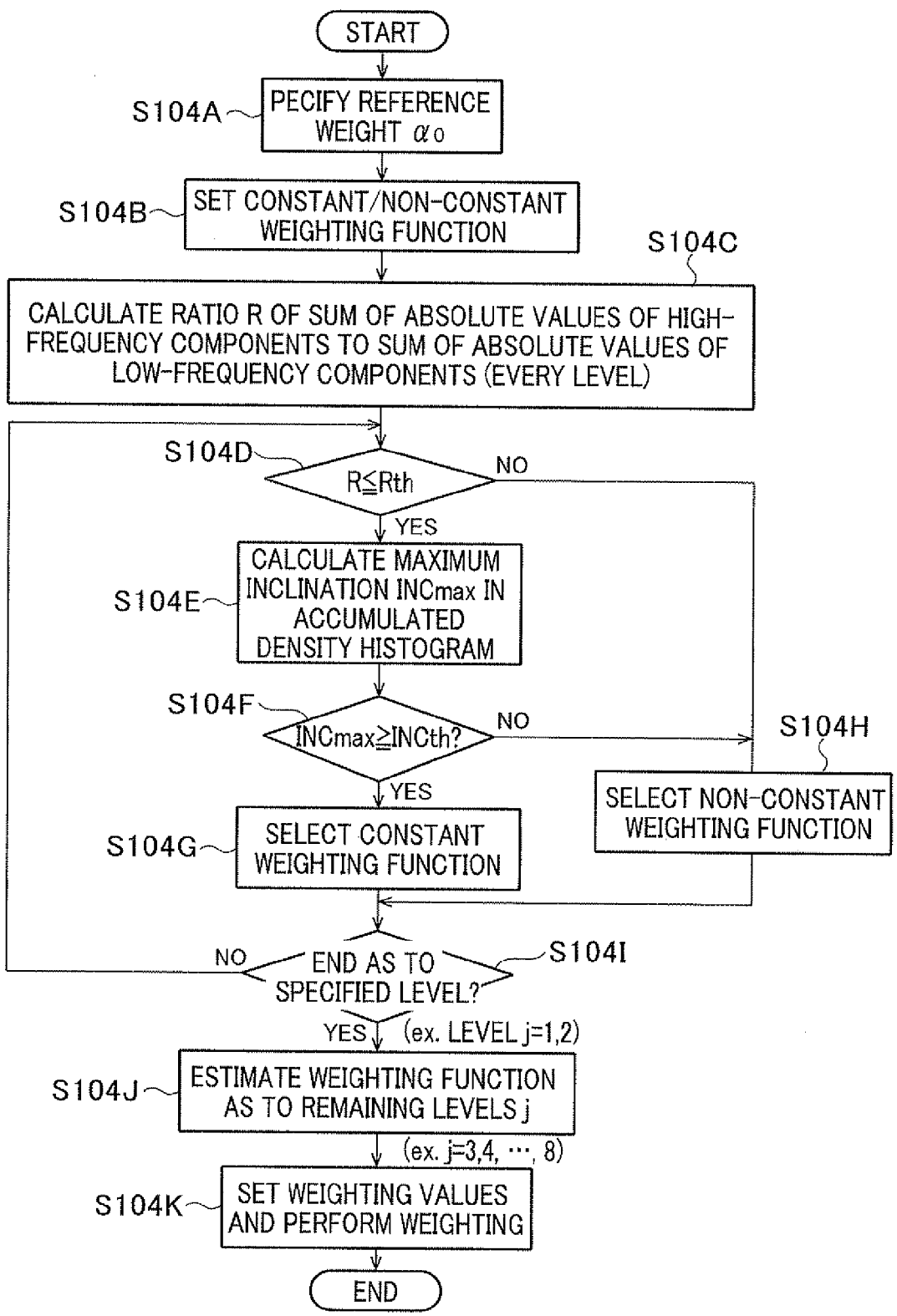
FIG. 36 a flowchart outlining an automated weighting process executed by an image processor.
Figure 37:
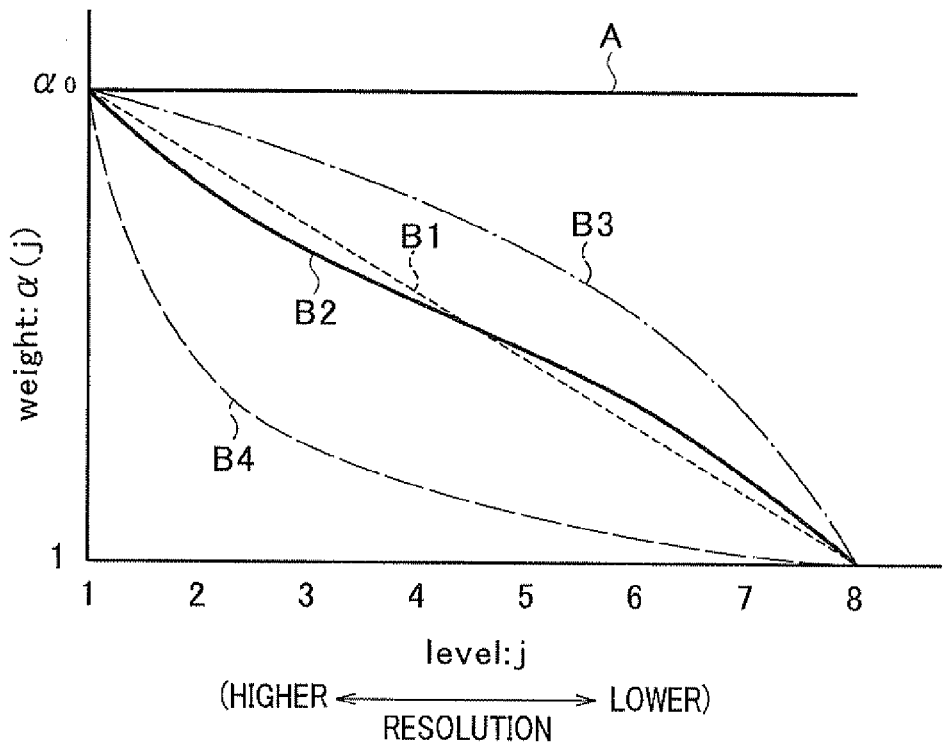
FIG. 37 is a graph exemplifying a plurality of weighting functions for high-frequency components at the respective levels, which are obtained by the wavelet transform.
Figure 38:
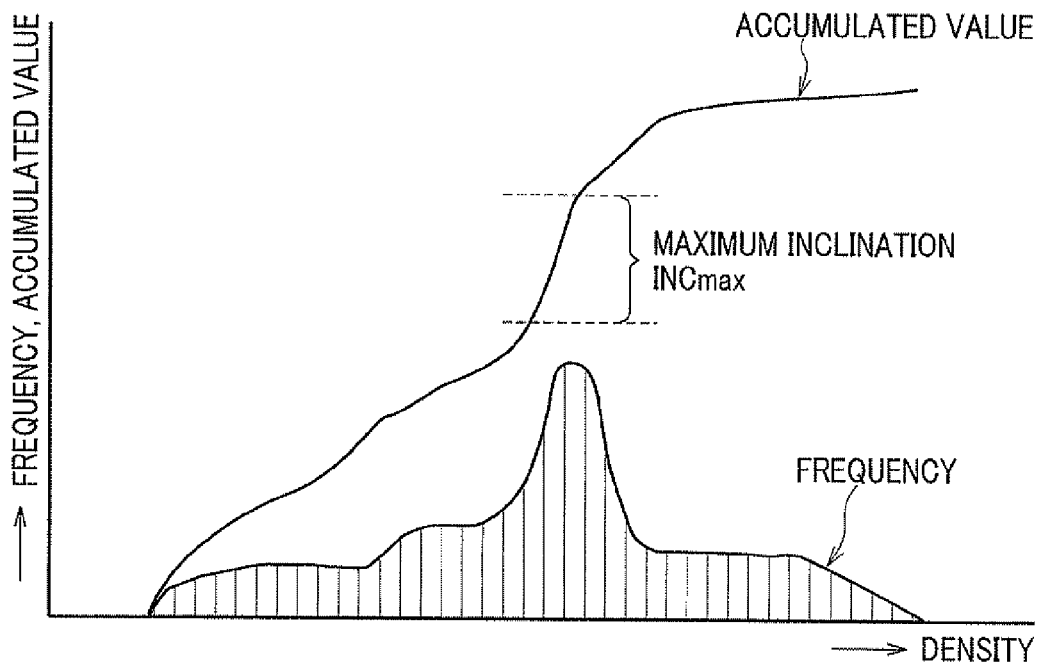
FIG. 38 is a view qualitatively explaining the relationship between a density histogram and a maximum gradient of an accumulated density histogram.
Figure 39:
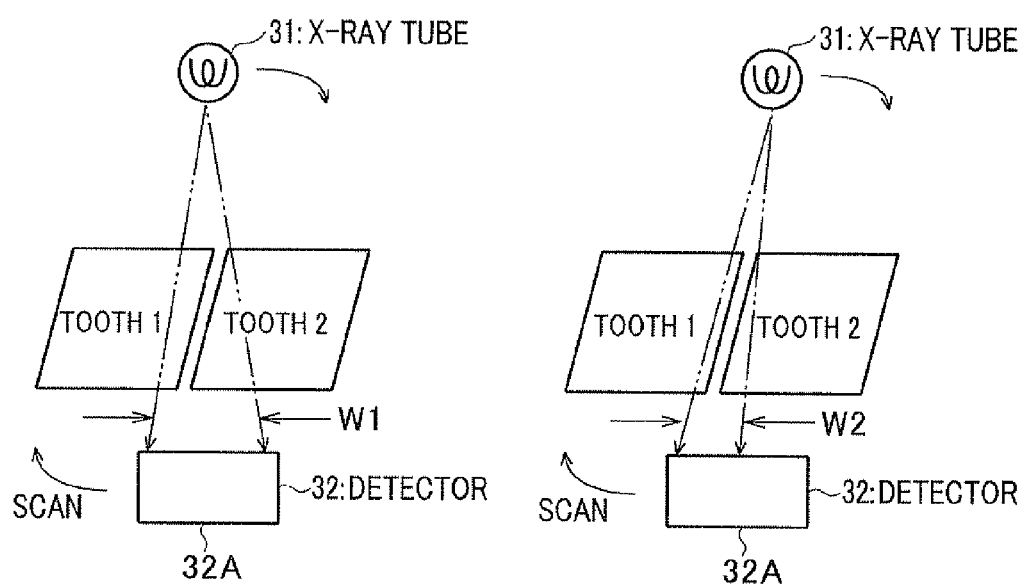
FIG. 39 explains merits and demerits of control of the effective width of a detector, which is executed, together with an image processor, by a controller employed by a third embodiment of the panoramic imaging apparatus according to the present embodiment.
Figure 40:
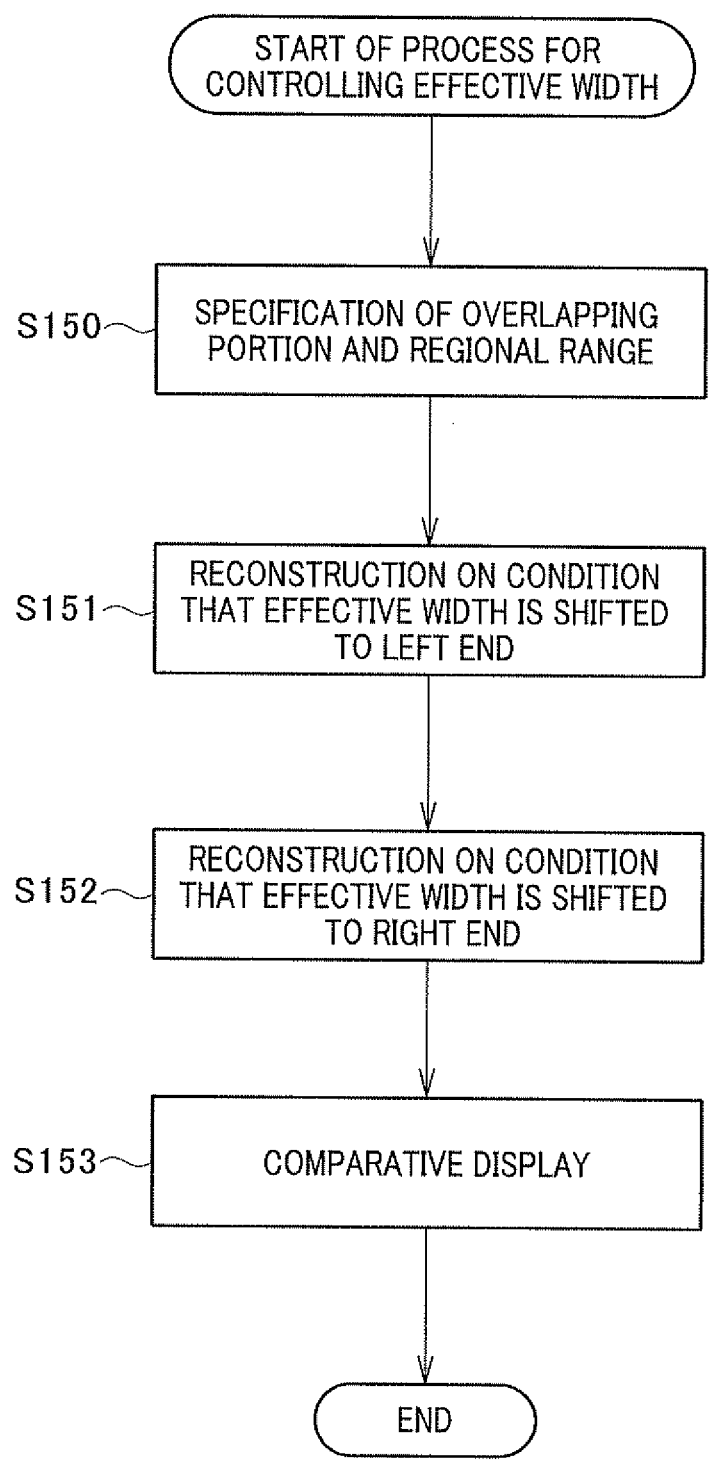
FIG. 40 is a flowchart outlining control of the effective width of the detector, which is executed together with the image processor by the controller in the third embodiment.
Figure 41:
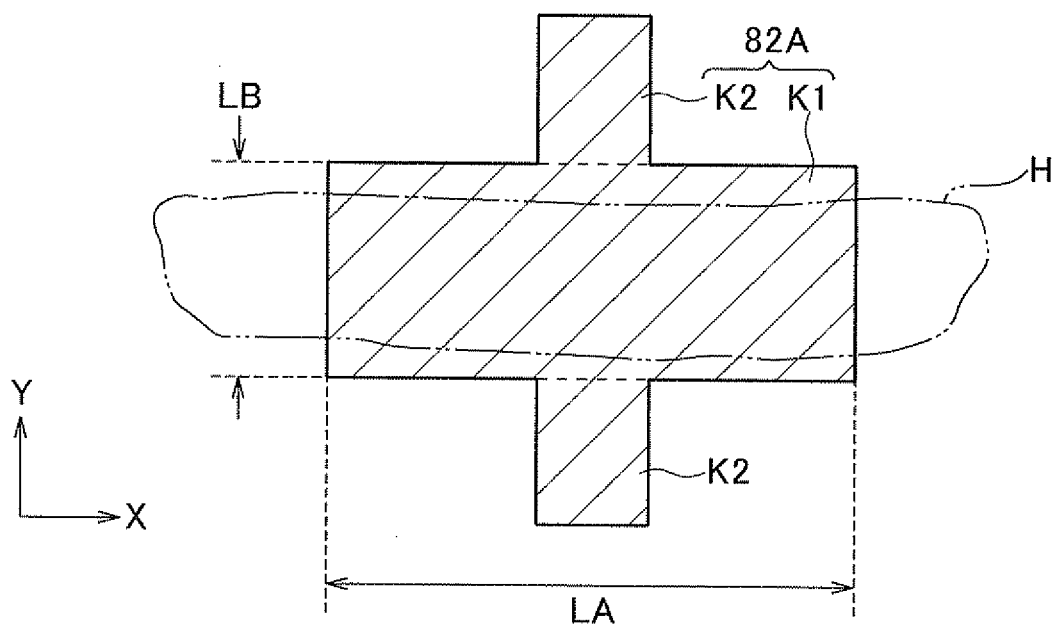
FIG. 41 is a view explaining a two-dimensional X-ray incident area of a detector employed by a fourth embodiment of the panoramic imaging apparatus according to the present invention.
Figure 42:
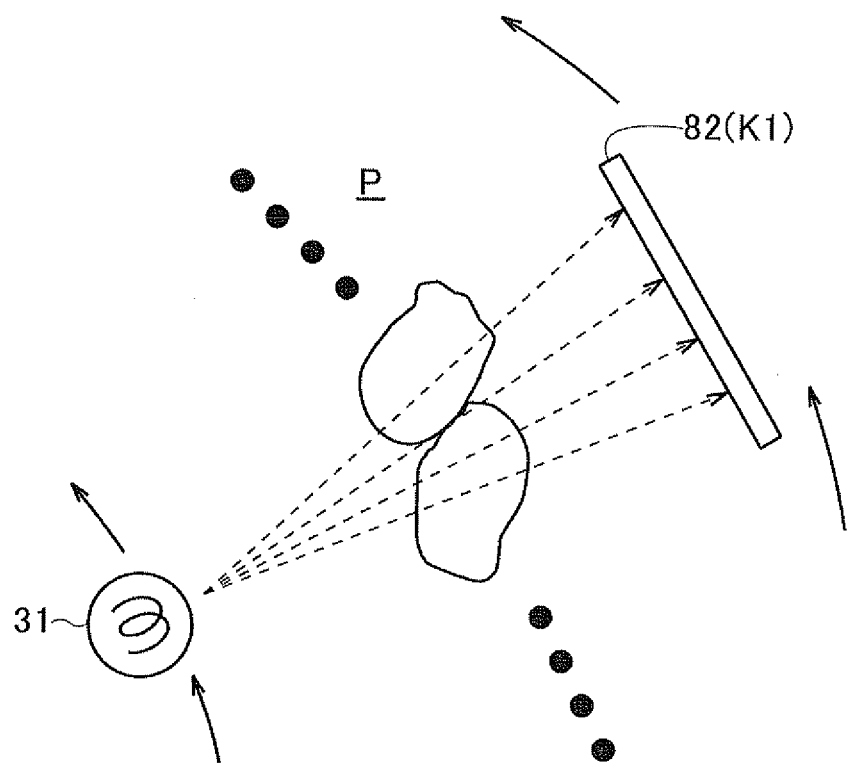
FIG. 42 is a view explaining the relationship synthesis of adjacent teeth and X-ray paths.
Figure 43:
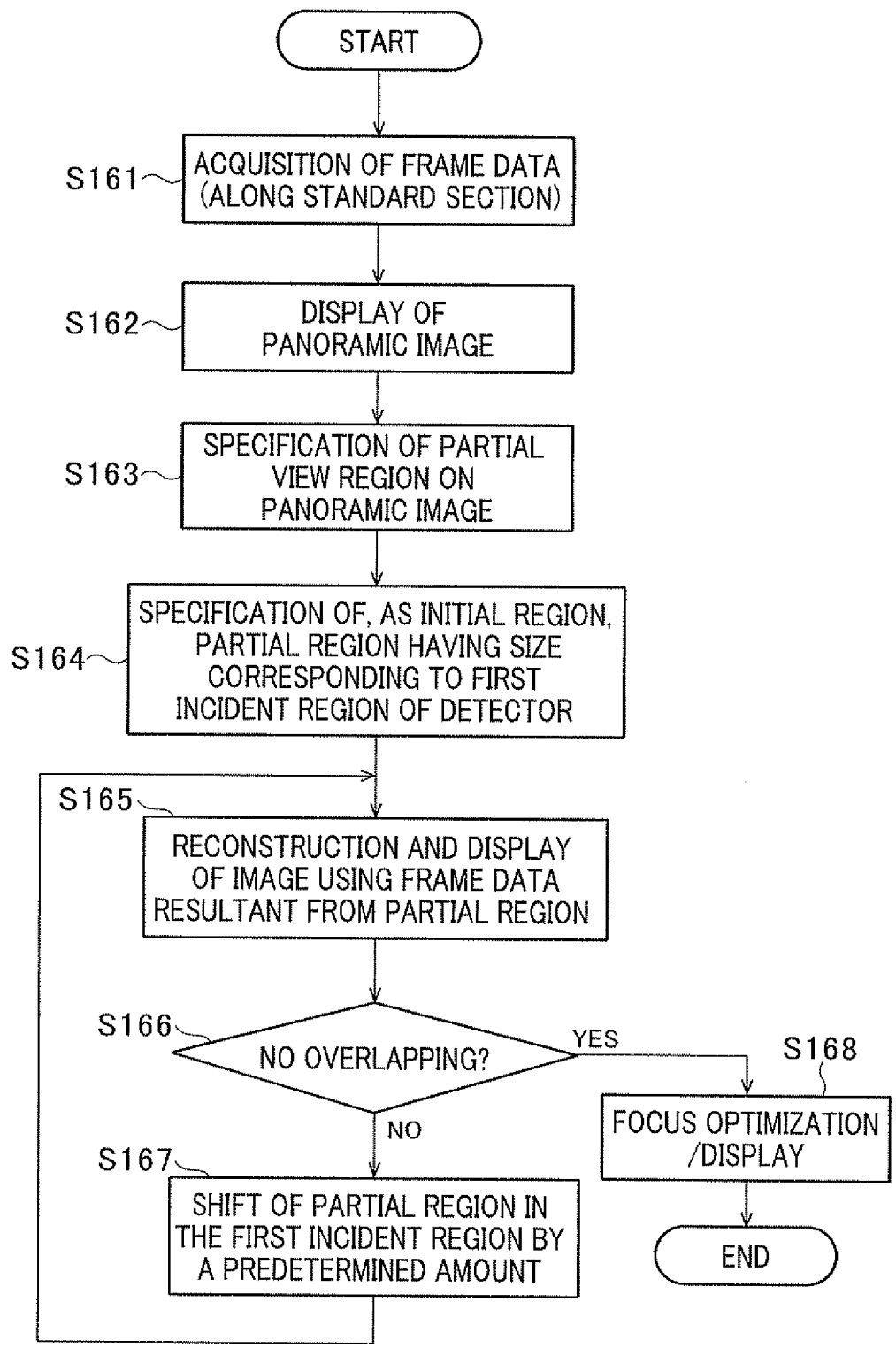
FIG. 43 is a flowchart outlining a process to search a gap in the synthesized portion of the adjacent teeth, which process is executed by a controller employed by the fourth embodiment.
Figure 44:
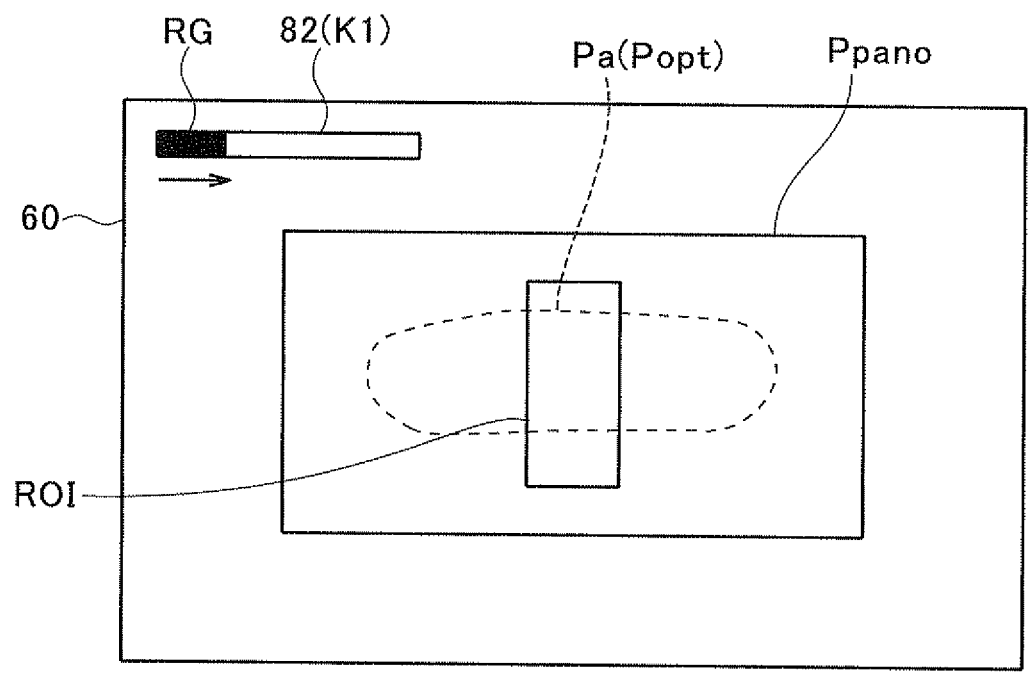
FIG. 44 is a view showing an image to be displayed through the process to search the synthesized portion of the adjacent teeth in the fourth embodiment.

DESCRIPTION OF REFERENCES 1 panoramic imaging apparatus
11 chassis
12 computer
14 imaging unit
23 up-and-down unit
24 rotation unit
30 rotation drive mechanism
31 X-ray tube
32 detector
41 high-voltage generator
53 buffer memory
54 image memory
55 frame memory
56 image processor
57 controller
58 operation device
60 monitor
82 detector
P object to be examined
FT phantom

The invention claimed is:

1. A panoramic imaging apparatus characterized in that the apparatus comprises:

an X-ray source radiating an X-ray;

a detector outputting a digital electrical signal depending on an incident X-ray at a constant frame rate;

movement means for moving a pair of the X-ray source and the detector around an object in a state where the X-ray source and the detector are opposed to each other with the object located therebetween;

storage means for storing, as frame data, the electrical signal outputted by the detector at the constant frame rate while the movement means moves the X-ray source and the detector around the object;

panoramic image producing means for producing a panoramic image of a predetermined section of the object from the frame data stored in the storage means;

partial sectional image producing means for producing a partial sectional image from the frame data, the partial sectional image focusing on a specified section three-dimensionally and arbitrarily specified based on a partial region indicated on the panoramic image, the specified section being located in a space previously set to enclose the predetermined section and to enable the X-ray to pass therethrough, and preliminary measurement means for previously measuring correspondence information between three-dimensional positions in the space and gains, the gains being defined as gradients at points on a curve in a coordinate system defined by both the plurality of frame data and mapping positions to map the frame data in a memory space so as to reconstruct a panoramic image, wherein the panoramic image producing means is configured to produce the panoramic image by making reference to the correspondence information depending on a position of the predetermined section in the space, and the partial sectional image producing means is configured to produce the partial sectional image by making reference to the correspondence information depending on a position of the specified section.

2. The panoramic imaging apparatus of claim 1, wherein the movement means is configured to move the pair of the X-ray source and the detector so as to focus on the predetermined section, the preliminary measurement means comprising means for setting the correspondence information in relation to the predetermined section from the frame data read out of the storage means, and means for calculating, as three-dimensional information, the correspondence information at respective positions in the space, based on the correspondence information of the predetermined section.

3. The panoramic imaging apparatus of claim 2, wherein the detector comprises a line-shaped detection face to receive the X-ray, and the gains are given such that, among the respective positions in the space, positions on a line parallel with the detection face of the detector are given the same value of the gains.

4. The panoramic imaging apparatus of claim 1, wherein the panoramic image producing means comprises panoramic image displaying means for displaying the panoramic image of the predetermined section, and the partial sectional image producing means comprises a region-of-interest setting means for interactively allowing a user to set, as the partial region, a partial region of interest on the panoramic image displayed by the panoramic image displaying means, reception means for interactively receiving the gain of a section formed by the region of interest, gain obtaining means for obtaining a gain in accordance with section converting information from the predetermined section converging information by referring to the correspondence information, and partial sectional image calculating means for calculating, as the partial sectional image, an image depending on the section converting information on the basis of the gain obtained by the gain obtaining means and the frame data.

5. The panoramic imaging apparatus of claim 4, comprising partial sectional image displaying means for superposing, on the panoramic image, the partial sectional image calculated by the partial sectional image calculating means on the panoramic image.

6. The panoramic imaging apparatus of claim 1, wherein the preliminary measurement means comprises preliminary imaging means for imaging panoramic image a phantom device with a phantom, the phantom device being placed, the phantom being used for measuring distances from the predetermined section in each of liner direction each connecting the X-ray source and the detector during the movement thereof;

means for setting the gains necessary at the distances by allowing an operator to visually observe the phantom imaged in the panoramic image provided by the preliminary imaging means; and means for storing, into a memory, correspondence information between the distances and the gains which have been set.

7. The panoramic imaging apparatus of claim 6, wherein the phantom device comprises a base member, an oblique plate which is oblique to the base member at a predetermined angle, and a plurality of phantoms arranged along the oblique plate at intervals.

8. The panoramic imaging apparatus of claim 7, wherein the plurality of phantoms are granular substances made of non-transmissive material to the X-rays.

9. The panoramic imaging apparatus of claim 6, wherein the phantom device comprises a base member, an oblique plate which is oblique to the base member at a predetermined angle, and a strip-shaped phantom arranged along the oblique plate.

10. A panoramic imaging apparatus comprising:

an X-ray source radiating an X-ray;

a detector outputting a digital electrical signal depending on an incident X-ray at a constant frame rate;

movement means for moving a pair of the X-ray source and the detector around an object in a state where the X-ray source and the detector are opposed to each other with the object located therebetween;

storage means for storing, as frame data, the electrical signal outputted by the detector at the constant frame rate while the movement means moves the X-ray source and the detector around the object;

panoramic image producing means for producing a panoramic image of a predetermined section of the object from the frame data stored in the storage means;

partial sectional image producing means for producing a partial sectional image from the frame data, the partial sectional image focusing on a specified section three-dimensionally and arbitrarily specified based on a partial region indicated on the panoramic image, the specified section being located in a space previously set to enclose the predetermined section and to enable the X-ray to pass therethrough; and contrast enhancement means for enhancing contrast of the partial sectional image produced by the partial sectional image producing means, wherein the contrast enhancement means comprises:

decomposition means for decomposing data of the partial sectional image produced by the partial sectional image producing means into coefficient data composed of low frequency components and high frequency components by applying multiresolution decomposition technique to the data of the partial sectional image;

weighting means for weighting the high frequency components with the use of weights for either part or all of a plurality of levels of the multiresolution decomposition technique, level by level, the weights depending on a feature given by densities of the partial sectional image; and reconstruction means for reconstructing the coefficient data having coefficients of the weighted high frequency components into a new image.

11. The panoramic imaging apparatus of claim 10, wherein the decomposition means comprise means for resetting or estimating a horizontal and vertical size of the partial sectional image into a power-of-two sized image, means for decomposing the original image into sub-bands having the coefficient data by applying a wavelet transform to the power-of-two sized image at the respective levels, the wavelet transform being the multiresolution decomposition technique, and the reconstruction means is configured to reconstruct the new image by applying an inverse wavelet transform to the sub-bands weighed by the weighting means.

* * * * *

UNITED STATES PATENT AND TRADEMARK OFFICE
CERTIFICATE OF CORRECTION

PATENT NO.        : 8,433,033 B2  Page 1 of 1
APPLICATION NO. : 12/083777
DATED             : April 30, 2013
INVENTOR(S)      : Harata et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1347 days.

Signed and Sealed this
Eighth Day of September, 2015

Michelle K. Lee
*Director of the United States Patent and Trademark Office*